(12) United States Patent
Ehrenreich et al.

(10) Patent No.: US 8,480,650 B2
(45) Date of Patent: Jul. 9, 2013

(54) METHOD FOR INCREASED UPTAKE OF BENEFICIAL AGENT AND EJECTION FRACTION BY POSTCONDITIONING PROCEDURES

(75) Inventors: Kevin Ehrenreich, San Francisco, CA (US); Jesus Magana, Redwood City, CA (US); Paul Consigny, San Jose, CA (US); Syed Hossainy, Hayward, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 18 days.

(21) Appl. No.: 13/098,092

(22) Filed: Apr. 29, 2011

(65) Prior Publication Data

US 2011/0270225 A1 Nov. 3, 2011

Related U.S. Application Data

(63) Continuation-in-part of application No. 12/771,946, filed on Apr. 30, 2010, and a continuation-in-part of application No. 12/771,968, filed on Apr. 30, 2010, and a continuation-in-part of application No. PCT/US2010/033270, filed on Apr. 30, 2010, and a continuation-in-part of application No. PCT/US2010/033276, filed on Apr. 30, 2010, and a continuation-in-part of application No. 13/032,733, filed on Feb. 23, 2011, and a continuation-in-part of application No. 13/032,743, filed on Feb. 23, 2011, now Pat. No. 8,366,659.

(51) Int. Cl.
*A61M 31/00* (2006.01)

(52) U.S. Cl.
USPC .............................. 604/509; 604/99.02

(58) Field of Classification Search
USPC ................ 604/99.02, 99.01, 96.01, 508–509
See application file for complete search history.

(56) References Cited

U.S. PATENT DOCUMENTS

| | | | |
|---|---|---|---|
| 4,740,203 | A | 4/1988 | Hoskins et al. |
| 4,861,520 | A | 8/1989 | van't Hooft et al. |
| 4,878,898 | A | 11/1989 | Griffin et al. |
| 5,011,468 | A | 4/1991 | Lundquist et al. |
| 5,336,184 | A | 8/1994 | Teirstein |
| 5,425,713 | A | 6/1995 | Taylor et al. |
| 5,500,013 | A | 3/1996 | Buscemi et al. |
| 5,728,064 | A * | 3/1998 | Burns et al. ............. 604/100.01 |
| 5,749,852 | A | 5/1998 | Schwab et al. |
| 5,925,054 | A | 7/1999 | Taylor et al. |
| 5,972,019 | A | 10/1999 | Engelson et al. |

(Continued)

FOREIGN PATENT DOCUMENTS

WO WO01/41861 6/2001

OTHER PUBLICATIONS

Jan. 5, 2012 Office Action issued in U.S. Appl. No. 12/771,946, filed Apr. 30, 2010.

(Continued)

*Primary Examiner* — Nicholas Lucchesi
*Assistant Examiner* — Melissa A Snyder
(74) *Attorney, Agent, or Firm* — Walter M Egbert, III; Lisa A. Chiarini; Hughes Hubbard & Reed LLP

(57) ABSTRACT

A method for improving tissue uptake of beneficial agent and ejection fraction.

15 Claims, 43 Drawing Sheets

U.S. PATENT DOCUMENTS

| | | | |
|---|---|---|---|
| 5,976,119 | A | 11/1999 | Spears et al. |
| 6,071,305 | A | 6/2000 | Brown et al. |
| 6,295,990 | B1 | 10/2001 | Lewis et al. |
| 6,435,189 | B1 | 8/2002 | Lewis et al. |
| 6,436,087 | B1 | 8/2002 | Lewis et al. |
| 6,436,090 | B1 | 8/2002 | Sanchez et al. |
| 6,468,200 | B1 | 10/2002 | Fischi |
| 6,580,457 | B1 | 6/2003 | Armstrong et al. |
| 6,746,465 | B2 | 6/2004 | Diederich et al. |
| 6,767,345 | B2 | 7/2004 | St. Germain et al. |
| 6,900,008 | B2 | 5/2005 | Vinten-Johansen et al. |
| 6,986,880 | B2 | 1/2006 | Coniglione et al. |
| 7,166,097 | B2 | 1/2007 | Barbut |
| 7,220,252 | B2 | 5/2007 | Shah |
| 7,335,192 | B2 | 2/2008 | Keren et al. |
| 7,364,566 | B2 | 4/2008 | Elkins et al. |
| 7,468,028 | B2 | 12/2008 | Schneider et al. |
| 7,468,070 | B2 | 12/2008 | Henry et al. |
| 7,686,781 | B2 | 3/2010 | Vinten-Johansen |
| 2003/0078538 | A1 | 4/2003 | Neale et al. |
| 2003/0199865 | A1 | 10/2003 | Knudson et al. |
| 2003/0199917 | A1 | 10/2003 | Knudson et al. |
| 2004/0111079 | A1 | 6/2004 | Hayes et al. |
| 2004/0243057 | A1 | 12/2004 | Vinten-Johansen |
| 2004/0255956 | A1 | 12/2004 | Vinten-Johansen et al. |
| 2005/0070848 | A1 | 3/2005 | Kim et al. |
| 2005/0118562 | A1 | 6/2005 | Vinten-Johansen et al. |
| 2006/0030814 | A1 | 2/2006 | Valencia et al. |
| 2006/0064059 | A1 | 3/2006 | Gelfand et al. |
| 2006/0079573 | A1 | 4/2006 | Vinten-Johansen et al. |
| 2006/0100639 | A1 | 5/2006 | Levin et al. |
| 2006/0189960 | A1 | 8/2006 | Kesten et al. |
| 2006/0205671 | A1 | 9/2006 | Vinten-Johansen |
| 2007/0010847 | A1 | 1/2007 | Pepper |
| 2007/0129752 | A1 | 6/2007 | Webler et al. |
| 2007/0142818 | A1 | 6/2007 | Webler et al. |
| 2007/0160645 | A1 | 7/2007 | Vinten-Johansen |
| 2008/0097383 | A1 | 4/2008 | Vinten-Johansen |
| 2008/0097385 | A1 | 4/2008 | Vinten-Johansen et al. |
| 2009/0018498 | A1 | 1/2009 | Chiu et al. |
| 2010/0082012 | A1 | 4/2010 | Hattangadi et al. |

OTHER PUBLICATIONS

Apr. 5, 2012 Applicant response to Jan. 5, 2012 Office Action issued in U.S. Appl. No. 12/771,946, filed Apr. 30, 2010.

Jan. 5, 2012 Office Action issued in U.S. Appl. No. 13/098,134, filed Apr. 29, 2011.

Apr. 5, 2012 Applicant response to Jan. 5, 2012 Office Action issued in U.S. Appl. No. 13/098,134, filed Apr. 29, 2011.

Oct. 9, 2012 Office Action issued in U.S. Appl. No. 13/098,055, filed Apr. 29, 2011.

Feb. 11, 2013 response to Oct. 9, 2012 Office Action issued in U.S. Appl. No. 13/098,055, filed Apr. 29, 2011.

Oct. 17, 2012 Office Action issued in U.S. Appl. No. 13/032,733, filed Feb. 23, 2011.

Feb. 12, 2013 response to Oct. 17, 2012 Office Action issued in U.S. Appl. No. 13/032,733, filed Feb. 23, 2011.

Zhi-Qing Zhao and Jakob Vinten-Johansen, Postconditioning: Reduction of reperfusion-induced injury. Cardiovasc Res (2006) 70(2): 200-211.

Dirksen et al., "Reperfusion injury in humans: a review of clinical trials on reperfusion injury inhibitory strategies," Cardiovasc Res. Jun. 1, 2007;74(3):343-55. Epub Jan. 23, 2007.

Hanssen et al., "Heparin-releasing intravascular guidewires," Med Device Technol. Sep. 2002;13(7):20-2.

ISR/WO for PCT/US2010/033270 dated Jul. 9, 2010.

ISR/WO for PCT/US2010/033276 dated Jul. 30, 2010.

Jennings et al., "Preconditioning myocardium with ischemia," Cardiovascular Drugs and Therapy, vol. 5, No. 5, 933-938, DOI: 10.1007/BF00053555, 1991.

Kin et al., "Postconditioning attenuates myocardial ischemia—reperfusion injury by inhibiting events in the early minutes of reperfusion," Cardiovasc Res (2004) 62 (1): 74-85.

Murry et al., "Preconditioning with ischemia: a delay of lethal cell injury in ischemic myocardium," Circulation. 1986;74:1124-1136.

Peerlings et al., "Heparin release from slippery-when-wet guide wires for intravascular use," J Biomed Mater Res. 2002;63(6):692-8.

Piot et al., "Effect of Cyclosporine on Reperfusion Injury in Acute Myocardial Infarction," N Engl J Med. Jul. 31, 2008;359(5):473-8.

Poppenga et al., "Assessment of Potential Therapies for Acute T-2 Toxicosis in The Rat," 1987, Toxicon, vol. 25, No. 5, pp. 537-546, Department of Veterinary Biosciences, University of Illinois, Urbana, IL 61801, U.S.A.

Staat et al., "Postconditioning the Human Heart," Circulation. 2005;112:2143-2148.

Tsang et al., "Postconditioning: A Form of "Modified Reperfusion" Protects the Myocardium by Activating the Phosphatidylinositol 3-Kinase-Akt Pathway," Circulation Research. 2004;95 :230-232.

Vasquez et al., "Myocardial protection with preconditioning," Circulation. 1990;82:609-619.

Yang et al., "Multiple, brief coronary occlusions during early reperfusion protect rabbit hearts by targeting cell signaling pathways," Journal of the American College of Cardiology, vol. 44, Issue 5, Sep. 1, 2004, pp. 1103-1110.

Yellon et al., "Myocardial reperfusion injury," N Engl J Med. Sep. 13, 2007;357(11):1121-35.

Zhao et al., "Inhibition of myocardial injury by ischemic postconditioning during reperfusion: comparison with ischemic preconditioning," AJP—Heart Aug. 2003 vol. 285 No. 2 H579-H588.

Zhao, "Ischemic Postconditioning as a Novel Avenue to Protect Against Brain Injury After Stroke" Journal of Cerebral Blood Flow & Metabolism (2009) 29, 873-885, Department of Neurosurgery, Stanford University School of Medicine, Stanford, California, U.S.A.

* cited by examiner

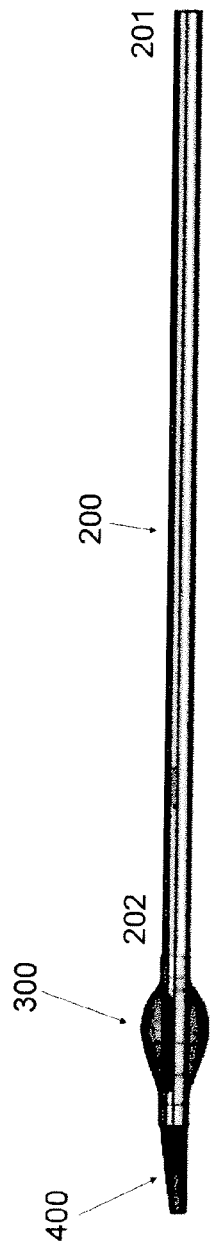
FIGURE 9A
FIGURE 9C
FIGURE 9B

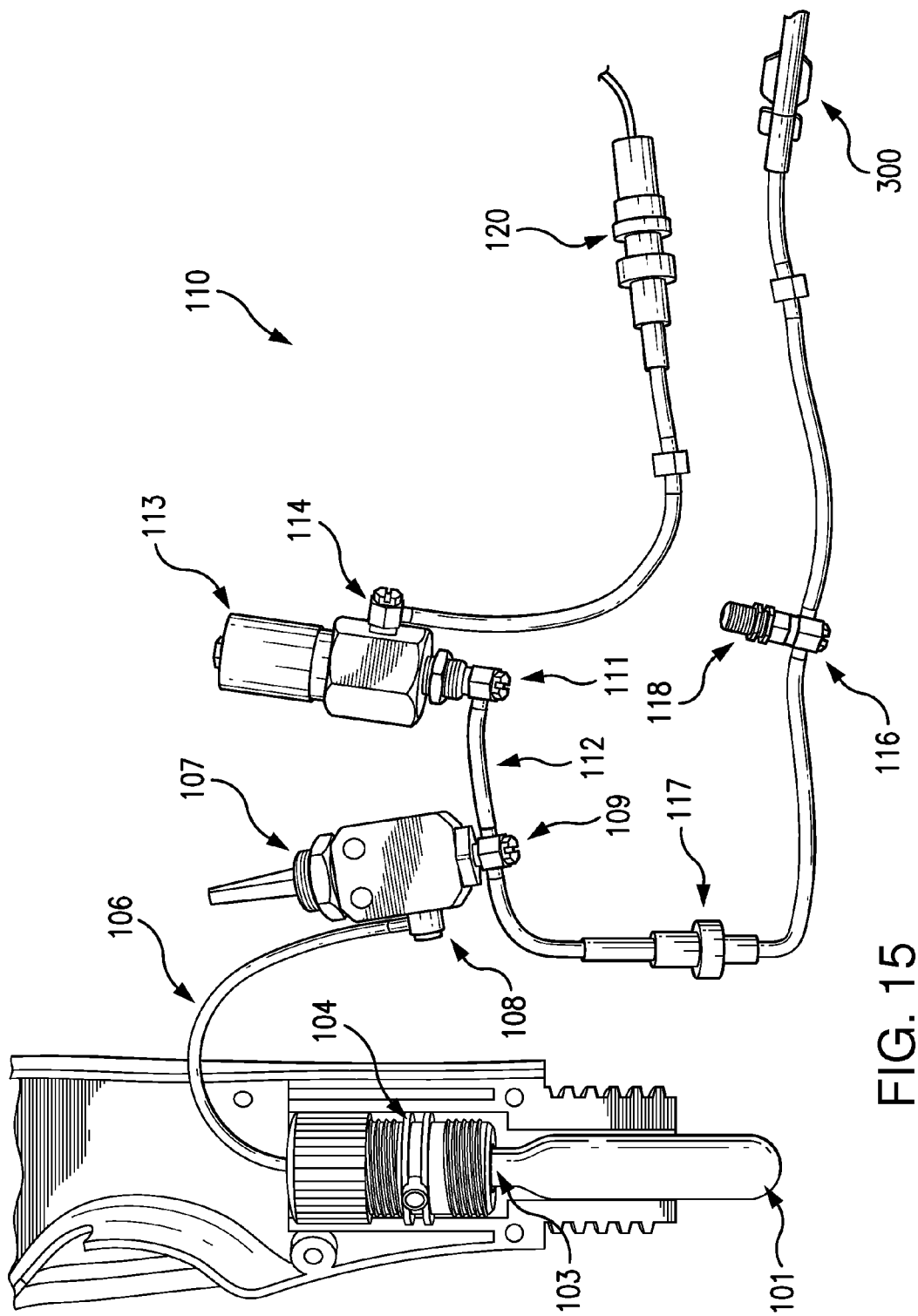

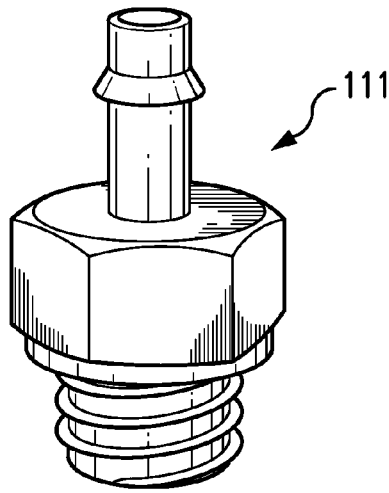
FIG. 18M
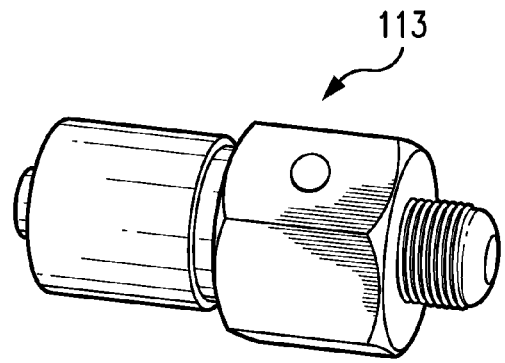
FIG. 18N
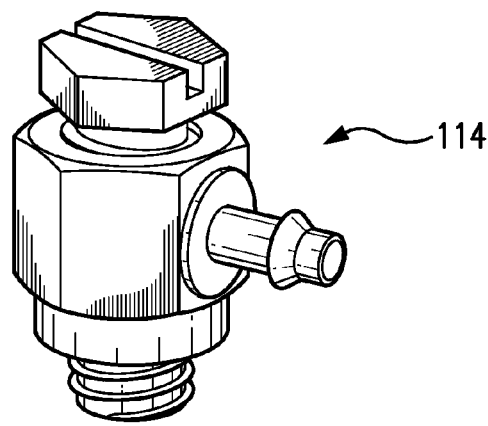
FIG. 18O
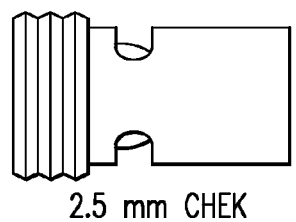
2.5 mm CHEK
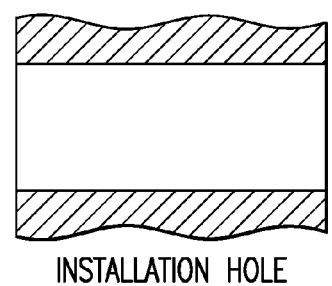
INSTALLATION HOLE
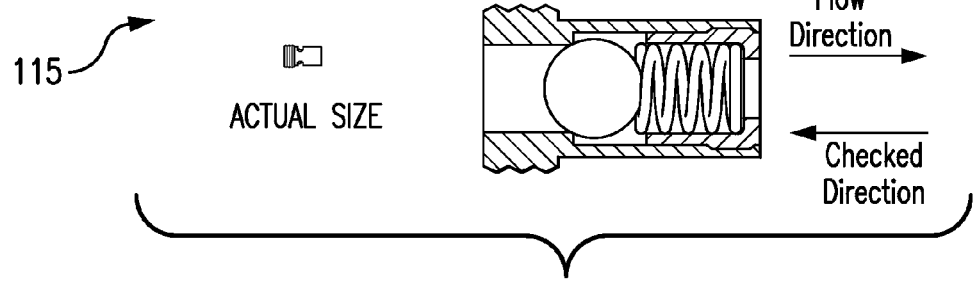
FIG. 18P

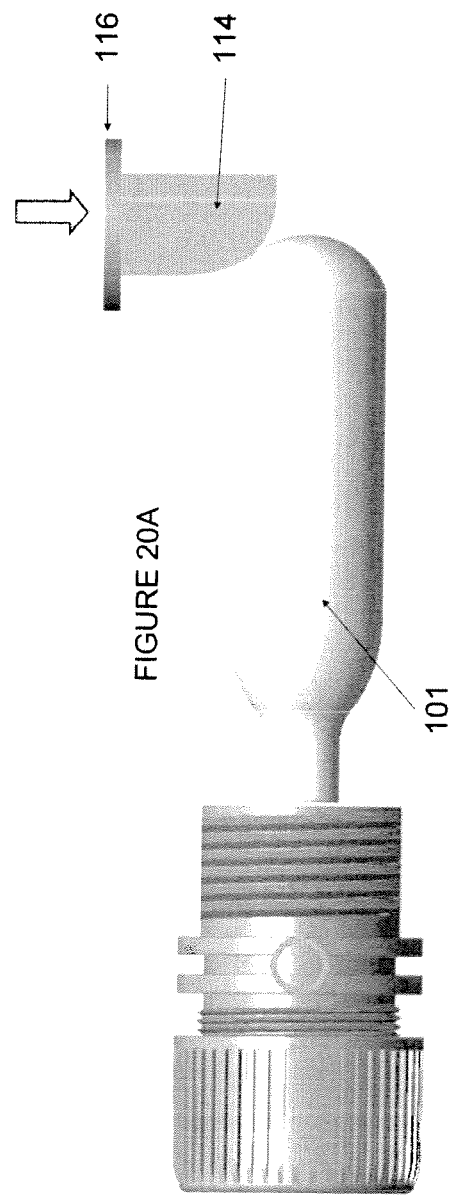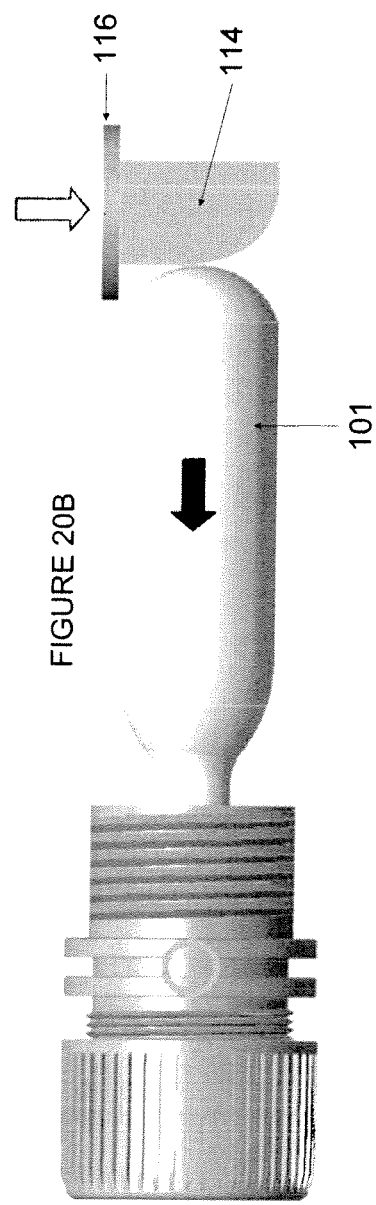

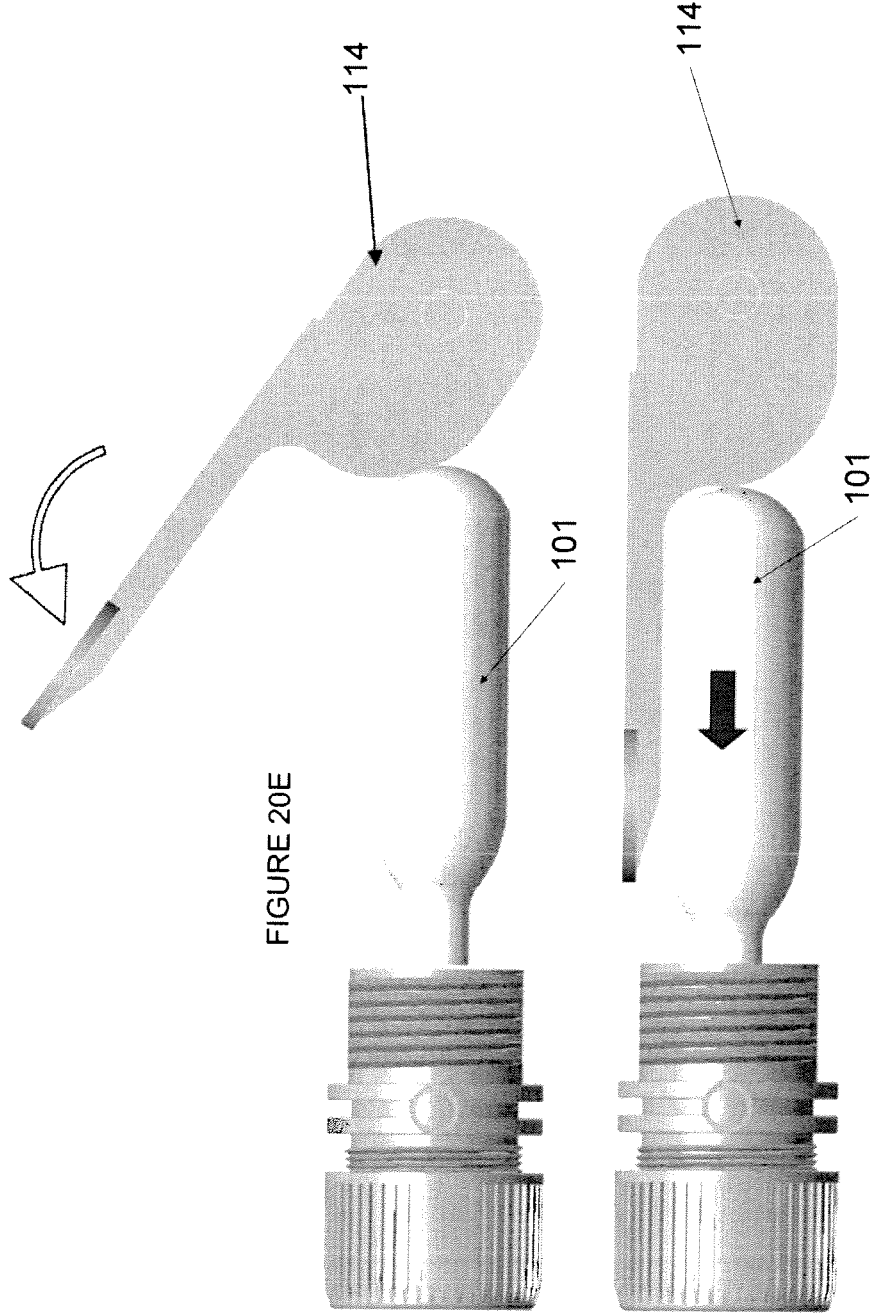

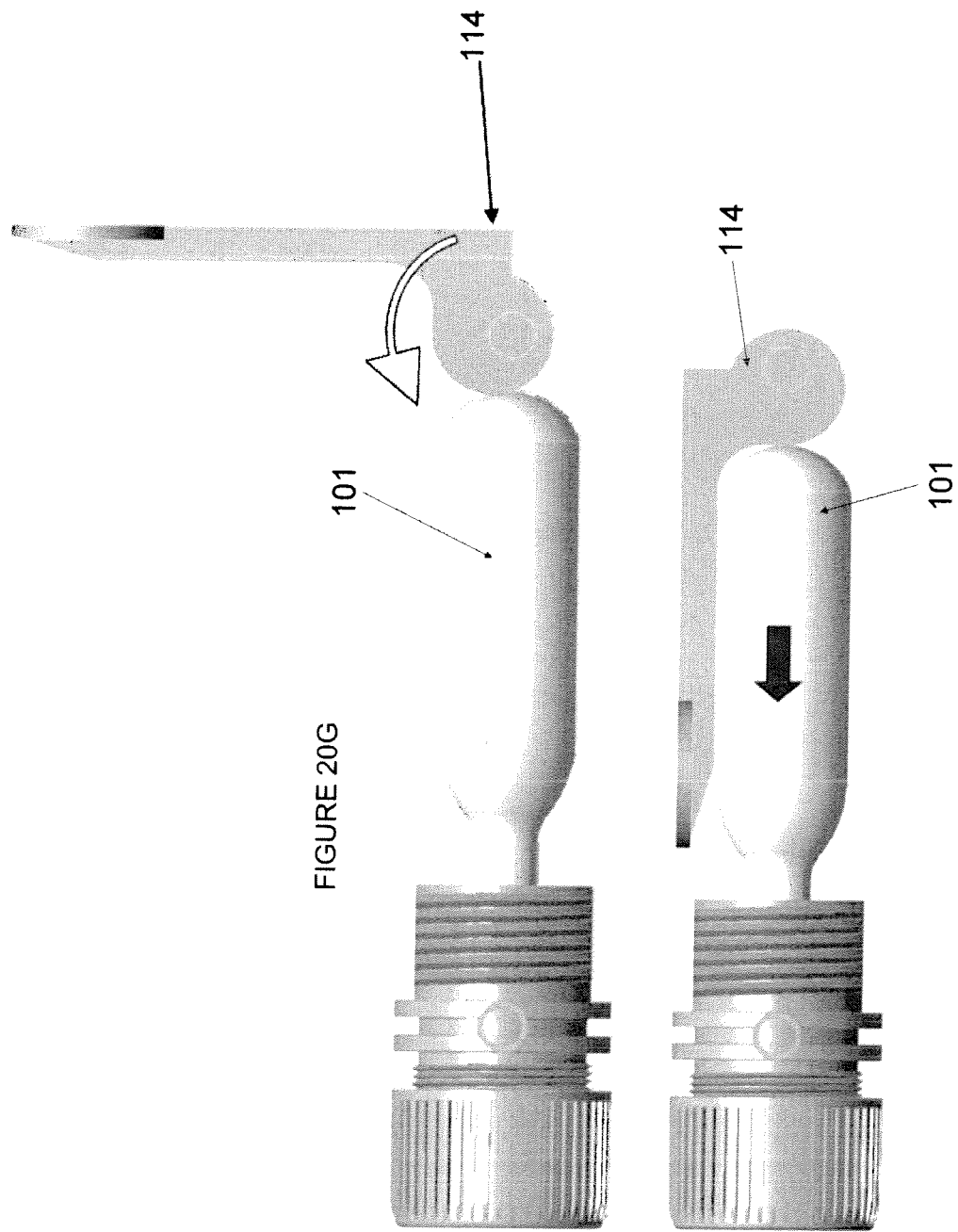

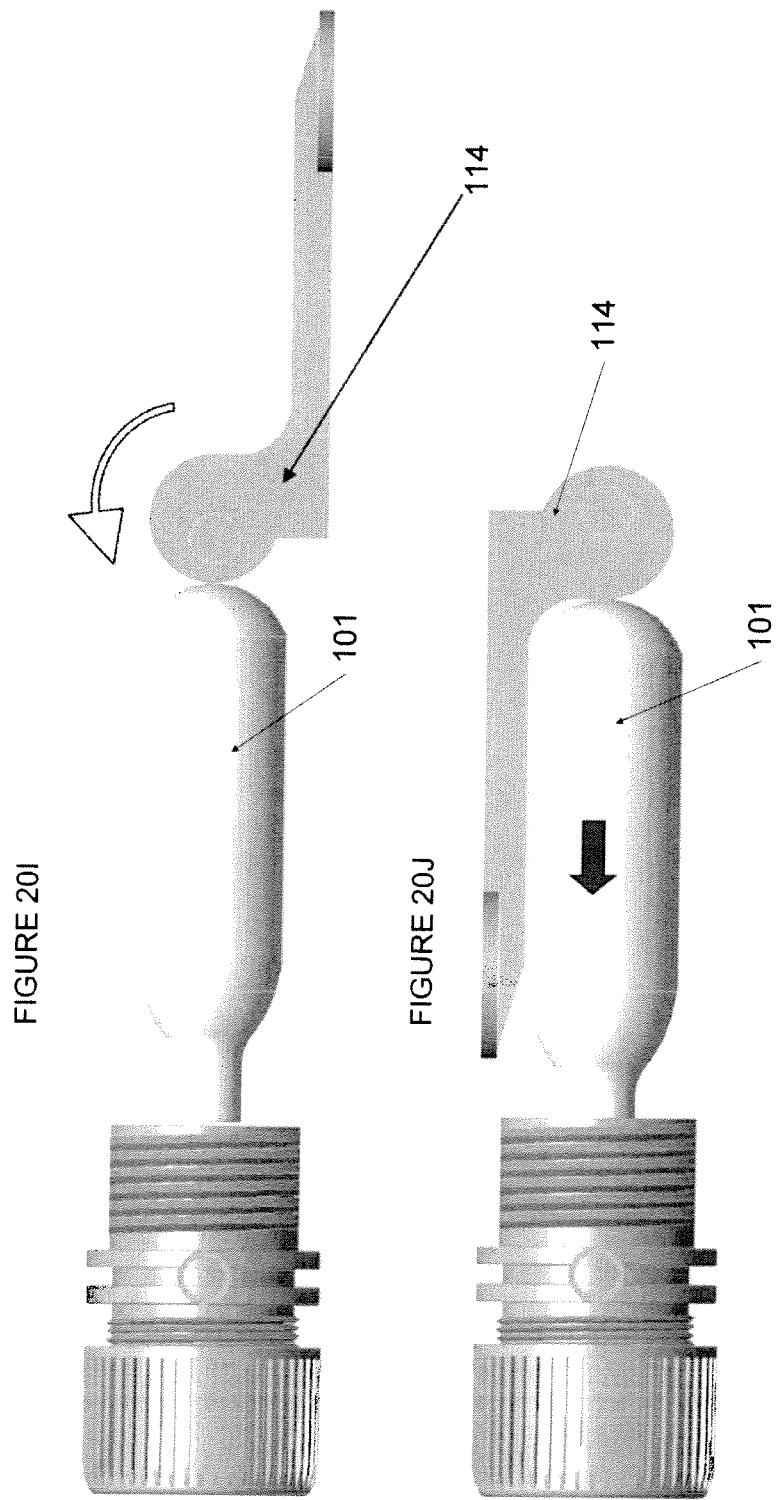

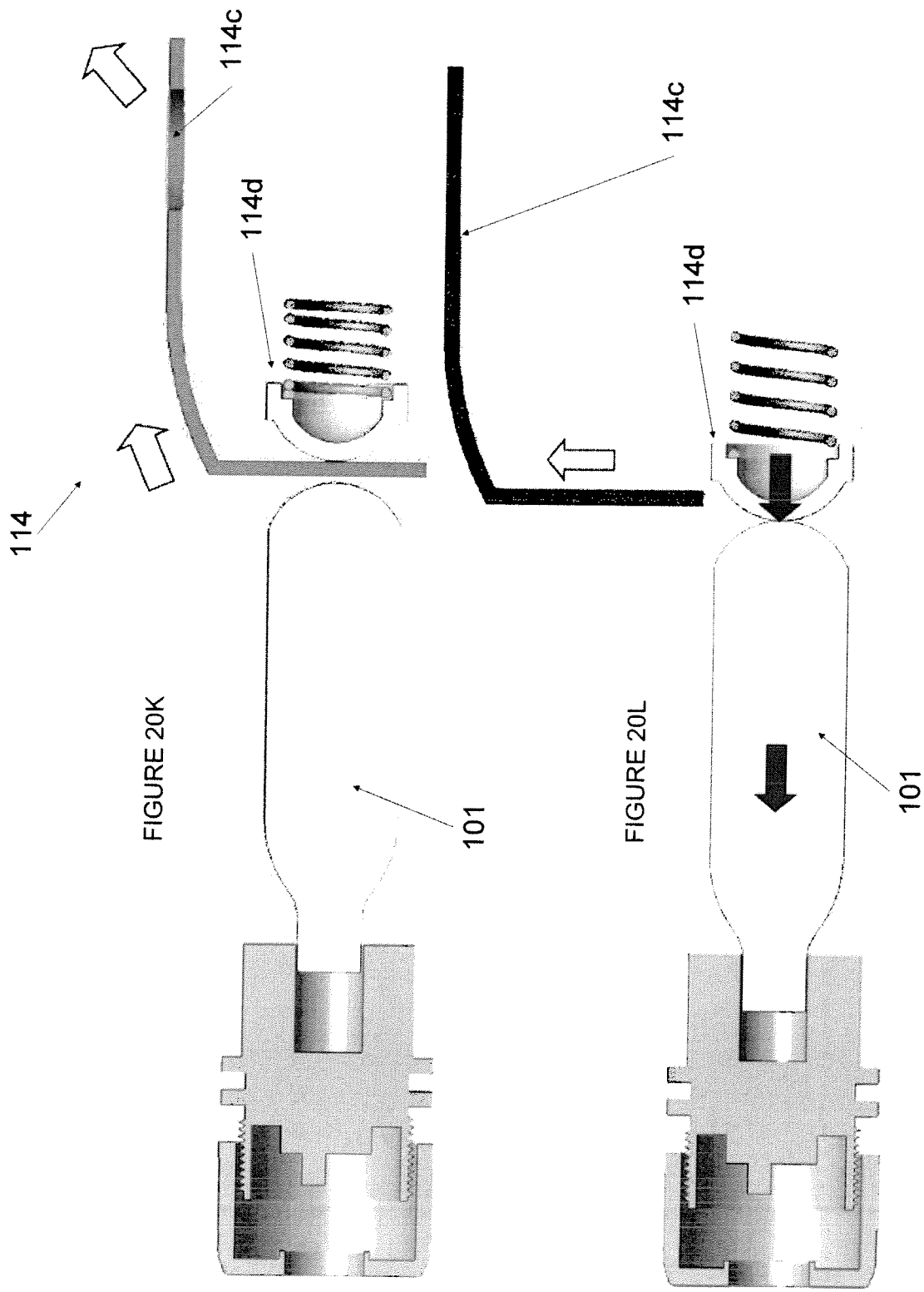

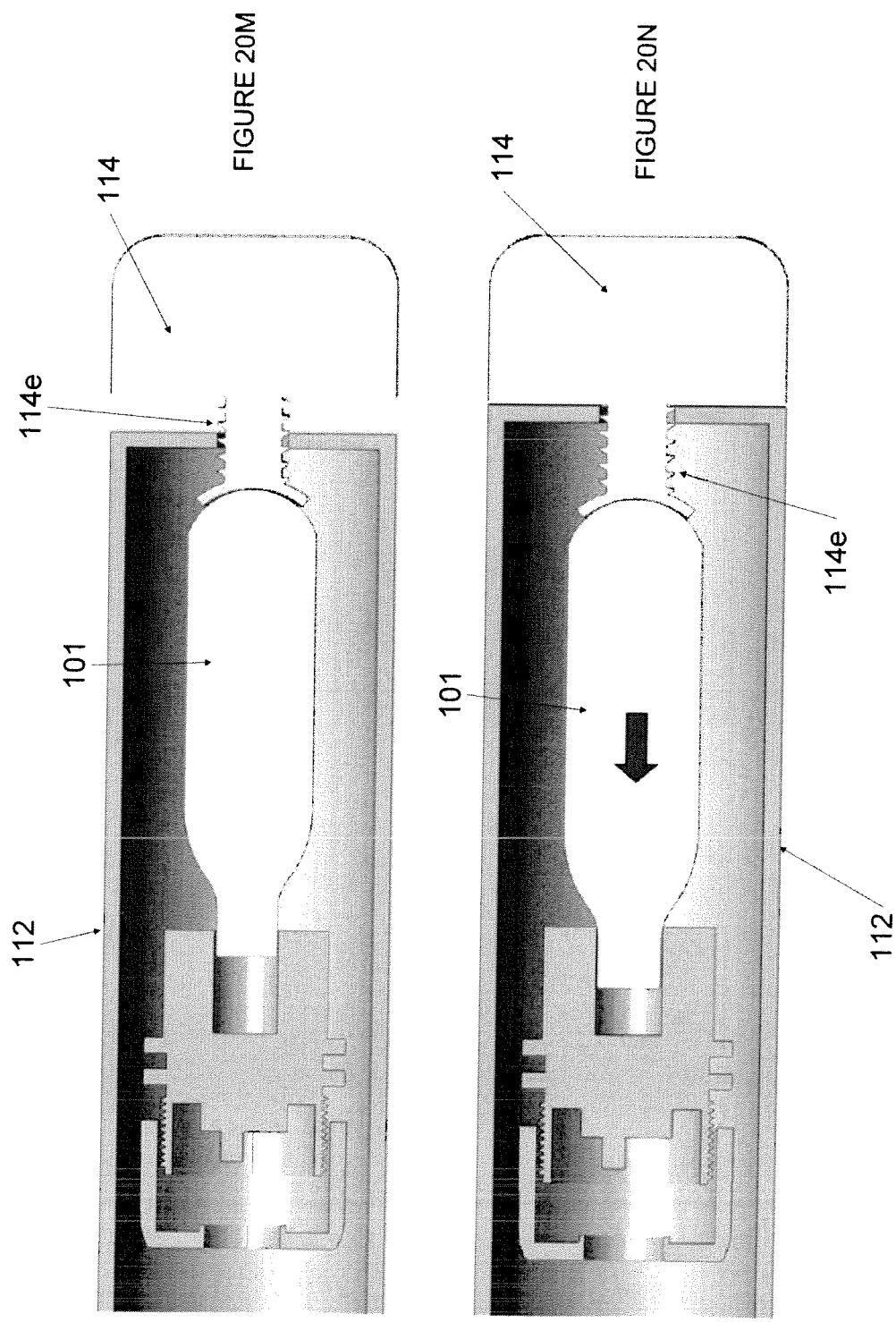

METHOD FOR INCREASED UPTAKE OF BENEFICIAL AGENT AND EJECTION FRACTION BY POSTCONDITIONING PROCEDURES

CROSS REFERENCE TO RELATED APPLICATIONS

This application is a continuation-in-part of co-pending, U.S. patent application Ser. No. 12/771,946, filed Apr. 30, 2010, U.S. patent application Ser. No. 12/771,968, filed Apr. 30, 2010, PCT/US2010/033270, filed Apr. 30, 2010, PCT/US2010/033276, filed Apr. 30, 2010, U.S. patent application Ser. No. 13/032,733, filed Feb. 23, 2011, U.S. patent application Ser. No. 13/032,743, filed Feb. 23, 2011 the disclosures of each of which are hereby incorporated by reference in their entireties.

TECHNICAL FIELD

The subject matter relates to methods and devices to improve recovery or rehabilitation of an individual.

BACKGROUND

Usually, the term "postconditioning" refers to a method during which the blood flow in an artery is stopped and started for multiple cycles immediately after re-opening initial blood flow in an occluded blood vessel, such as from a ST segment elevation myocardial infarction ("STEMI"). The postconditioning technique is generally used to reduce reperfusion injury in a person suffering from an ischemic event. Currently, physicians perform postconditioning techniques for the purpose of reducing reperfusion injury with a conventional angioplasty catheter. At this time, there is no catheter on the marketplace designed to perform postconditoining techniques in a blood vessel of a subject. Further, angioplasty catheters have been known to be modified or configured to locally deliver therapeutic agents to the vasculature of a subject. There is a need for methods and devices for increased uptake of drugs and other agents into the tissue of subjects.

The disclosed subject matter addresses these needs by providing methods and devices to perform postconditioning in a blood vessel and which exhibits increased uptake of the beneficial agent into the system of the subject. The methods and device also improve ejection fraction of a subject after an ischemic event.

The present invention provides methods for using a catheter to deliver beneficial agents during postconditioning of a blood vessel with the benefit of increast tissue uptake and have been known to be drug delivery devices in addition to A conventional angioplasty balloon catheter is not optimized to sequentially inflate and deflate for multiple cycles. Further the rapid exchange catheter is not designed to locally deliver a beneficial agent to distal to the balloon or ischemic site. Therefore, a need exists for a reperfusion device that is adapted to locally deliver a beneficial agent to synergistically improve inhibition of reperfusion injury.

SUMMARY

In accordance with one aspect of the disclosed subject matter, a method for improving tissue uptake of a beneficial agent is provided. It has surprisingly been found that the methods and device for postconditioning of the subject matter described herein result in an increased uptake of beneficial agent into the tissue of a subject. The method includes locally administering a beneficial agent to the vasculature of a subject during sequential cycles of inflating and deflating a balloon. The term "cycle" refers to one inflation followed by one deflation of the balloon. For ease of discussion, multiple cycles may sometimes be referred to as be referred to as postconditioning throughout the present disclosure.

In some embodiments, the balloon is sequentially inflated and deflated for at least two cycles and preferably more than eight cycles. The catheter is configured to inflate in less than four seconds and deflate in less than five seconds. In some embodiments, for example, the balloon can be inflated in less than one second. In one embodiment, the balloon can be deflated in one minute or less. Accordingly, one cycle of inflation and deflation can occur in less than two seconds. The inflation and deflation in rapid and efficient succession modulates the blood flow through the blood vessel of the subject.

A beneficial agent can be administered during the inflation part of the cycle, the deflation part of the cycle or both during inflation and deflation. It has been found that the method for administering a beneficial agent as described can result in a four-fold increase in tissue uptake of the beneficial agent. In other embodiments, the increase in uptake is greater than one-hundred fold. On average, in some embodiments, the increased uptake is at least forty-fold.

The method can also exhibit a concentration of beneficial agent in blood plasma at least one hour after cessation of administration. In one embodiment, the method can exhibit a plasma concentration of beneficial agent at least two hours after cessation of administration of the beneficial agent and inflation and deflation of the balloon.

Various beneficial agents can be employed with the method and device described. The beneficial agents can be selected from the group consisting of: a calpain inhibitor, pH stabilizing agent, or an endothelin receptor blocker. In other embodiments, the beneficial agent can be a biomaterial. In some embodiments the beneficial agent is a zinc chelator. The zinc chelator is a pendant group to a polymer or a pendant group to a biomaterial. In some embodiments, the beneficial agent can be a formulation of a zinc chelator and a vasodilator. The formulation having zinc chelator can be employed to modulate tissue remodeling. In this regard, the formulation can be administered to a coronary vasculature to modulate an infarcted area of a tissue. Suitable vasodilators can include acetohydroxamic acid, N-(methyl)mercaptoacetamide, 3-Hydroxy-pyran-4-one, 1-Hydroxy-1H-pyridin-2-one, 3-Hydroxy-1-methyl-1H-pyridin-2-one, 3-Hydroxy-2-methyl-pyridin-4-one, 3-Hydroxy-1,2-dimethyl-1H-pyridin-4-one, 1-Hydroxy-1H-pyridine-2-thione, 3-Hydroxy-2-methyl-pyran-4-thione, 3-Hydroxy-1H-pyridin-2-one, 3-Hydroxy-pyran-4-thione, 3-Hydroxy-1-methyl-1H-pyridine-2-thione, and 3-Hydroxy-1,2-dimethyl-1H-pyridine-4-thione.

In another aspect, a method for improving ejection fraction is described. In accordance with the method a catheter is introduced to the ischemic lumen of a subject. The catheter includes an inflation lumen and an separate dedicated deflation lumen disposed between a proximal end and a distal end of the catheter and a balloon disposed on the catheter. The method includes sequentially inflating and deflating the balloon for at least two cycles. It has been found that the method improves the ejection fraction to at least 30%.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 9A-9C are schematic illustrations of the catheter shaft in accordance with embodiments of the disclosed subject matter;

FIG. 15 is an exploded view of fluid circuit in accordance with one embodiment of the disclosed subject matter;

DETAILED DESCRIPTION OF EXEMPLARY EMBODIMENTS

I. Method Overview

A method for synergistically mitigating reperfusion injury in a mammal that has suffered an ischemic event is described. Generally, the method includes locally delivering a beneficial agent to the vessel during postconditioning after an ischemic event. The ischemic event can be due to a blockage in a variety of different vasculature or microvasculature systems of a mammal. For example, the particular vasculature may include that of the coronary, spinal, peripheral or cerebral systems. The method can be used, for example, to mitigate cerebral injury after a stroke, coronary injury after a heart attack, spinal or peripheral injuries after an embolism, or other ailment involving a lack of blood supply and deprivation of oxygen.

Figure 1A:
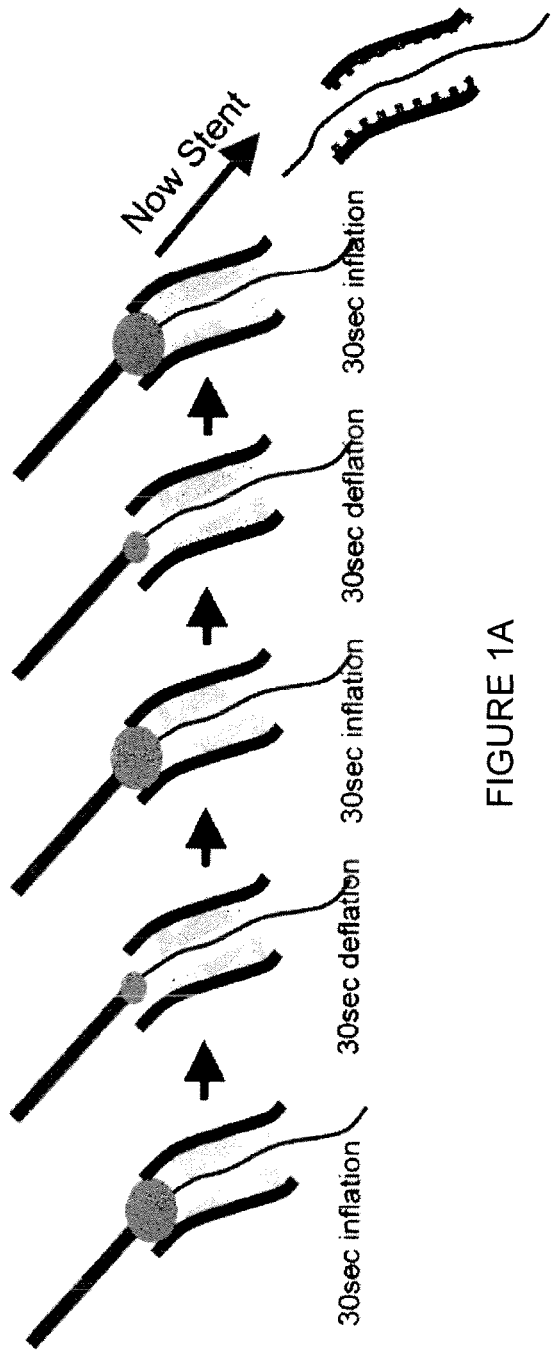
FIGS. 1A and 1B are schematic views of exemplary postconditioning techniques in accordance with the disclosed subject matter.
Figure 1B:
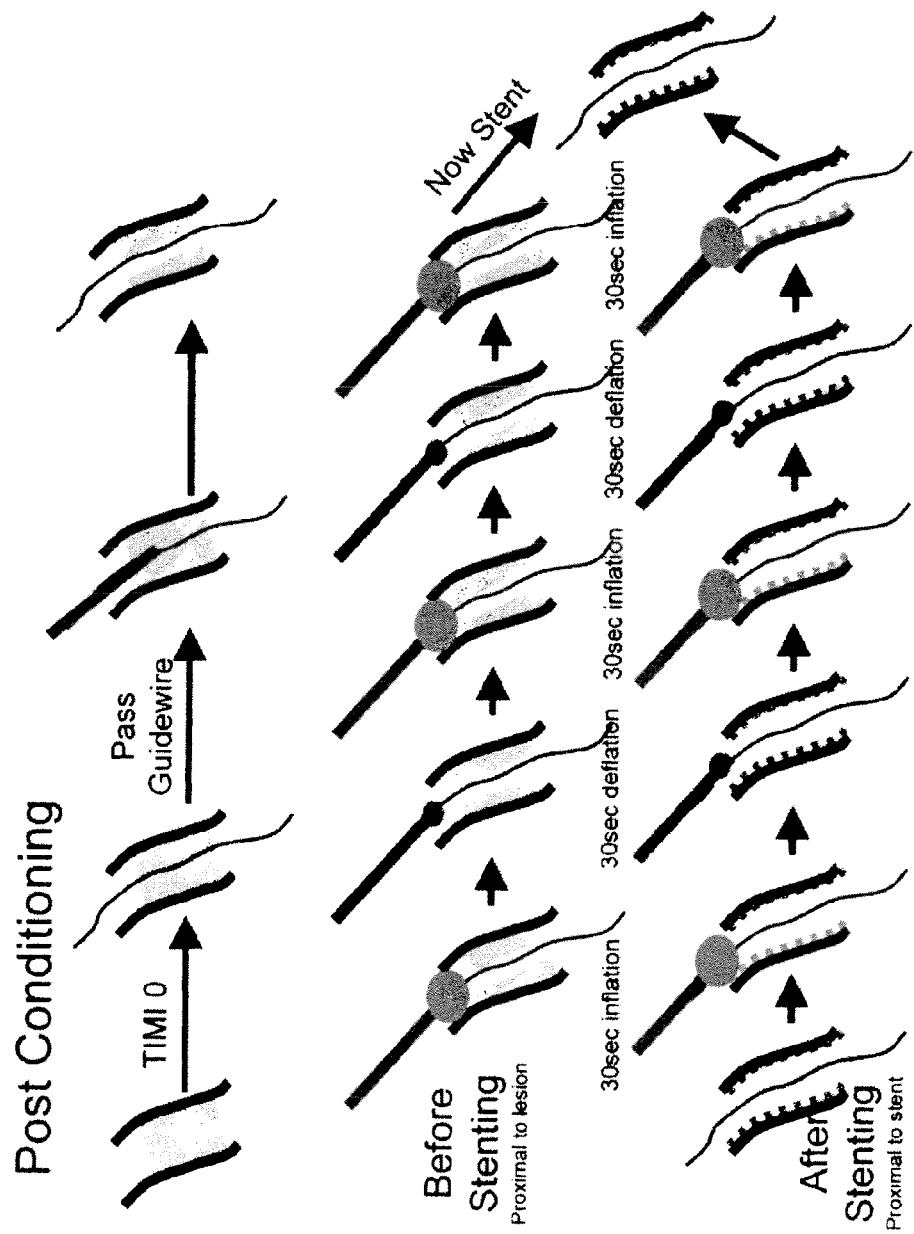

As illustrated in FIG. 1A, one embodiment of a postconditioning method is shown. The balloon catheter device embodied and described below is introduced through a blood vessel to a position proximal or proximate to a lesion site. The balloon is temporarily inflated to stop perfusion of the blood through the blood vessel for an amount of time, and subsequently temporarily deflated for an amount of time to permit reperfusion of the blood through the blood vessel for a period of time. The postconditioning procedure can be employed before stenting the blood vessel, for example, as illustrated in FIG. 1A. As illustrated in FIG. 1B, postconditioning can be performed before stenting and after stenting. In the case where postconditioning is performed after stenting the balloon is preferably inflated and deflated proximal to the stent. Although the balloon can be sequentially inflated and deflated within the lumen of the stent. For the purpose of illustration, postconditioning methods are also described in U.S. Patent Publication Nos. 2004/0255956 and 2007/0160645 to Vinten-Johansen, the disclosures of which are hereby incorporated by reference for all purposes.

Mechanical postconditioning provides a unique opportunity to deliver one or more beneficial agents to the ischemic blood vessel and to the tissue or organ downstream from the ischemia, such as the myocardium, at the time of reperfusion. The beneficial agent can be directly delivered to the blood vessel during the postconditioning cycles of inflation (occlusion) or deflation (nonocclusion) or both. In this manner, beneficial agent can be administered at a concentration higher than would be if administered intravenously. Additionally, the dwell time of the concentrated beneficial agent in the vessel is greater when delivered during postconditioning than when delivered by a conventional coronary catheter without temporary occlusion.

Figure 2:
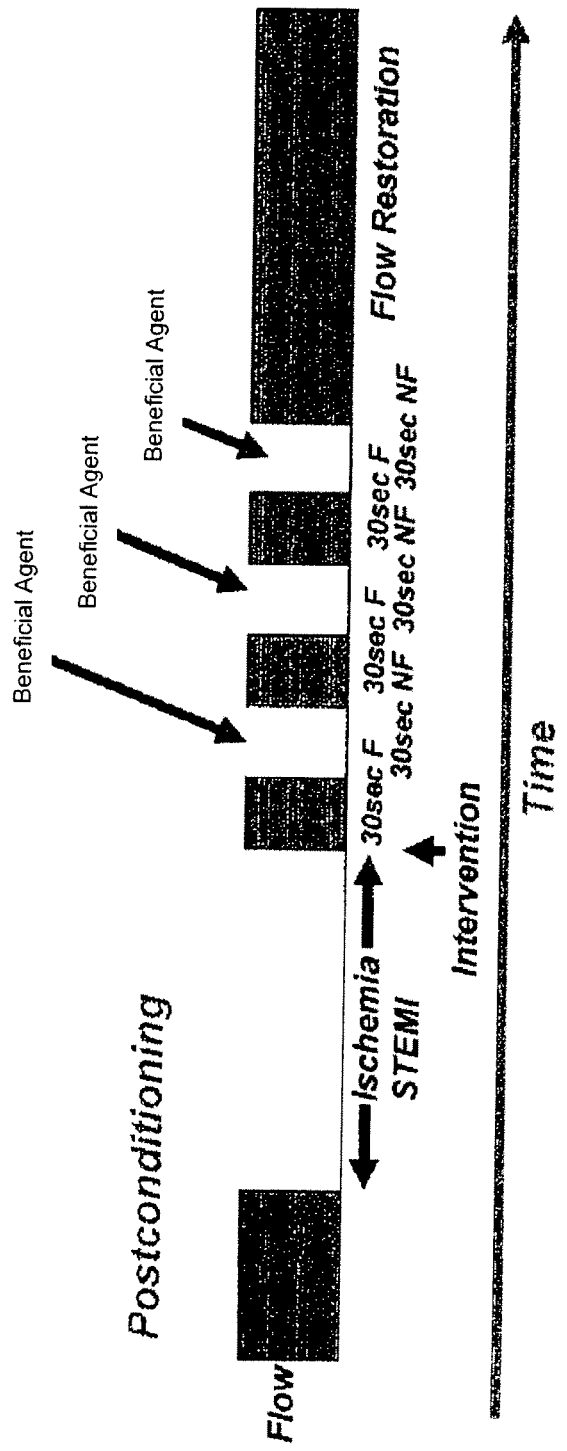
FIG. 2 is a schematic illustration of synergistic mechanical postconditioning and local beneficial agent therapy in accordance with one embodiment of the disclosed subject matter.

In one embodiment, as illustrated in FIG. 2, the postconditioning procedure can include 30-second cycles of balloon inflation and deflation to achieve alternating 30-second cycles of blood flow and no-flow. Additionally, the postconditioning method and device can include local delivery of beneficial agent during the no-flow cycle, as shown. In some embodiments, beneficial agent can be locally administered for one or more no-flow cycles. As illustrated in FIG. 2, one embodiment of the method includes local delivery of beneficial agent during every period of occlusion or no flow cycles after ischemia. However, the beneficial agent can be delivered during both the inflation and deflation stages of postconditioning. In this regard, the delivered beneficial agent will be in stasis during the inflation cycle and flow during deflation cycle. The local delivery of beneficial agent during postconditioning synergistically mitigates reperfusion injury.

It is contemplated herein that various beneficial agents can be locally delivered during postconditioning to synergistically mitigate reperfusion injury after ischemia in a mammal. It has been found that local delivery of beneficial agent during postconditioning results in significantly increased uptake of the beneficial agent in the tissues of a mammal. It is believed that the estimated postconditioning tissue concentration at inflation stage of a postconditioning procedure is $C'=(A/V)*K'*Co*Exp-(k+k')*t'$; $0<t<t'$=inflation time. The estimated postconditioning tissue concentration at deflation stage is believed to be $C''=(A/V)*K'*C'*Exp-(k'/R)*t''-(A/V)C'*Exp-(k'/R)*(t-x/V)$. In contrast, regular intracoronary procedures without post conditioning is believed to be $C=(A/V)*K'C'*Exp-(k'*x/V/R)f(t-x/V)$. Accordingly, the tissue concentration of beneficial agent is greater due to postconditioning cycle of inflation-deflation.

As used herein, a "beneficial agent" includes any agent that promotes health, recovery or diagnosis. For example, the beneficial agent may be a drug, protein, or contrast agent. Suitable beneficial agents include calpain inhibitors, endothelin receptor blockers, pH stabilizing agent, chymase inhibitors, oxygen and oxygen mixtures, antithrombotic agents, proteins, cells or vectors including angiogenic factors, and biomaterials. Other examples of beneficial agents include nitroglycerin, epinepharin, lydocaine, heparin, hirudin, and ReoPro™. As will be recognized in the art, however, other drugs or beneficial agents may be employed.

Nonlimiting examples of calpain inhibitors include ABT-099, A-965431, A705253, A-705239, or racemates and mixtures thereof. Other examples of calpain inhibitors are disclosed in WO 98/25899, WO 98/25883, WO 9954305, WO 99/54310, WO 99/61423, WO 00/78933, WO 2008/080969, WO 2009/083581, U.S. Publication Nos. 2006/0205671 and 2008/0097385, each of the disclosures of which are incorporated herein by reference. The process of reperfusion in patients with an occluded artery results in an influx of calcium into the cardiomyocytes, which stimulate calcium dependent enzyme calpain. Activation of calpain subsequently results in the degradation of cytoskeletal proteins (i.e., Fodrin) resulting in an increase in membrane fragility. The fragility combined with the influx of fluids into the ischemic cell can result in cell swelling and death.

In one embodiment, the beneficial agent is a mixture of calpain inhibitor, dexamethasone, and adenosine. In another embodiment, the method includes a combination of local delivery of calpain inhibitor during postconditioning, and sustained release of adenosine. For example, a stent eluting adenosine or an analog thereof can be deployed in the blood vessel. In some embodiments, the stent can be designed to elute adenosine over a period of one to three days to reduce microvascular obstruction. In other embodiment, the stent eluting adenosine or an analog thereof for a period of seven days or longer to prevent stent thrombosis. Thus, the disclosure includes methods to reduce or mitigate microvascular obstruction and stent thrombosis. "Stent thrombosis" refers to arterial injury and exposed thrombogenic material which is sometimes due to the placement of a stent.

Suitable endothelin receptor blockers include ET-A and/or ET-B receptor blockers, such as, Astrasentan (ABT-627; A-147627), ABT-546 (A-216546), and racemates thereof. Reperfusion in patients with occluded coronary arteries typically results in the release of factors that promote vasoconstriction and/or vasospasm of the distal vasculature. Some factors include endothelin, serotonin, 5-hydroxytryptamine, thromboxane, and histamine. The resultant vasoconstriction can lead to microvascular obstruction, i.e. no reflow, that can last for days to weeks and has been found to be predictive of ventricular remodeling. For example, it is believed that the volume of myocardium with no reflow is directly related to the likelihood of a patient developing left ventricular remodeling (increased diastolic volume), which can lead to heart failure. In one embodiment, the method includes mitigating ventricular remodeling by local delivery of an endothelin receptor blocker. Further, the endothelin receptor blocker, can be locally delivered during the time of reperfusion to mitigate microvascular obstruction and/or reduce infarct size. The endothelin receptor blocker can be locally delivered downstream of an occluded balloon during periods of occlusion, infusion downstream of an infusion catheter during periods of occlusion and during period of reflow, selective delivery to the artery supplying the reperfused tissue or organ though the cardiac cycle, selective delivered in the artier supplying the reperfused tissue during diastole for delivery to the endocardium. If one desires to maximize delivery of beneficial agent to the ischemic myocardium, systemic delivery of beneficial agent can be supplemented by intracoronary delivery, or intracoronary delivery of beneficial agent can be supplemented by intravenous delivery.

In yet another aspect the method, the pH of the vascular tissue can be stabilized after an ischemic event to optimize tissue viability. In this manner, local delivery of a pH stabilizing agent during postconditioning is described. In this way the abrupt changes to the blood vessel common to ischemic reperfusion treatment can be offset, and reperfusion injury and infarct size can be reduced. In one embodiment, a pH stabilizing agent is delivered to the vessel or vessel wall. Following reperfusion, the delivered pH stabilizing agent can travel into the affected tissue and control the rate at which oxygen is delivered into the tissue by the blood. As a result, the oxygenation and thus, the change in pH within the tissue can be modulated and occur over a longer period of time.

Allowing the tissue to gradually achieve homeostasis mitigates the stress placed on the tissue cells and optimizes tissue viability. It should be recognized that the modulation may be effected by various causes. For example, the therapeutic agent may reduce the rate at which oxygen is delivered by displacing volume within the target tissue and therefore preventing oxygenated blood from entering the tissue (at least partially). Alternatively, the beneficial agent may interact with the oxygen present in the blood to produced a chemical by-product that can enter the tissue and recue the pH therein. The pH stabilizing agents include, for example, a mixture of sodium carbonate and citric acid which produces carbon dioxide as a by-product, nitric oxide, and a mixture of nitric oxide and carbon dioxide. Each of which have the effect of reduction in pH and can control the rate of pH changes in the tissue. Suitable pH stabilizing agents include but are not limited to sodium carbonate and citric acid, nitric oxide, nitric oxide and carbon dioxide, all of which reduce pH within the infracted blood vessel. In one embodiment, the inflation fluid and the beneficial agent can be nitric oxide. Accordingly a perfusion balloon can inflate via nitric oxide as a medium.

In one embodiment, the beneficial agent can be adenosine and adenosine analogs. Suitable adenosine analogs include adenosine A1 agonists such as CVT-510, BN-063, CPA (N6-cyclopentyladenosine), CCPA (1 chloro N6-cyclopentyladenosine), and adenosine A2 agonists such as CGS21680, NECA N-ethylcaroxamide adenosine, 2HE-NECA, APEC (2[2-aminoethylaminocarbonylethylphenylethylamino]-5' N ethylcarboxamindoadenosine. The adenosine can be administered from an eluting stent to achieve a sustained release of beneficial gent. In one embodiment, the eluting stent can elute adenosine from seven days to about two to three months. In this manner, the sustained release of adenosine or its agonists can mitigate restenosis, stent thrombosis or microvascular obstruction (MVO).

In one embodiment, the method includes administering a sustained release of adenosine, infusing calpain inhibitor peri-procedurally, and mechanical postconditioning the ischemic blood vessel to achieve a synergistic or additive improvement to reducing infarct size during reperfusion therapy.

In yet another aspect, the beneficial agent includes chymase inhibitors. Some non-limiting examples of chymase inhibitors are provide below (SDF-1), glucagon-like peptide 1 (GLP-1), bleomycin and/or tetracycline. In this regard, platelets can be obtained from a donor. The platelets can be electroporated in the presence of SDF-1 to increase platelet SDF-1 content. Treating a subject who has suffered from a myocardial infarction can be treated by delivering the treated platelets locally into the coronary artery supplying the infracted myocardium.

In one embodiment, the beneficial agent is a biomaterial which when released during mechanical postconditioning can increase the residence time in the vasculature. This increment in residence time may enhance mass transport properties into the vessel downstream from the infarct-inducing

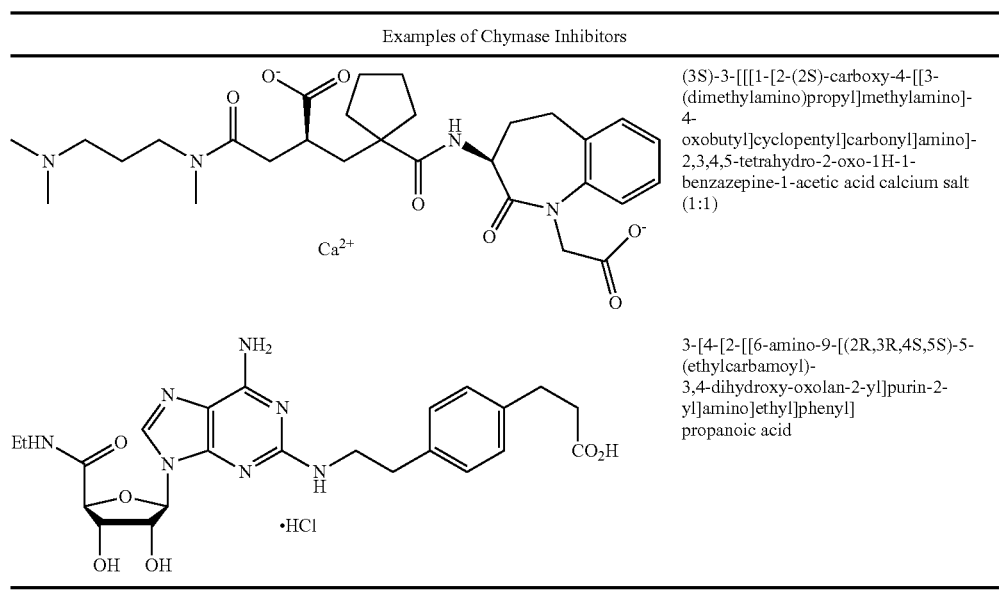

In one embodiment, the beneficial agent is oxygen, nitric oxide and oxygen, or reactive $O_2$ and oxygen. In this respect, the method includes cyclic delivery of oxygen to the vessel and/or infarct site during the sequential inflation and deflation of the balloon disposed within the blood vessel. For example, cyclic pressurized $O_2$ can be delivered to the left main coronary artery, left ventricle, left ventricular wall, right atrial passage. In some embodiments, artificial $O_2$ carrier such as $O_2$-rich perfluorocarbon fluid can be utilized. In another embodiment, a cyclic perfusion of artificial $O_2$ carrier can be introduced to the coronary vascular bed. The positive pressure at the left main artery in conjunction to negative pressure at the venous side will introduce a transient flow loop rich in $O_2$. In some embodiments, the pressurized $O_2$ can be locally delivered via a nanobubble through a dedicated lumen of the catheter to the artery. In this respect, the catheter can include a suction contact and pressurized release nozzle. The contact area can be held tightly by suction while dispensing pressurized $O_2$ in a cycle. The cyclic $O_2$ can be delivered to induce infarct repair, enhance fibroblast growth and/or angiogenesis.

In one embodiment, the beneficial agent includes a zinc chelator. The zinc chelator can be used to enhance crosslinking and gelation of an infused biomaterial gel in situ.

In another aspect, a biomaterial such as polaxamers, pluronics, PEG-PLLA, and PEG-PLGA di-block or tri-block copolymers may be administered to shield a receptor to prevent $Zn^{2+}$ from causing damage to the infracted area.

Other beneficial agents can include but are not limited to: donor platelets in the presence of stromal cell derived factor lesion and increase the biomaterial uptake in the adjacent tissue. The increased efficacy of biomaterial uptake would enhance attenuation of myocardial remodeling. The term "myocardial remodeling" refers to negative geometric and/or structural changes that the ventricle undergoes, usually following myocardial infarction. Typically this remodeling comprises expansion of the infarct and dilatation of the healthy ventricle segments, resulting in increased wall stress.

The residence time of the beneficial agent can be enhanced by increasing vehicle viscosity with a blood compatible polymer, for example. Suitable blood compatible polymers include hyaluronic acid, polyvinylpyrrolidone (PVP), poloxomers, pluronics, sodium-alginate, polyglutamic acid, polyacrylic acid (PAA), polyethylene glycol (PEG), polyethylene oxide, PEG reactive gels, EDTA-conjugated polyacrylic acid, silk elastin like protein polymer, poly (NIPAAM)-PAA copolymers, albumin, and poly(vinyl alcohol) PVA.

A variety of methods of local delivery of beneficial agent can be employed. The dosing, formulation, and delivery methods may be designed to target a particular function or effect. In this respect, design choices may influence local pharmacokinetics (e.g., $C_{max}$, $T_{1/2}$, AUC, etc.), rate of blood reagent inflow into tissue, microcirculatory obstruction, vessel contact area, and vessel contact proximity and force. For example, parameters such as beneficial agent selection, dosing regimen, formulation, balloon inflation/deflation algorithm, balloon shape, balloon surface, balloon material, and sequence of delivery can be chosen to achieve a desired result.

Balloon Shape Parameter

For example, the balloon shape can be designed to avoid contact with the blood vessel wall during inflation. In this manner, the locally delivered beneficial agent can flow between the surface of the balloon and the blood vessel wall such that the rate of blood reagent inflow into the myocardium would be controlled. The effect of shape includes (1) minimizing contact during occlusion, and (2) modulating the flow rate in a manner to allow flow (seeping or creeping) but not perfusion. In one embodiment, the balloon shape parameter includes a balloon having greater degrees of curvature, i.e., low surface to volume ratio, such as but not limited to a spherical balloon. The balloon surface can include gel coatings, surfactant coatings, or coated to achieve desired design parameters such as vessel contact and increased force against the vessel wall. In this respect, a gel coated balloon surface may be chosen to design to provide greater contact against the vessel wall during delivery of the beneficial agent.

Algorithm Parameter

The inflation deflation algorithm can be chosen from algorithms including saw-tooth, beveled saw-tooth, rectified sine wave, for example. The dosing rate can be constant, for example during both inflation and deflation cycles of mechanical postconditioning, monotonically increasing or monotonically decreasing. In one embodiment, the flow rate is controlled, for example, flow rate off, gradually on, gradually off, then gradually on.

Beneficial Agent Vehicle

The beneficial agent formulation can be a buffered saline vehicle or alternatively, the vehicle can include a viscosity modifier, suspension, liposomes, micelles, nanoparticles, microspheres, or biomaterial.

The delivery of beneficial agent can be achieved by a variety of methods including coated balloon, needle balloon, perfusion balloon, infusion lumen in the reperfusion device, for example. In one embodiment, the reperfusion device is designed with a lumen adapted to locally deliver the beneficial agent distal to the occlusion or lesion in the blood vessel.

Efficacy Studies

An evaluation of acute efficacy of percutaneous post-ischemic conditioning in coronary arteries of swine following induced 90 minutes of ischemia was conducted. Nonatherosclerotic swine models were chosen because porcine and human arteries have correlatively similar anatomy and the porcine model is recommended for use in preclinical studies by the FDA and Schwartz et al. Preclinical Evaluation of Drug-Eluting Stents for Peripheral Applications Recommendations From an Expert Consensus Group, *Circulation,* 2004; 110:2498-2505. The animals had the following model description:

| Species | *Sus scrofa* |
|---|---|
| Strain | Hybrid farm pig (Landrace-Yorkshire) |
| Condition | Non-diseased |
| Source | Ferme Triporc, Inc. |
| Age | Young adult (10 to 16 weeks) |
| Weight at implant | 35 ± 10 kg |

-continued

| Species | *Sus scrofa* |
|---|---|
| Sex | Female |
| Number | 39 and 6 spares |

In the study, the animals received antiplatelet therapy to prevent or reduce the occurrence of thrombotic events. The animals received oral acetylsalicylic acid (325 mg) and clopidogrel (300 mg initial dose and 75 mg subsequently) daily at least three days before intervention. Prior to the procedure, the animals were tranquilized with midazolam 0.4 mg/kg IM and 5 to 1 minutes later with ketamine 20 mg/kg and atropine 0.04 mg/kg administered IM. Upon induction of light anesthesia animals were intubated and supported with mechanical ventilation. Anesthesia was achieved with IV continuous/intermittent infusion of propofol 4 mg/kg/hour and fentanyl 0.004 mg/kg/hour (in 5% dextrose solution). Midazolam was administered at a dose of 0.1 mg/kg every 15 minutes. Isoflurane was administered only if needed and in low quantity to maintain surgical plane of anesthesia.

After anesthesia induction, the left or right femoral artery was accessed through an inguinal skin incision. Bupivacaine was administered IM to manage pain during surgery. A guide catheter was placed in a sheath and advanced into the left coronary arterial ostium under fluoroscopic guidance. A coronary guidewire was inserted through the guide catheters and advanced into the left anterior descending artery (LAD). The balloon was advanced along the guidewire until the balloon was distal to the second diagonal branch of the LAD. The balloon was inflated to pressure sufficient to occlude the coronary artery fully (1:1:1 size ratio). Contrast angiography was used to verify that the LAD was fully occluded. The balloon was inflated for 90 minutes and the animals were observed for reperfusion period of two ours.

Immediately after completion of reperfusion, postconditioning was performed using an embodiment of the system described herein. The device was introduced into the coronary artery by advancing the balloon catheter through the guide catheter and over the guidewire to the deployment site. The one touch actuator switch was deployed and balloon inflation lasted 30±3 seconds. After the inflation period, the balloon was deflated and patency of the vessel was confirmed by contrast injection (TIMI flow evaluation). During the 30±3 seconds of inflation, calpain inhibitor was administered at a dosage of 1 mg/kg. Following the 30±3 seconds of balloon deflation, the balloon was inflated for another cycle of 30 seconds. The cycles were repeated until eight rounds of 30 seconds inflation/deflation were completed. After which the delivery device was removed.

Figure 3:
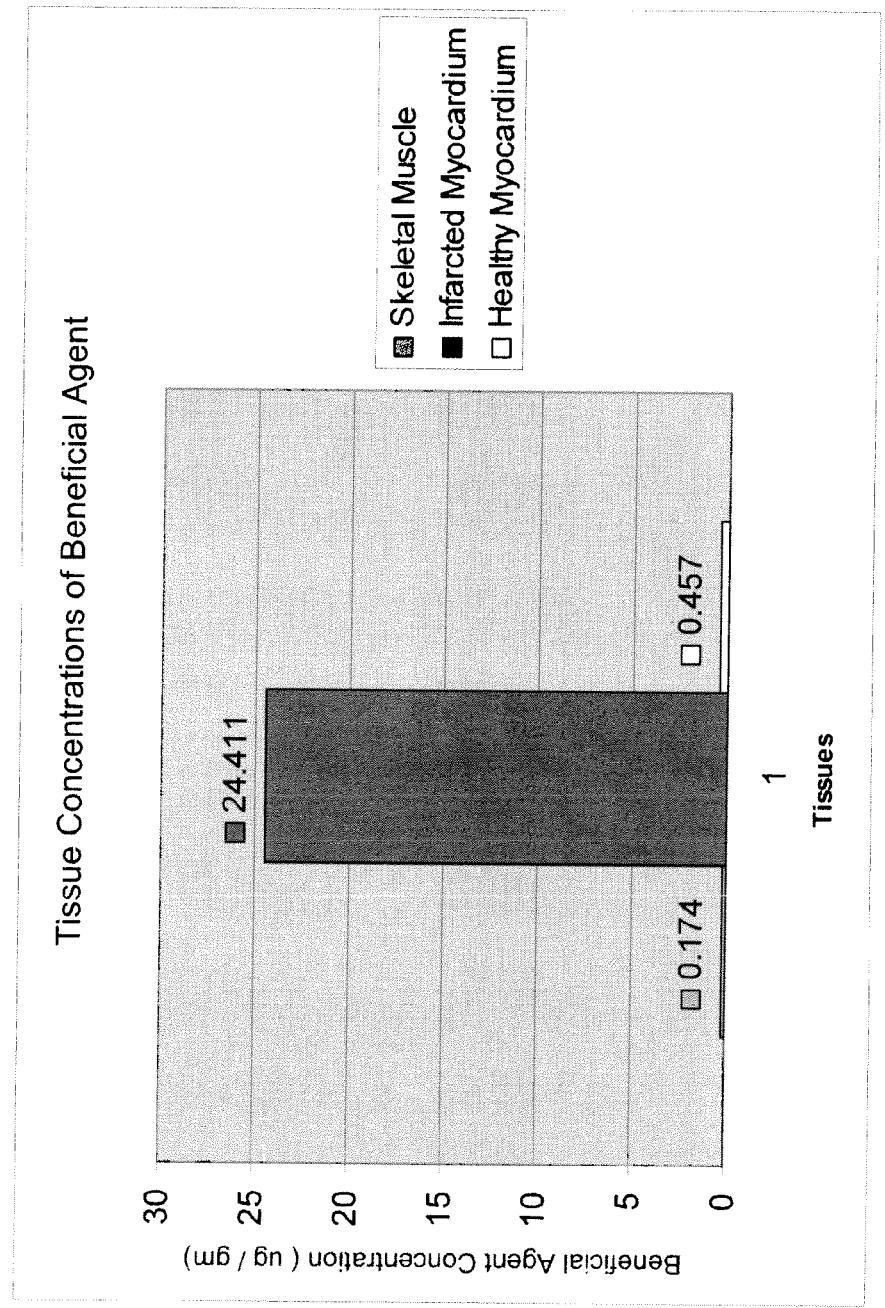
FIG. 3 is a graph illustrating results of a comparative study of tissue uptake of beneficial agent in various tissues, in accordance with the disclosed subject matter.

Referring to FIG. 3 the local delivery of calpain inhibitor during postconditioning resulted on average with a forty-fold increase in tissue uptake of beneficial agent at the infarcted tissue, as compared to beneficial agent uptake at the skeletal muscle and at healthy tissue. The beneficial agent concentration in the infarcted myocardium was 24.411 µg/gm, whereas the skeletal muscle had 0.174 µg/gm and the healthy myocardium has 0.457 µg/gm. It is believed that the increased residence time of the beneficial agent and the distal stasis creates a convection that results in a significantly higher uptake of beneficial agent from the methods described herein.

TABLE 1

| Pig # | Skeletal Muscle Conc. (µg/g)* | Infarcted Myocardium Conc. (µg/g)* | Healthy Myocardium Conc. (µg/g)* | All drug delivery studies fold increase (infarcted/healthy) | low drug delivery fold increase (infarcted/healthy) | high drug delivery fold increase (infarcted/healthy) |
|---|---|---|---|---|---|---|
| 1 | <LOQ* | <LOQ | <LOQ | | | |
| 3 | <LOQ | <LOQ | <LOQ | | | |
| 4 | <LOQ | <LOQ | <LOQ | | | |
| 6 | 0.208 | 11.6 | 0.292 | 39.72603 | | 39.72603 |
| 7 | <LOQ | <LOQ | <LOQ | | | |
| 8 | <LOQ | <LOQ | <LOQ | | | |
| 9 | <LOQ | <LOQ | <LOQ | | | |
| 10 | <LOQ | <LOQ | <LOQ | | | |
| 11 | 0.424 | 42.2 | 0.292 | 144.5205 | | 144.5205 |
| 16 | 0.117 | 129 | 1.43 | 90.20979 | | 90.20979 |
| 17 | <LOQ | <LOQ | <LOQ | | | |
| 18 | 0.131 | 1.74 | 0.308 | 5.649351 | 5.649 | |
| 19 | <LOQ | <LOQ | <LOQ | | | |
| 20 | 0.104 | 20.4 | 0.160 | 127.5 | | 127.5 |
| 21 | <LOQ | <LOQ | <LOQ | | | |
| 22 | 0.097 | 17.2 | 0.137 | 125.5474 | | 125.5474 |
| 24 | <LOQ | <LOQ | <LOQ | | | |
| 25 | <LOQ | <LOQ | <LOQ | | | |
| 26 | 0.084 | 2.65 | 0.316 | 8.386076 | 8.386 | |
| 27 | <LOQ | <LOQ | <LOQ | | | |
| 28 | 0.370 | 2.55 | 0.417 | 6.115108 | 6.115 | |
| 30 | <LOQ | <LOQ | <LOQ | | | |
| 31 | <LOQ | <LOQ | <LOQ | | | |
| 32 | 0.153 | 2.35 | 0.355 | 6.619718 | 6.62 | |
| 33 | <LOQ | <LOQ | <LOQ | | | |
| 36 | <LOQ | <LOQ | <LOQ | | | |
| 37 | 0.158 | 30.3 | 0.300 | 101 | | 101 |
| 38 | <LOQ | <LOQ | <LOQ | | | |
| 39 | <LOQ | <LOQ | <LOQ | | | |
| 42 | 0.202 | 5.42 | 1.20 | 4.516667 | 4.517 | |
| 43 | <LOQ | <LOQ | <LOQ | | | |
| 44 | 0.187 | 3.61 | 0.090 | 40.11111 | 40.11111 | |
| 45 | <LOQ | <LOQ | <LOQ | | | |
| 46 | <LOQ | <LOQ | <LOQ | | | |
| 47 | 0.182 | 3.79 | <LOQ | | | |
| 48 | <LOQ | <LOQ | <LOQ | | | |
| 49 | <LOQ | <LOQ | <LOQ | | | |
| 50 | <LOQ | <LOQ | <LOQ | | | |
| mean | 0.174 | 24.411 | 0.457 | 68.814 | 6.507 | 95.516 |
| std | 0.093 | 37.015 | 0.463 | 54.987 | 1.937 | 41.966 |

*LOQ = limit of quantification

Table 1 above is a chart showing the concentrations in µg/gm of calpain inhibitor detected in the infarcted tissue/healthy tissue of the subjects. The results surprisingly show an increase in uptake of calpain inhibitor of over 144-fold (pig 11) and even the lowest increase still resulted in a 4.5-fold increase (pig 42) skeletal muscle, infarcted tissue, and healthy tissue.

Figure 4:
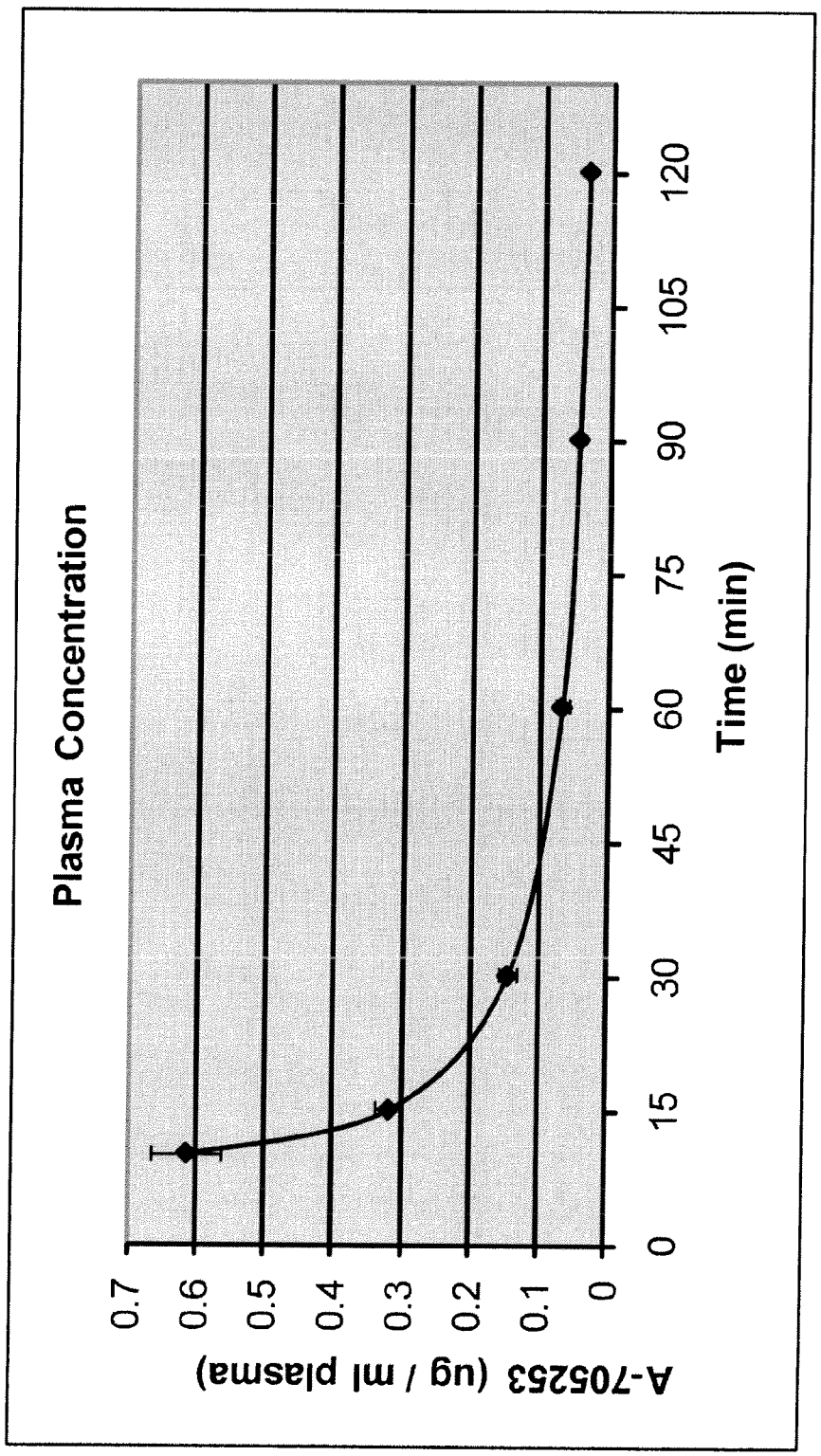
FIG. 4 is a graph illustrating plasma concentrations of beneficial agent after postconditioning in accordance with the disclosed subject matter.

FIG. 4 shows a graph of the blood plasma concentrations detected at time 15 minutes, 30 minutes, 60 minutes, 90 minutes and 120 minutes after local delivery to the vessel during postconditioning procedures. As illustrated, the concentrations of calpain inhibitor remained in the blood plasma at levels of 0.0356 µg/ml even two hours after the procedure. Table 2 below is chart showing the blood plasma concentrations of calpain inhibitor in µg/ml detected in the pigs at time, 5, 10, 15, 30, 60, 90, and 120. As illustrated, the mean concentration of beneficial agent decreased over the time period but remained in significant concentrations of 0.615 ug/ml at 10 minutes, 0.318 ug/ml at 15 minutes, 0.145 ug/ml at 30 minutes, 0.069 ug/ml at 60 minutes, 0.0469 at 90 minutes, and 0.0356 at 120 minutes.

TABLE 2

| Plasma concentrations reported in µg/ml | | | | | | | | |
|---|---|---|---|---|---|---|---|---|
| Pig # | 0 min | 5 min | 10 min | 15 min | 30 min | 60 min | 90 min | 120 min |
| 5 | 0.00 | 1.16 | 0.595 | 0.376 | 0.166 | 0.071 | 0.0404 | 0.0294 |
| 6 | 0.00 | N/A | 0.445 | 0.258 | 0.105 | 0.056 | 0.0388 | 0.0325 |
| 11 | 0.00 | N/A | 0.632 | 0.278 | 0.174 | 0.088 | 0.0649 | 0.0509 |
| 16 | 0.00 | N/A | 0.393 | 0.168 | 0.113 | 0.061 | 0.0432 | 0.0315 |
| 18 | 0.00 | N/A | 0.804 | 0.389 | 0.152 | 0.070 | 0.0460 | 0.0351 |
| 20 | 0.00 | N/A | 0.459 | 0.214 | 0.075 | 0.033 | 0.0225 | 0.0165 |
| 22 | 0.00 | N/A | 0.753 | 0.424 | 0.146 | 0.064 | 0.0436 | 0.0433 |
| 26 | 0.00 | N/A | 0.813 | 0.438 | 0.256 | 0.100 | 0.0616 | 0.0414 |

TABLE 2-continued

| | Plasma concentrations reported in µg/ml | | | | | | | |
|---|---|---|---|---|---|---|---|---|
| Pig # | 0 min | 5 min | 10 min | 15 min | 30 min | 60 min | 90 min | 120 min |
| 28 | 0.00 | N/A | 0.661 | 0.192 | 0.116 | 0.070 | 0.0505 | 0.0379 |
| 32 | 0.00 | N/A | 0.530 | 0.334 | 0.086 | 0.050 | 0.0305 | 0.0267 |
| 37 | 0.00 | N/A | 0.387 | 0.256 | 0.154 | 0.073 | 0.0554 | 0.0393 |
| 42 | 0.00 | N/A | 0.545 | 0.275 | 0.109 | 0.057 | 0.0452 | 0.0335 |
| 44 | 0.00 | N/A | 0.946 | 0.477 | 0.221 | 0.104 | 0.0668 | 0.0457 |
| 47 | 0.00 | N/A | 0.643 | 0.373 | 0.162 | 0.070 | 0.0472 | 0.0351 |
| Mean | | | 0.615 | 0.318 | 0.145 | 0.069 | 0.0469 | 0.0356 |
| SD | | | 0.170 | 0.097 | 0.050 | 0.019 | 0.0125 | 0.0086 |
| SEM | | | 0.045 | 0.026 | 0.013 | 0.005 | 0.0033 | 0.0023 |
| time (min) | 0 | 5 | 10 | 15 | 30 | 60 | 90 | 120 |

Pig #5 had a 5 minute sample and the rest of the pigs did not.

Figure 5:
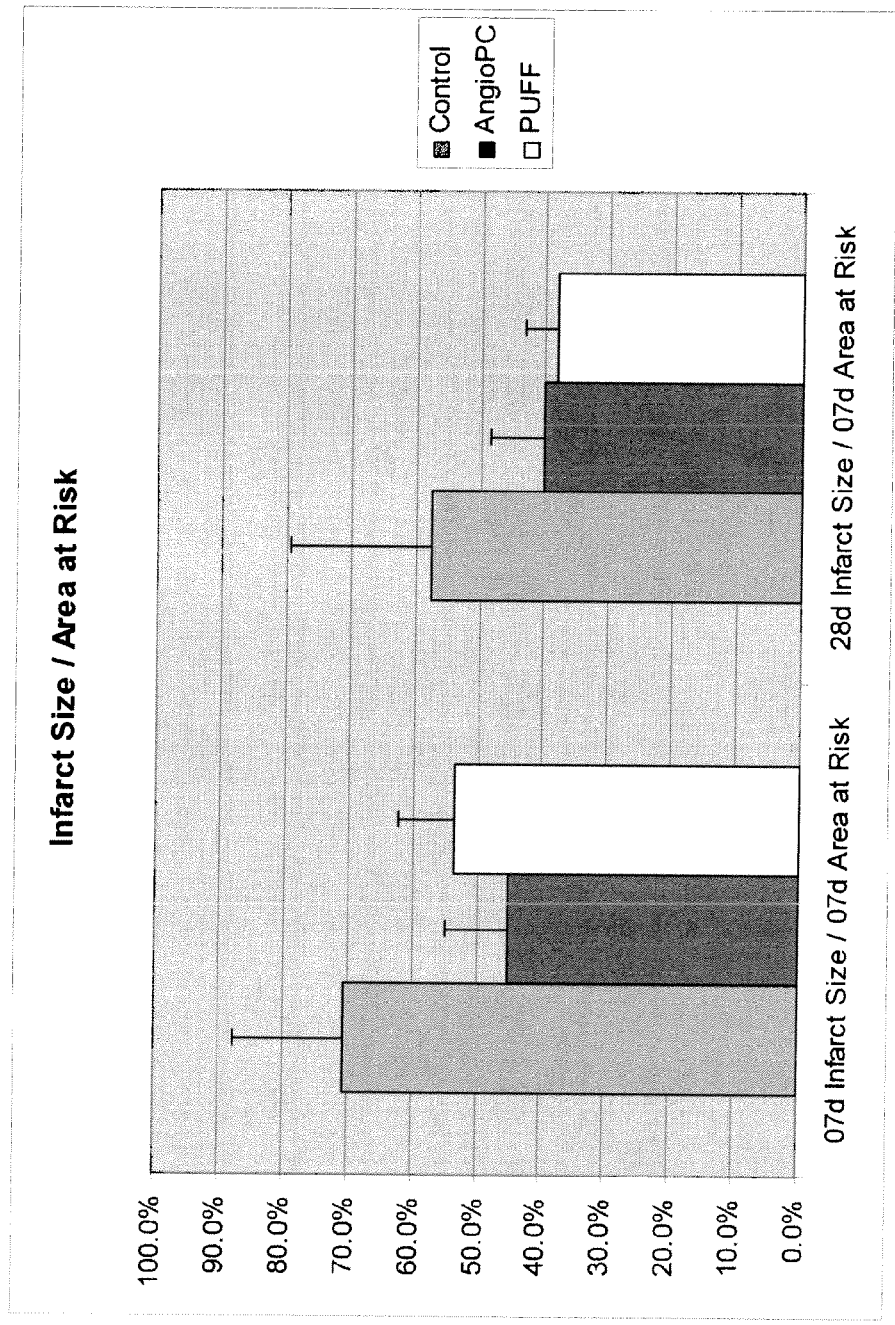
FIG. 5 is a graphical presentation of a comparison of ratios of infarct size to area at risk, in accordance with the disclosed subject matter.

FIG. 5 illustrates a comparison of infarct size/area at risk ratio between three different sample sets tested: (1) a "Control" group wherein no postconditioning was performed; (2) an "AngioPC" group in which postconditioning was performed using a conventional angioplasty catheter; and (3) "PUFF" group in which postconditioing procedures were performed using the "PUFF" reperfusion system described and embodied herein. The graph depicts the ratio of infarct size with respect to the area at risk (i.e. downstream of the infarct) at seven days and at twenty-eight days for each of the groups. Area-at-risk was determined by T2w-STIR, a known methodology to determine the amount of water (edema) inside the heart.

As illustrated, postconditioning using both the conventional angioplasty catheter and the "PUFF" system provides a significant advantage over the "Control" group (i.e. no postconditioning performed) at both seven and twenty-eight days. The control group exhibited an infarct size/area of risk of about 70% at day 7 and about 58% at day 28, whereas the AngioPC group exhibited an infarct size/area of risk ratio of about 45% at day 7, and 40% at day 28, and the PUFF group exhibited an infarct size/area of risk ratio of about 53% at day 7 and 38% at day 28. Accordingly, over time the postconditioning with the PUFF system provides improved mitigation and reduction in reperfusion injury than does postconditioning using a conventional angioplasty catheter.

In addition to improved infarct area/area at risk, postconditioning procedures using the PUFF system exhibits an improved Ejection Fraction over the nonpostconditioning, and postconditioning using a conventional angioplasty catheter. "Ejection fraction" refers to the percentage of blood that is pumped out of a filled ventricles with each heart beat. The volume of blood within a ventricle immediately before a contraction is known as the end-diastolic volume. The volume of blood left in a ventricle at the end of contraction is end-systolic volume. The difference between end-diastolic and end-systolic volumes is the stroke volume, or the volume of blood ejected with each beat. Accordingly, the ejection fraction is the stroke volume divided by end-diastolic volume. A normal LV ejection fraction is 55 to 70 percent.

Figure 6:
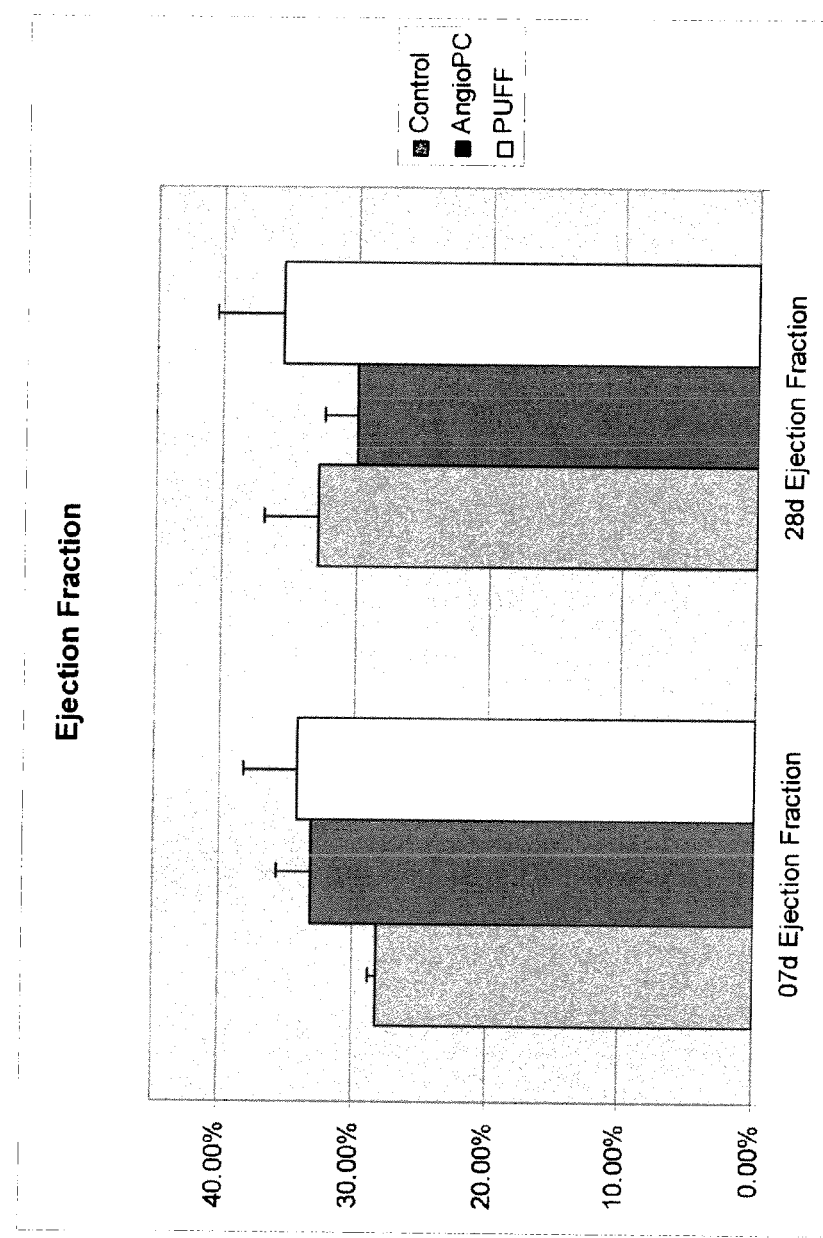
FIG. 6 is a graphical presentation of a comparison of ejection fractions, in accordance with the disclosed subject matter.

FIG. 6 is a graph that illustrates the results from a comparison study of the ejection fraction after an ischemic event and postconditioning by a conventional angioplasty catheter and the PUFF reperfusion catheter, as compared to the "Control" group, in which no postconditioning was performed. As depicted in the graph, after seven days, the subjects treated in accordance with postconditioning using the reperfusion system of the present disclosure, i.e. "PUFF", demonstrated statistically improved ejection fraction as compared to both the "Control" and "AngioPC" groups. In this regard, the ejection fraction after 7 days was closer to the normal ejection fraction of 55%-70% than either of the other groups. Furthermore, this improvement was maintained, and indeed increased in comparison to the "AngioPC" group, in Ejection Fraction measurements taken at 28 days. Without being held to any theory, it is believed that the angioplasty catheter may have damaged the vascular wall to cause a reduction in the ejection fraction over time, whereas the "PUFF" group surprisingly demonstrated an increase in ejection fraction over time.

In accordance with another aspect of the present disclosure, the inflation and deflation of the balloon can be controlled via a trigger or button as described above. This is advantageous in that it allows for rapid occlusion and de-occlusion, and thus shorter reperfusion cycle times. FIG. 16 illustrates a comparison of the inflation and deflation times for the apparatus of the present disclosure ("PUFF") and a conventional angioplasty device ("AngioPC"). As depicted, the apparatus of the present disclosure greatly reduces the time required to both inflate and deflate the balloon. Inflation of the angioplasty catheter is about 4.84 seconds compared with the present catheter device, which is about 0.50 seconds. The deflation results demonstrate that it takes at least 6.81 seconds for the angioplasty catheter to deflate, whereas the PUFF catheter deflates in about 1.0 second.

II. Catheter Overview

In accordance with the subject matter, a catheter system is configured to permit sequential, such as intermittent and repeated, inflation and deflation of an expandable member, such as a balloon. In some embodiments, the sequential inflation and deflation of the balloon is achieved by single-touch actuation. The term "single-touch" as used herein means that actuation of inflation and deflation of the expandable member can be achieved by a single switch, single button, or other single point of actuation. In this regard, the user simply presses or otherwise actuates an actuator to inflate the balloon, and presses it again to actuate deflation of the balloon. Thus, unlike the conventional angioplasty catheter that generally requires sizing, prepping, and inflating by rotation of a screw on the indeflator, one embodiment of the present system avails itself of quick use without the need for preparation.

A step by step comparison shows that while an angioplasty balloon catheter requires many steps to size, prep, remove air bubbles and use the device, a catheter system in accordance with an embodiment of the present system is much more efficient, thereby providing a shorter procedure time and reduced risk to the patient. Thus, the system described herein leads to step reduction for postconditioning that ultimately save lives by saving time where time is a critical factor for survival.

| Steps | Typical Angioplasty System | One Embodiment of the System |
|---|---|---|
| 1. | Size vessel proximal to lesion | Get package containing system |
| 2. | Determine size of balloon needed | Open Box containing system |
| 3. | Get Box(s) | Unwrap Product |
| 4. | Look Up Compliance Chart | Engage Pressure |
| 5. | Choose final size | Advance to target lesion over guidewire |
| 6. | Open box containing angioplasty system | Flip switch On (no purge required, no air bubbles if carbon dioxide fluid used) |
| 7. | Unwrap product | Flip switch off |
| 8. | Purge Indeflator | Repeat steps 6 and 7 to sequentially inflate and deflate |
| 9. | Connect Balloon to Indeflator | |
| 10. | Prep Balloon (1st time = 3 steps) | |
| 11. | Prep Balloon (2nd time = 3 steps) | |
| 12. | Confirm no air bubbles | |
| 13. | Advance to target lesion | |
| 14. | Lock Indeflator | |
| 15. | Twist handle while watching dial until target pressure diameter curve is reached (about 8 atm) | |
| 16. | After 30 seconds, unlock Indeflator | |
| 17. | Pull vacuum | |
| 18. | Repeat steps 14-17, repeat prep balloon if bubbles seen | |

A conventional rapid exchange angioplasty balloon catheter has no means to deliver a beneficial agent, such as a drug, distal to the balloon of the balloon catheter body, without the added steps of removing the rapid exchange catheter from the body of the patient, introducing an over-the-wire balloon catheter to deliver the beneficial agent distal to the balloon, and then replacing the rapid exchange balloon catheter again.

Further, although an over-the-wire balloon catheter may be able to occlude blood flow and deliver material distal to the distal end of the catheter body, the catheter embodied herein, provides advantages. The use of rapid exchange length wires is most prevalent. The catheter of the present invention is capable of being used with no time lost to switching guide wires. Switching guide wires (RX to OTW) takes time. The present catheter device allows the operator to leave the guide wire in place, whereas an OTW catheter design requires the physician to change and possibly disturb the location of the guide wires. Thus, even if the OTW catheter is capable of delivering beneficial agent distal to the catheter body, time is lost from changing the guide wires. The present catheter system can run over the guide wire, and the balloon can occlude the blood vessel while beneficial agent is delivered to another other areas of the vessel. In one embodiment, the one-size-fits all balloon allows the operator to deliver beneficial agent to locations of the vessel. Also, its ability to conform to the vessel shape, as opposed to the vessel conforming to the balloon shape, allows for use of the catheter in multiple locations and in lumen of multiple sizes to be used in one case. In other devices, if the operator would like to deliver drugs or other compounds during postconditioning, he or she would have to get different sized angioplasty balloons to deliver beneficial agent in different locations of the vessel. In contrast, the catheter described herein allows the catheter to be moved to the other location. Thus, the advantages associated with the reduction in the number of required steps and procedure to use the catheter of the embodiments described herein as compared to conventional rapid exchange or over-the-wire angioplasty balloon catheters is heightened when the catheter is used to deliver a beneficial agent, such as drug or other therapeutic agent. Thus, the time savings advantage of using a rapid exchange catheter is eliminated when one needs to use the catheter to deliver a beneficial agent distal to the balloon. Heretofore, the physician was limited to using an over-the-wire balloon catheter, which does not have the same time savings advantage of the rapid exchange catheter. Accordingly, the system provides benefits of a rapid exchange balloon catheter and an over-the-wire balloon catheter by the capability of deliver a therapeutic agent through the catheter while the catheter is coupled with a rapid exchange guide wire.

In conventional angioplasty techniques, the size and diameter of the balloon must be matched to the size and native diameter of the obstructed segment of the artery to be dilated. If the balloon size and diameter are smaller than the native artery, the results of balloon angioplasty are suboptimal, requiring a second dilation with a larger-sized balloon. In some cases, the result is a failed procedure, which may require either a second separate angioplasty procedure or bypass surgery. If the balloon is oversized in relation to the obstructed segment of the native vessel, the inner wall of the artery may dissect from the remainder of the artery and may occlude the vessel completely, causing total cessation of blood flow to the target area of the myocardium. This complication can lead to acute myocardial infarction and necessitate emergency bypass surgery. If the acute occlusion leads to a large infarction, death is a possibility.

If a patient has a single obstruction in the right or left coronary artery system, a single balloon catheter with a matching diameter and size will be selected for the intended dilation procedure. When the balloon is inflated inside the obstructed segment of the native artery, the balloon should maintain the original preshaped configuration and diameter under the maximum allowed pressure. In single lesion dilations, the choice of a properly-sized balloon catheter is relatively simple, although there are instances in which the original selection of the balloon catheter is inadequate so that a second balloon catheter is necessary to complete the procedure successfully.

However, in multi-vessel disease, balloon catheter selection becomes compounded and complex. For example, a patient may have three lesions in the left coronary artery, and all three lesions may be approachable individually for successful balloon angioplasty. But such lesions may be in vessels of different sizes. With conventional balloon catheters, performing angioplasty in differently-sized lesions is not always impossible, but it is cumbersome and inefficient. For each lesion, a matching balloon catheter is exchanged and manipulated into the target lesion. To do this three consecutive times requires roughly three times the procedure time, three times the contrast amount, and a minimum of three separate balloon catheters and their accessory devices.

In accordance with one aspect of the subject matter described, a more efficient and effective balloon catheter system is provided. In one embodiment, the balloon catheter system is a pre-assembled device having a one-size fits all balloon designed for use within a variety of different vessels, such as coronary, peripheral, spinal, cerebral, so as to provide a device for which the operator need not select a pressure or volume for inflation of the balloon. Accordingly, the physician need not waste time with additional steps required to size and prep the balloon, as required for a conventional angioplasty balloon catheter. Thus, one embodiment of the system provides physicians with an efficient, easy to use catheter designed for rapid, sequential or repeated inflation and deflation of a balloon, such as for reducing or preventing reperfusion injury to an organ or tissue after an ischemic event, such as in postconditioning or other applications.

For applications in which the system is employed for postconditioning applications, the system can be employed to (1) stop blood perfusion to the organ or tissue for an amount of time by inflating the balloon in the blood vessel, and (2) permit perfusion to the organ or tissue for another period of time by deflating the balloon, sequentially repeat the inflation (stop) and deflation (perfuse), and optionally, (3) deliver beneficial agents, e.g., drug, contrast, therapeutic agent, to an area distal to the balloon.

The balloon is configured to occlude a blood vessel during expansion or inflation of the expandable member, and then permit resumption of perfusion of the blood flow during contraction or deflation of an expandable member. The occluded vasculature can include a venous blood vessel as in retroperfusion, or an arterial blood vessel such as in reperfusion. The occluded blood vessels may be from the coronary, peripheral, or cerebral or other vasculature.

As illustrated in the schematic of FIGS. 1A and 1B, in one embodiment postconditioning is achieved by inflating and deflating the balloon proximal to a lesion for one or more cycles of from about 10 to 60 seconds to up to about thirty minutes. In one example, the balloon is inflated and maintained for about 30 seconds, and then the balloon is deflated and maintained deflated for about 30 seconds (FIG. 1). In another embodiment, the balloon is inflated and maintained for less than twenty seconds, and deflated and maintained deflated for about 20 seconds up to about 2 minutes. These cycles are repeated as necessary to perform the postconditioning therapy. A "cycle" as used herein refers to a completed inflation and deflation step. For example, an expandable member is sequentially contracted and expanded such as to permit blood perfusion for about 10 to about 60 seconds or longer and stop perfusion for about 10 to about 60 seconds or longer (e.g., 30 minutes) for a one or more cycles. In some embodiments, the cycles are repeated for about 3 to about 10 cycles or more. Other postconditioning methods can be employed, however, such as postconditioning methods described in U.S. Patent Publication No. 2004/0255956 and 2007/0160645 to Vinten-Johansen et al., the disclosures of which are incorporated herein by reference in their entirety for all purposes.

In some embodiments, the catheter is designed to postcondition a stented blood vessel without changing the dimension of the implanted stent. In this manner, the expandable member is a compliant balloon as described below, which does not negatively affect the implanted stent during postconditioning cycles of inflation and deflation of the balloon. Thus, in accordance with one embodiment, the postconditioining technique occurs within the lumen of an implanted stent.

As illustrated in FIG. 1A, the postconditioning technique can be employed prior to stenting a blood vessel or subsequent to stenting a blood vessel. With regards to postconditioning prior to or after stenting, an embodiment of the system embodied herein is designed such that postconditioning a blood vessel will not dislodge the plaque secured to the blood vessel wall. With regards to postconditioning after stenting, the postconditioning can occur proximal to the stent, distal to the stent, and/or inside the stent. Advantageously, the catheter device embodied herein does not alter the shape or dimension of the deployed stent when postconditioning is employed within the stented vessel. Accordingly, embodiments of the catheter of the subject matter can be used for postconditioning before or after placement of a stent in a blood vessel.

Figure 7:
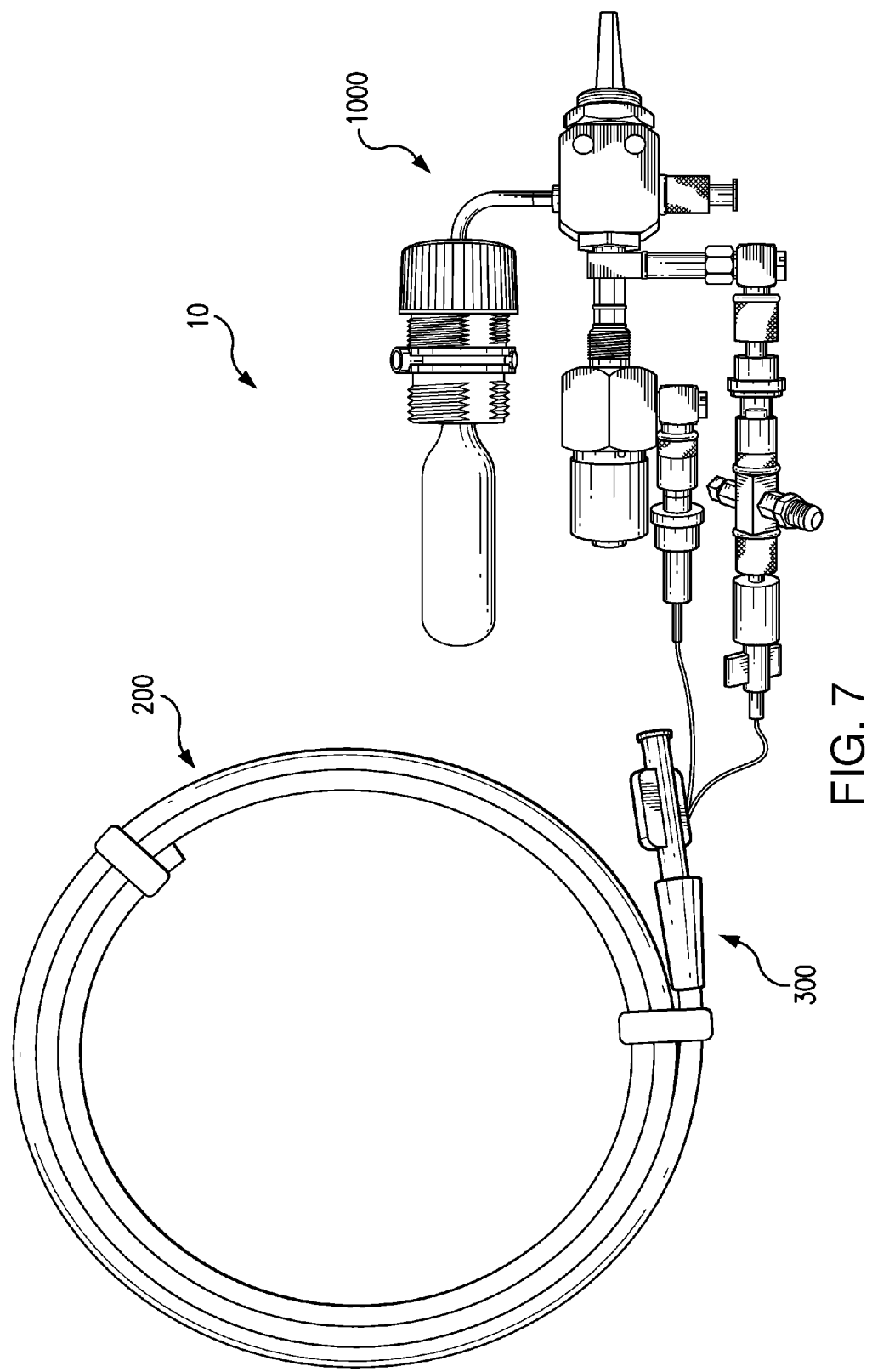
FIGS. 7 and 8 are schematic views of the system in accordance with one embodiment of the disclosed subject matter.

As shown in FIG. 7, the catheter system 10 generally includes a catheter having an elongate shaft 200, an expandable member 300 and a closed fluid circuit including a control system 1000 housed in a handle. The entire closed fluid circuit is disposed within the handle and catheter body.

Figure 8:
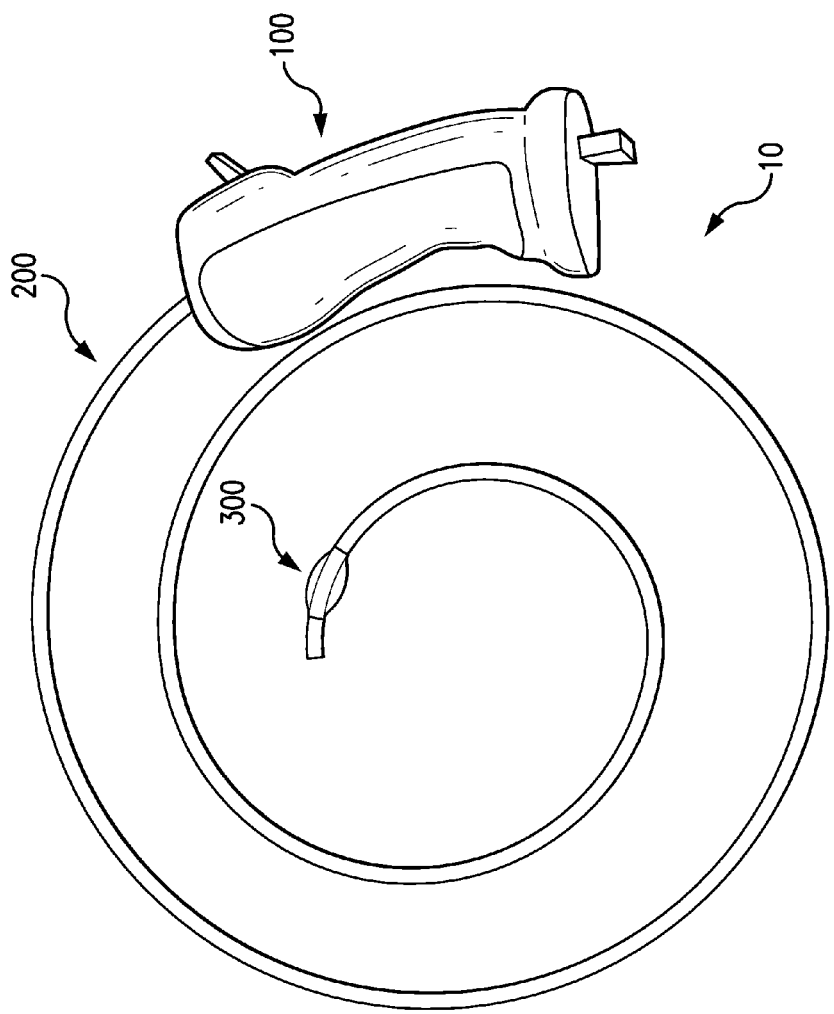

In some embodiments, handle 100 (FIG. 8) is non-removably attached to the catheter system such that a single unitary device is provided. Advantageously, the unitary device is packaged in a ready-to-use state. In other words, the device can be a pre-assembled unit that is ready for use in any size vessel thereby eliminating the need for measuring of the patient and selection of the appropriate size balloon and catheter, as is required in prior art devices. An exemplary embodiment of the pre-assembled unit is illustrated in FIG. 8. Once the device is removed from any packaging provided and coupled with the inflation fluid source, described in further detail below, the device is ready for use. Further, in applications in which a therapeutic agent is delivered, the device of the present subject matter provides for a more efficient procedure in that a rapid exchange guidewire can remain disposed within the lumen of the catheter during delivery of the therapeutic agent. In some embodiments, expandable member 300 is disposed at a distal section of the elongate shaft of the catheter.

The elongate shaft 200 includes at least two lumen, as better seen in FIGS. 9A to 9C. In one embodiment, the at least two lumen include an inflation lumen and a separate dedicated independent deflation lumen. Both the inflation lumen and the independent deflation lumen are in fluid communication with the interior portion of a balloon 300 but generally are not in fluid communication with each other. In this regard, an inflation fluid of any pressurized fluid, such as carbon dioxide, noble gases including helium, neon, and pressurized liquids such as saline or contrast agents, is introduced into the balloon 300 via the inflation lumen to inflate the balloon and then exits the balloon to enter the independent deflation lumen. The flow of inflation fluid is one-way through the fluid circuit. The independent deflation lumen allows for rapid deflation of the balloon and in one embodiment is configured for Venturi-assisted deflation, as described below.

A handle 100 is disposed at or near the proximal end of the catheter and houses the control system 1000 of the fluid circuit (FIGS. 7 and 8). Handle 100 is configured to provide a physician with the ease of automatic, sequential inflation and deflation of expandable member 300 by, in some embodiments, a one-touch actuator 101. In this manner, the one-touch actuator can be a switch, button, lever, or other device adapted to permit a user to inflate expandable member 300 when actuated in a first position or direction, and to deflate expandable member 300 when actuated in a second position or direction. The one-touch actuator has a number of advantages. It allows the operator to easily manipulate the catheter device by the ease of a switch rather than the cumbersome and time consuming operation requirements of a conventional angioplasty catheter. The one switch actuation plus the reduction in steps, and corresponding reduction in time required to conduct postconditioning allows the physician or other interventionalist to focus more of their attention and care on the patient, rather than be preoccupied with an array of steps and device components as required with conventional angioplasty catheters.

Figure 10:
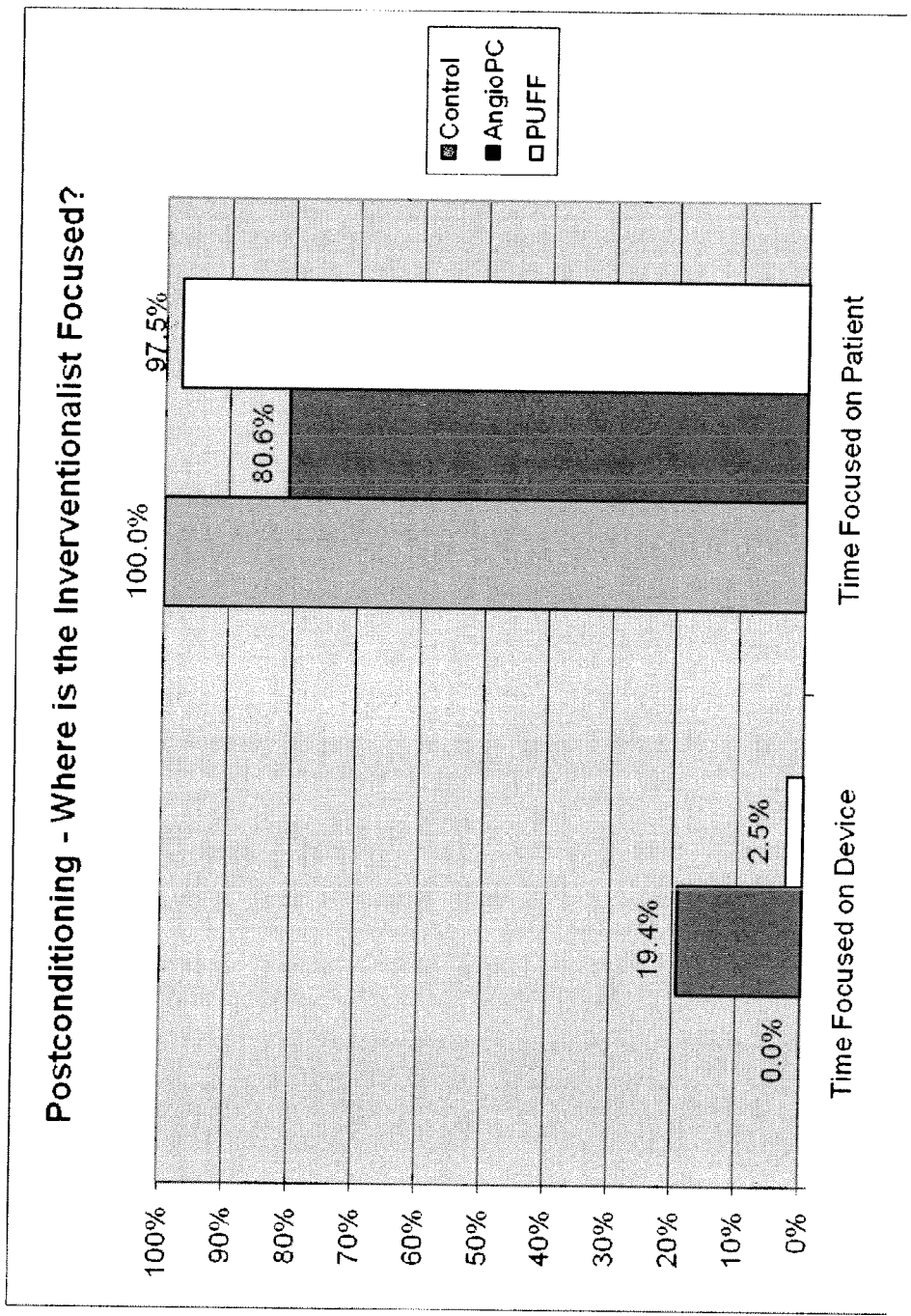
FIG. 10 is a graphical presentation of a comparison of physician/operator focus or attention allocation, in accordance with the disclosed subject matter.

FIG. 10 illustrates a comparison of the demands on the physician/interventionalist attention and focus. The "PUFF" device of the presently disclosed subject matter requires less procedural steps, and provides a pre-assembled device with a trigger operation which result in a greater amount of physician/interventionalist focus on the patient. Moreover, the apparatus of the present disclosure can be operated by a single physician/interventionalist whereas conventional angioplasty devices require two physicians to operate.

The one-touch ease of sequential inflation and deflation of expandable member 300 can be achieved by adapting the catheter shaft to include an independent inflation lumen and separate independent deflation lumen. In some embodiments, the switch is configured such that the user cannot overinflate the expandable member 300. In this regard, the system can include a pulse valve that closes an outlet port to the expandable member when the expandable member is fully inflated thereby preventing over inflation. The fluid circuit needs no electricity or electronics to achieve inflation or deflation of the balloon, or actuation of inflation and deflation or flow of the inflation fluid through the circuit. When the balloon is fully inflated further actuation of the switch does not further inflate the balloon, thereby rendering the system "fool-proof" and effectuating reproducibility with relation to inflation of the expandable member.

In some embodiments, the handle 100 includes a control system 1000 of a closed fluid circuit disposed within the catheter device. The control system 1000 is configured to assist modulation of inflation fluid flow throughout the fluid circuit of the catheter system such as to effectuate inflation and deflation of the expandable member 300. In some embodiments, the fluid circuit and in particular the independent deflation lumen can be configured to induce a Venturi-assisted flow to rapidly deflate expandable member 300, as will be described below.

II. The Catheter Body

In accordance with one embodiment, as shown FIG. 9A, the catheter includes a generally elongate tubular shaft 200 having a proximal shaft segment 201 and a distal shaft segment 202 in fluid communication. Proximal shaft segment 201 and distal shaft segment 202 can be formed from material having the same or similar hardness or durometer to provide a uniform flexibility along the catheter body. Alternatively, the proximal shaft segment and distal shaft segment can be formed from materials having different flexibilities to provide a catheter having a varied flexibility along a length thereof. For example but not limitation, the proximal shaft segment may be formed from a hypotube and the distal shaft can be formed from a polymeric material to provide increased flexibility along the catheter tubular shaft. As such, the proximal shaft and distal shaft segments can be formed from the same tube or alternatively can be two separate tubes connected or welded together to form a unitary tube. The catheter may comprise one or more polymers or polymer blends having different stiffness.

Figure 11:
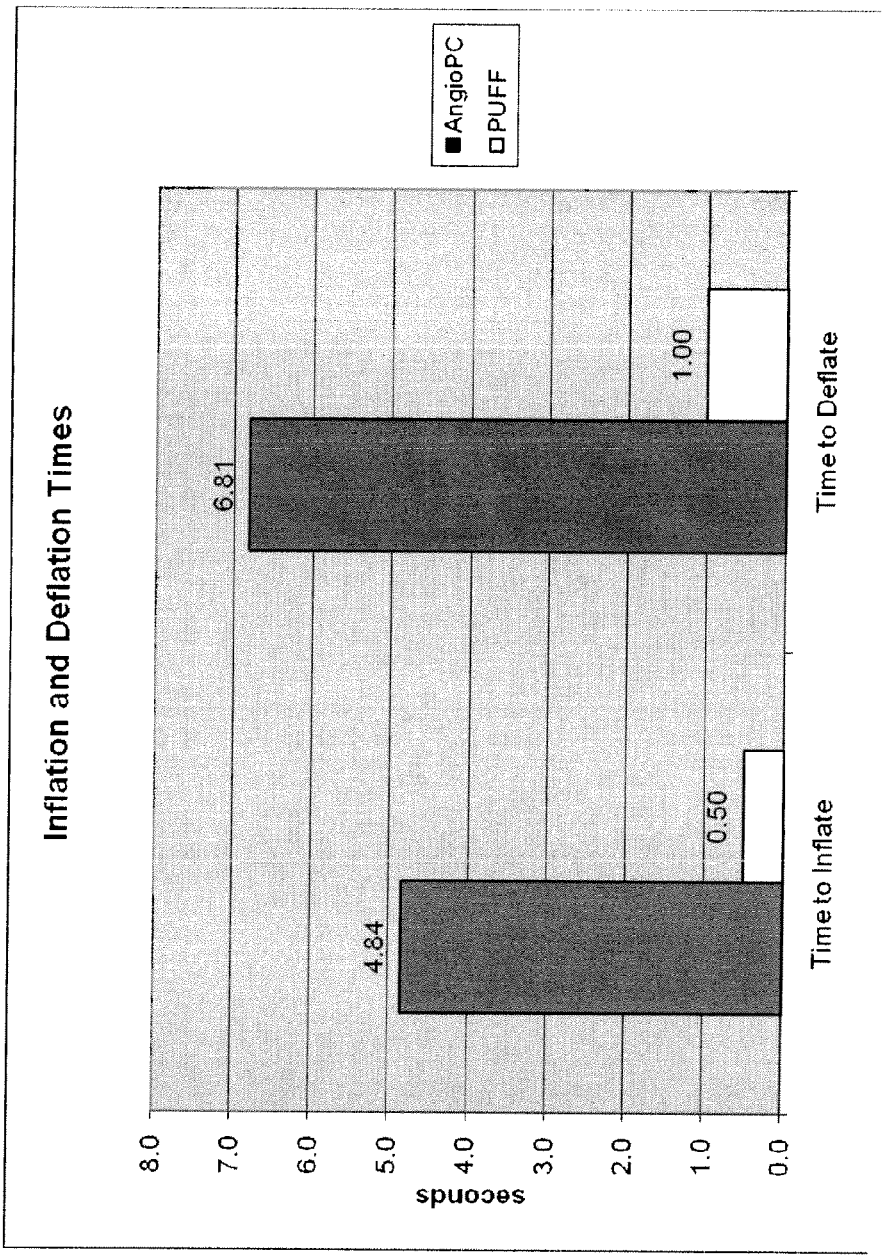
FIG. 11 is a graph illustrating the results from a comparison study of inflation and deflation times, in accordance with the disclosed subject matter.

As illustrated in FIG. 9B, elongate shaft 200, in one embodiment, includes an independent inflation lumen 203 configured to provide a passage or flow of inflation fluid to an expandable member 300 disposed at or near the distal end 202 of the catheter shaft. Elongate shaft 200 can also include an independent deflation lumen 204 to provide a second fluid flow passage for the inflation fluid to outflow from expandable member 300 during deflation. In this manner, the sequential inflation and deflation of expandable member 300, and consequential stopping and starting of blood flow during postconditioning techniques can be efficient and rapid. For example, in one embodiment of the system, the expandable member 300 can be inflated in five seconds or less, preferably one second or less, most preferably in $1/15$th of a second or less. Further, the expandable member can be deflated in five seconds or less, and preferably three seconds or less, most preferably $1/4$ of a second or less. This rapid inflation and deflation of the expandable member provides advantages for postconditioning techniques not available through use of the conventional angioplasty catheter. As illustrated in FIG. 11, a comparison study was performed to compare the inflation and deflation times of a conventional angioplasty catheter and a catheter system of the present disclosure. As shown in the graph, the angioplasty catheter required nearly five seconds (4.81 s) to inflate while the catheter system of the present subject matter required only one-half second. Thus, the catheter of the present disclosure inflated nearly ten times quicker than did the angioplasty catheter. The results were similar when comparing the deflation time required for both the angioplasty catheter and the catheter of the present subject matter. The angioplasty catheter required nearly seven seconds (6.81 s) to deflate while the PUFF catheter deflated in one second. Accordingly, for an eight cycle postconditioning technique, the angioplasty catheter requires over ninety-three seconds (11.65 s per one inflation/deflation cycle) to complete whereas the PUFF catheter design completes the cycles in only twelve seconds (1.5 s per one inflation/deflation cycle). The catheter system described herein exhibits rapid, efficient inflation and deflation cycles and can optimize postconditioning.

The elongate shaft 200 can be formed in a number of shapes, for example, in one embodiment, the shaft can have a tubular configuration as shown in FIG. 9B. However, as would be known in the art other shapes can be employed, such as elliptical.

The elongate shaft 200 can further include guidewire lumen 205, for example, in addition to the inflation and deflation lumen. In this regard, guidewire lumen 205 can be configured to extend from a tip 400 at the distal end of elongate shaft 200 to a more proximal location of the elongate shaft 200 to provide an over-the-wire catheter. Alternatively, elongate shaft 200 may be formed to have a notch (not shown) disposed at a location between the distal end 202 and proximal end 201 of elongate shaft 200 to provide a rapid exchange catheter.

In accordance with another embodiment, elongate shaft 200 can further include a drug delivery lumen 206, such as for example, a drug infusion lumen configured to locally deliver beneficial agents such as those described above or other agents. In one embodiment, the beneficial agents are locally delivered to an area of a ischemic event. In other embodiments, the catheter lacks a drug delivery lumen and instead, a drug coated balloon is disposed on the catheter shaft for local delivery of a beneficial agent.

In some embodiments, the elongate shaft 200 includes four separate and independent lumen (e.g., inflation lumen 203, deflation lumen 204, guidewire lumen 205, and drug delivery lumen 206). However, other configurations can be employed. In some embodiments, the diameters of the lumen have different sizes. For example, in some embodiments, the deflation lumen has a diameter of about twice the size of the inflation lumen diameter. In one embodiment, as depicted in FIG. 9C, the diameter of the inflation lumen $203d$ is about 0.100 mm, the diameter of the deflation lumen $204d$ is about 0.200 mm, the diameter of the guidewire lumen $205d$ is about 0.400 mm, and the diameter of the infusion lumen $206d$ is about 0.300 mm. Accordingly, each lumen can be configured to have a different sized diameter, if desired.

Figure 12B:
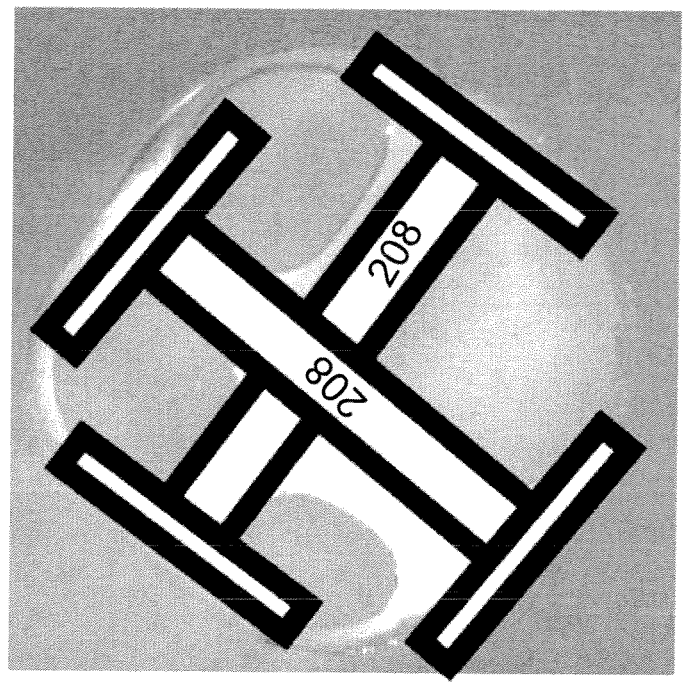
FIGS. 12A and 12B are cross sectional views of the catheter shaft in accordance with one embodiment of the disclosed subject matter.
Figure 12A:
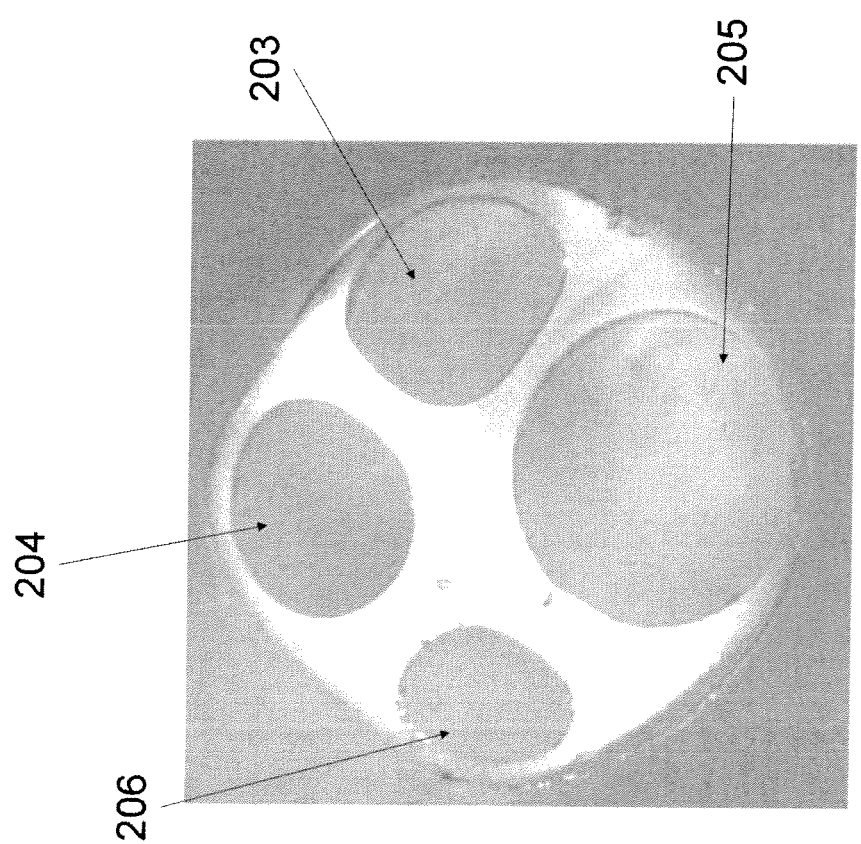

In some embodiments, as illustrated in FIGS. 12A and 12B, elongate shaft 200 can be formed from a single extrusion with a plurality of lumen, e.g., the four lumen as described above. As further shown, the four lumen can be oriented within the extrusion so that the extruded polymeric web 208 remaining between the lumen forms an "I-beam" cross section. The I-beam configuration allows an increase in strength to facilitate catheter tracking thought the vasculature without the need for multiple single tubes and/or braiding on the shaft. In some embodiments, the I-beam configuration can be made to have equal strength as a braided shaft and have a lower profile than a braided catheter shaft. Thus, the I-beam configuration as depicted in FIG. 12B allows for a smaller overall catheter, and multiple dedicated lumen to be within the catheter body.

An I-beam configuration provides efficient form for resisting both bending and shear in the plane of the polymeric web 208. In this manner, the plurality of lumen 203, 204, 205, 206 are configured as independent lumen physically spaced from one another by polymeric web 208 disposed therebetween. One advantage of the I-beam shape is that the catheter shaft is more resistant to bending when the catheter is pulled in a particular direction.

In some embodiments, the different sized lumen are arranged or oriented within the extrusion to form a pattern such that the largest sized lumen 205 is proximate each of the smaller sized lumen 203, 204, 206, as depicted in FIGS. 9B and 9C, such that the polymeric web 208 disposed between the lumen 203, 204 and 205 forms the I-beam pattern, as illustrated in FIGS. 12A and 12B. In some embodiments, the thickness of extruded polymeric web 208 is substantially equivalent to the bending moment of the shaft. A bending moment exists in a structural element when a moment is applied to the element so that the element bends. Moments and torques are generally measured as a force multiplied by a distance so they have as unit newton-meters (N·m), or foot-pounds force (ft-lbf). In this manner, it is believed that the elongate shaft 200 will resist bending equally, regardless of the direction of the bend to the catheter shaft. It is further believed that a catheter shaft without these features will bend to a different degree depending upon the orientation inside the vessel.

Elongate shaft 200 can further include a distal tip 400 (FIG. 9A) having a proximal end abutting or overlapping the distal end 202 of the catheter body. In one embodiment, catheter tip 400 includes one or more lumen. For example, in one embodiment, the tip 400 can include a first lumen aligned with guidewire lumen 205 of elongate shaft 200, and a second lumen aligned with infusion lumen 206. The guidewire lumen 205 is aligned with a lumen through the catheter tip 400 disposed at the distal end of the catheter shaft 202. These aligned lumens permit the catheter to ride over a guidewire. Furthermore, once properly inserted, the guidewire can be removed and fluid can be passed through the lumen.

In one embodiment, the tip 400 can be formed of a material softer than the material of the catheter such that the tip has sufficient column strength to resist buckling during insertion, but is sufficiently flexible to deform when the tip is subjected to axial or radial loads in the body in the absence of the guidewire. Catheter elongate shaft 200 is configured to enable the passage and the longitudinal translation of guidewire within lumen 205 during a surgical procedure.

Elongate shaft 200 can be produced from a variety of materials, including metal, plastic and composite materials. In one embodiment, proximal shaft 201 is manufactured as a metal tube, for example, as a stainless steel hypotube, and may be coated with a polymeric material such as PTFE. The metal tube may also be covered with a single or multilayered plastic material through one or more processes, including coextrusion, dipping, heat-shrinking, and electrostatic and thermal coating. In another embodiment, elongate shaft 200 is manufactured as a plastic tube. Materials suitable for use in the catheter tube include, but are not limited to, Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6,6, Nylon 6, Nylon 7,11, Nylon 11,12, and blends thereof); block copolymers; PEBA-types polymers, such as ELY, PEBAX, Ubesta, and blends thereof, and biodegradable polymers.

Suitable materials also include blends of the above mentioned materials as well as any composite materials, like dual-layers, tri-layers and multi-layers thereof. For example, catheter shaft may be produced from a tube comprising an outer layer made of Nylon and an inner layer made of a lubricious material such as polyethylene or PTFE. A metallic or nonmetallic braiding may also be included within or between layers of the catheter shaft.

Catheter tip 400 can be configured to provide atraumatic contact between elongate shaft 200 and a wall against which elongate shaft 200 may be pushed during a surgical procedure. The catheter tip can be configured as a soft tip, which in some embodiments, can be composed of a soft sleeve that is affixed on and that extends beyond distal end 202, or, alternatively, that is affixed on and extends beyond the lumen of elongate shaft 200. Typically, a soft tip is affixed through a welding process, but other affixing techniques are also included within the scope of the present subject matter, for example, adhesive bonding. Suitable materials for the sleeve can be chosen from any material suitable for producing elongate shaft 200. The sleeve may be manufactured from a material softer than elongate shaft 200, and may be formed from the same material as expandable member 300 or from a different material, for example, from any of the materials or combinations of materials described with reference to elongate shaft 200. In one embodiment, the sleeve is manufactured from a material having the same basic composition as, but a lower Shore durometer hardness than, the expandable member 300 material or the elongate tube 200 material. In another embodiment, the sleeve may be manufactured from a blend of PEBAX 55D and PEBAX 63D polymers. One skilled in the art will recognize that the sleeve may be manufactured from a variety of other materials according to the previous description of materials, for example, a polyurethane, a polyethylene, a polyolefin, a polyimide, a polyamide like Nylon, a block copolymer, or blends, or compositions or dual layers or multi-layers thereof.

III. The Expandable Member

In accordance with one embodiment of the subject matter, expandable member 300 is a polymeric balloon. Preferably, balloon 300 is a compliant balloon. Unlike a typical angioplasty balloon, which is configured to provide a new circular, open lumen, the polymeric balloon 300 of the embodiment should be sufficiently compliant to mold to the anatomy of the blood vessel. In this manner, balloon 300 can occlude a blood vessel having a diameter from about 2 mm to about 30 mm depending on whether the application is for the coronary, cerebral or peripheral blood vessels. In one embodiment, the balloon can occlude a blood vessel having a diameter from about 2 to about 4.5 mm for coronary or cerebral applications, with a pressure of about 0.5 to 2 atm. For peripheral applications, the balloon can occlude a blood vessel having a diameter from about 4 to about 30 mm, or any luminal orifice of the human body where occlusion of fluid flow could be therapeutic.

In one embodiment, the balloon is a one-size-fits-all balloon. In this regard, the balloon must be formed from a compliant polymeric material. For example and not limitation, the compliant balloon 300 can elongate when it is inflated within a narrow sized vessel, and can have a spherical shape when it inflated within a larger or wider blood vessel. Thus, the balloon is capable of molding to the blood vessel. Accordingly, the physician does not need to measure the artery of a patient prior to postconditioning to size balloon 300 to the patient.

In one embodiment, balloon 300 is mounted to elongate shaft 200 of the catheter. Balloon 300 contains a hollow interior portion defining an inflation passage extending longitudinally therethrough to receive inflation fluid from inflation lumen 203 of elongate shaft 200. In one embodiment, the proximal portion of balloon 300 can be configured to taper radially inward at the proximal end and distal end of balloon 300. The proximal end and the distal end of balloon 300 are sized to mount and seal to respective portions of elongate shaft 200, while the balloon interior portion is configured for selective inflation from an unexpanded first condition to an expanded second condition as shown in FIG. 8. Hence, the transverse cross-sectional dimension of balloon 300, in the expanded condition, is significantly greater than that of the inwardly tapered end portions of proximal end and the distal end of the balloon.

When balloon 300 is mounted to elongate shaft 200, inflation lumen 203 of elongate shaft 200 is in fluid communication with the inflation passage of balloon 300. Accordingly, by operating the one-touch control system at the proximal end of the catheter system, described below, the interior portion of the expandable member 300 can be selectively inflated from the first condition to the inflated second condition.

Distal shaft 202 of the elongate shaft 200 extends through the inflation passage of balloon 300, where a distal end of the catheter terminates distal to the distal end of the balloon 300. As best shown in FIG. 9A, distal shaft 202 extends longitudinally through the interior portion of the balloon 300, and defines the distal portion of the guidewire lumen 205 where it terminates at a distal port at a distal end of the elongate shaft 200. Hence, a guidewire (not shown) may extend through guidewire lumen 205 of the elongate shaft 200, and out through the distal port of the catheter distal end. This passage enables the catheter to be advanced along the guidewire that may be strategically disposed in a vessel.

Figure 13A:
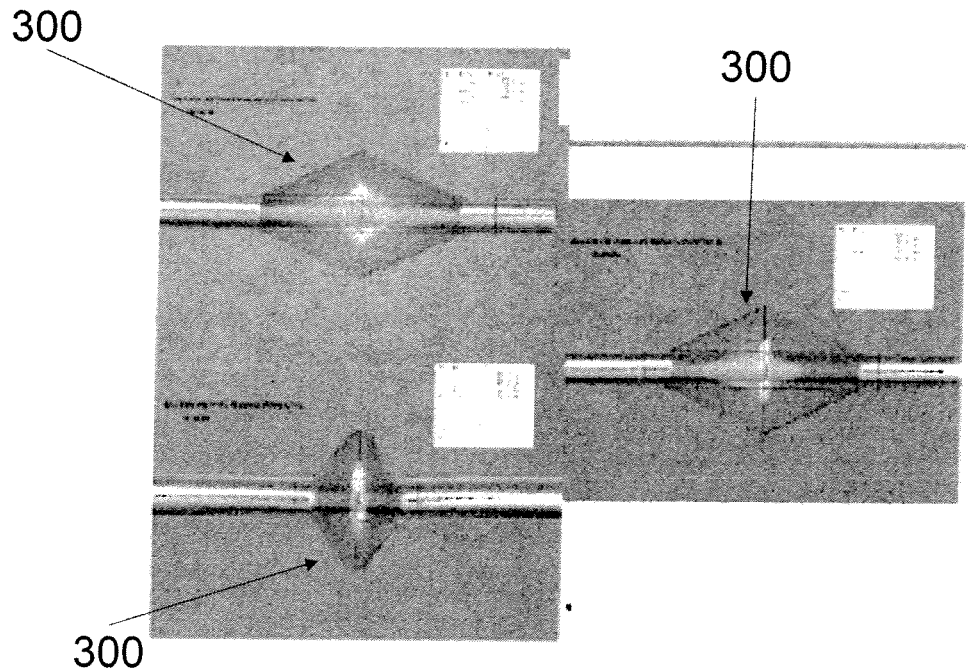
FIGS. 13A and 13B are perspective views of embodiments of balloons in accordance with the disclosed subject matter.
Figure 13B:
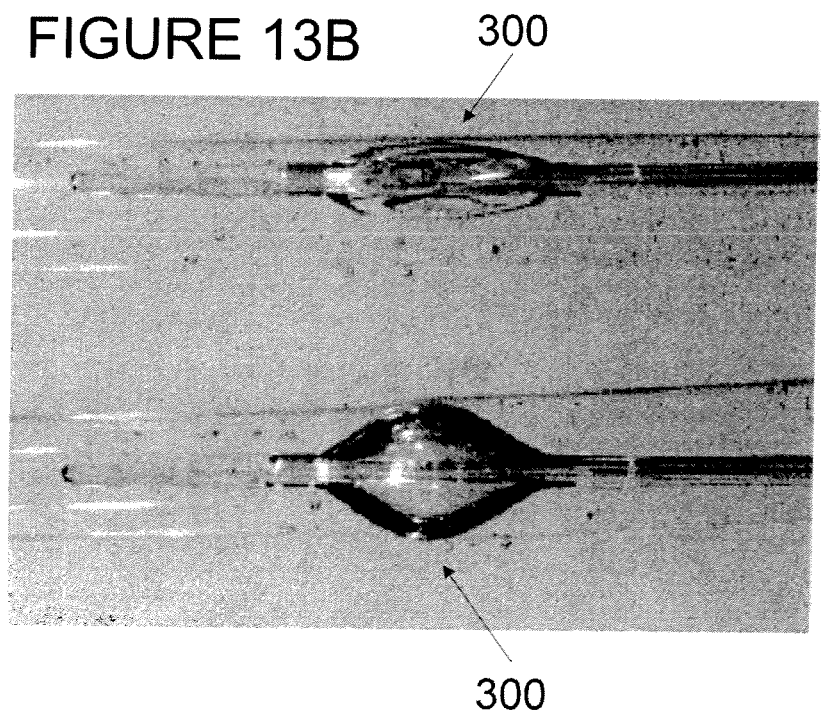

Balloon 300 can be formed in various shapes, as illustrated in FIGS. 13A and 13B. As shown, the shape of balloon 300 can be spherical, cylindrical, or polygonal. Various polymers may be selected for the formation of balloon 300, as would be known in the art. However, the balloon material should be sufficiently compliant such that balloon 300 can mold to the shape of the blood vessel.

In one embodiment, balloon 300 may be formed from a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D is presently preferred, and has a Shore durometer of 65D, an elongation at break of about 300%, and a high tensile strength at yield of about 10,000 psi. However, other suitable grades may be used, including TECOTHANE® 1075D, having a Shore hardness of about D75. Other suitable compliant polymeric materials include ENGAGE® (DuPont Dow Elastomers (an ethylene alpha-olefin polymer) and EXACT® (Exxon Chemical), both of which are thermoplastic polymers, elastomeric silicones, and latexes.

The compliant material may be crosslinked or uncrosslinked. The presently preferred polyurethane balloon materials are not crosslinked. By crosslinking the balloon compliant material, the final inflated balloon size can be controlled.

Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure.

In one embodiment, balloon 300 is formed from a low tensile set polymer such as a silicone-polyurethane copolymer. Preferably, the silicone-polyurethane is an ether urethane and more specifically an aliphatic ether urethane such as PURSIL AL 575A and PURSIL AL10 (Polymer Technology Group), and ELAST-EON 3-70A (Elastomedics), which are silicone polyether urethane copolymers, and more specifically, aliphatic ether urethane cosiloxanes.

In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. The diene polymer can be an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the subject matter include HT 501 available from Apex Medical, and neoprene (i.e., polychloroprene) available from Dupont Elastomers, including Neoprene G, W, T and A types available from Dupont Elastomers.

In one embodiment, the polymeric material is a compliant material such as, but not limited to, a polyamide/polyether block copolymer (commonly referred to as PEBA or polyether-block-amide). Preferably, the polyamide and polyether segments of the block copolymers may be linked through amide or ester linkages. The polyamide block may be selected from various aliphatic or aromatic polyamides known in the art. Preferably, the polyamide is aliphatic. Some non-limiting examples include nylon 12, nylon 11, nylon 9, nylon 6, nylon 6/12, nylon 6/11, nylon 6/9, and nylon 6/6. Preferably, the polyamide is nylon 12. The polyether block may be selected from various polyethers known in the art. Some non-limiting examples of polyether segments include poly(tetramethylene glycol), tetramethylene ether, polyethylene glycol, polypropylene glycol, poly(pentamethylene ether) and poly(hexamethylene ether). Commercially available PEBA material may also be utilized such as for example, PEBAX® materials supplied by Arkema (France). Various techniques for forming a balloon from polyamide/polyether block copolymer are known in the art. One such example is disclosed in U.S. Pat. No. 6,406,457 to Wang, the disclosure of which is incorporated by reference.

In another embodiment, the balloon material is formed from polyamides. Preferably, the polyamide has substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. Preferably, the polyamide is nylon 12. In yet another embodiment, balloon 300 is composed of several different layers, each one being a different polyamide or polyamide/polyether block copolymer.

In accordance with some embodiments, balloon 300 can be composed of a single polymeric layer, or alternatively, can be a multilayered balloon, such as those described in U.S. Pat. No. 5,478,320 to Ishida, U.S. Pat. No. 5,879,369 to Trotta, or U.S. Pat. No. 6,620,127 to Lee, the disclosures of which are incorporated herein by reference.

IV. The Handle and Fluid Circuit

As described above, the catheter system includes a handle 100 generally disposed at or near the proximal end of the catheter. Handle is sized and shaped for comfortable receipt in the practitioners hand. Handle 110 can include a housing of various shapes and configurations, as shown in FIGS. 14C to 14R. In one embodiment, handle 100 is non-removably attached to the catheter such that the system is a unitary device requiring assembly prior to use. In other words, the catheter system can be sold in a "ready-to-use" state, unlike conventional angioplasty catheters as described above.

The fluid circuit generally includes the inflation and independent deflation lumen disposed along the catheter shaft 200, a control system disposed in the handle 100 and a plurality of valves to control and regulate pulsated and/or modulated flow of inflation fluid through the catheter system. The fluid circuit is a "closed" fluid circuit such that the components of the circuit are not exposed to the atmosphere. Accordingly, the inflation fluid is down graded to atmospheric pressure while contained within the fluid circuit.

In some embodiments, elongate shaft 200 includes an inlet port and an outlet port. The inlet port is pressurized by a flow of inflation fluid from a first reservoir as part of the control system 1000 of the fluid circuit. The inflation fluid flows through inflation lumen 203 of elongate shaft 200, enters the interior portion of the expandable member 300 via an inlet port. The inflow of the inflation fluid into the interior of expandable member 300 causes it to inflate and occlude the blood flow in the blood vessel when disposed therein. An outlet port disposed on the elongate shaft 200 facilitates deflation of expandable member 300 by providing an opening for the inflation fluid to flow from expandable member 300 to deflation lumen 204 during deflation.

The outlet port is configured to facilitate Venturi-assisted flow in deflation lumen 204 to deflate expandable member 300. For example, inflation lumen 203 and deflation lumen 204 can both be open within expandable member 300. The inflation fluid can pass from inflation lumen 203, through expandable member 300, into deflation lumen 204. Inflation lumen 203 and the deflation lumen 204 are connected by a series of one-way check valves. In one embodiment, the inflation pressure causes the deflation check valve to stay closed. The pressure buildup (FIG. 15; 117, 112, and 109) on the back side of the check valve and pulse valve create a Venturi effect to promote rapid deflation. When the actuator is manipulated to the deflate position, pressure on the back side of a deflation check valve is removed. Thus the check valve opens and expandable member 300 can deflate. The rapid exhaustion of the inflation pressure creates a Venturi effect, i.e. it draws the balloon down, and pulls the inflation fluid along though the deflation lumen to an exhaust in the handle of the device. The exhaust is not open to the atmosphere. A valve is positioned in the fluid circuit between the deflation lumen and the exhaust in the handle. The valve remains closed to maintain the closed fluid circuit. As the inflation fluid is pulled by the Venturi the pressure of the surging inflation fluid opens the valve so that the deflation fluid can exhaust into the handle. After the deflation fluid is exhausted from the fluid circuit, the valve closes to maintain the closed fluid circuit. The expandable member can be deflated in less than one second, and in some embodiments, less than ¼ of a second.

In one embodiment, as depicted in FIG. 15A, the control system 1000 includes an actuator 107 that is capable of actuating inflation and deflation of expandable member 300 with the ease of a flip of a finger. Actuator 107 can be actuated to sequentially inflate and deflate a balloon for postconditioning applications or other applications. It has been found that reperfusion injury can result from rapid opening of an artery after a period of ischemia or interrupted blood flow, as for example but not limitation during a STEMI or other occlusion. One method for decreasing reperfusion injury is to sequentially start and stop the blood flow in the infracted artery for multiple cycles immediately after reopening the initial flow from the STEMI or other blockage. The present disclosure provides physicians with a system designed to achieve efficient, rapid, reproducible postconditioning. Fluid circuit 110, including control system 1000, is designed to allow operation of the system by a single actuator 107 with no other input or electronics required referred to as "one-touch." Actuator 107 can be configured to include a first position or direction for inflation and a second position or direction for deflation of expandable member 300. For example, the actuator 107 can be a button (FIG. 14F), a switch (FIG. 14A), or a lever (FIG. 14B), having a momentary direction to actuate inflation and a detentable direction to actuate deflation of the balloon. By limiting physician interaction to only one switch, button, or lever, reproducibility in inflating and deflating expandable member 300 in accordance with the time requirements required for postconditioning can be provided. Accordingly, the fluid circuit design and one-touch actuation provides ease of use for postconditioning, and provides a high degree of reproducibility. Additionally, the device embodied herein allows the physician administering postconditioning to focus on the monitor or other instrumentation, as opposed to necessarily focusing on the device during use.

In one embodiment, the inflation fluid is released from the reservoir 101 to regulator or a single pressure check valve, which controls the fluid pressure to the balloon 300. The regulated inflation fluid is not regulated down to atmospheric pressure as the fluid circuit is not open to the atmosphere. The regulated inflation fluid flows through an inlet tubing 106 to the actuator 107, (e.g., switch) which controls the flow of inflation fluid to the pulse valve 113 through a check valve and then to balloon 115.

Figure 16A:
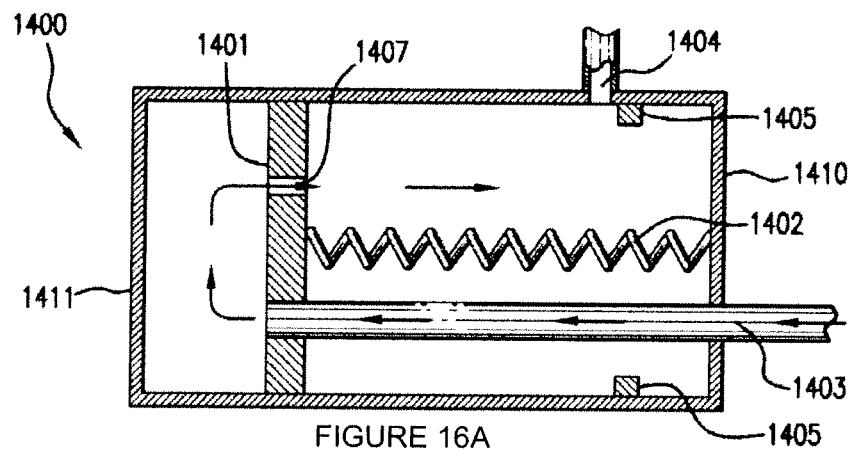
FIGS. 16A to 16C are schematic illustrates of a pulse valve in accordance with the disclosed subject matter.
Figure 16B:
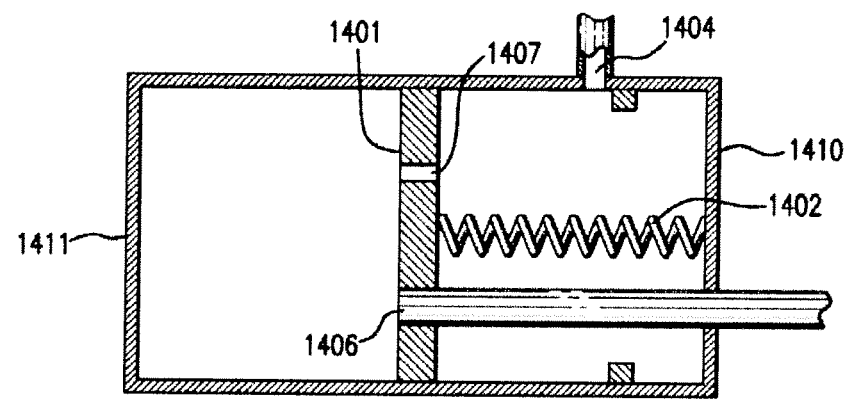
Figure 16C:
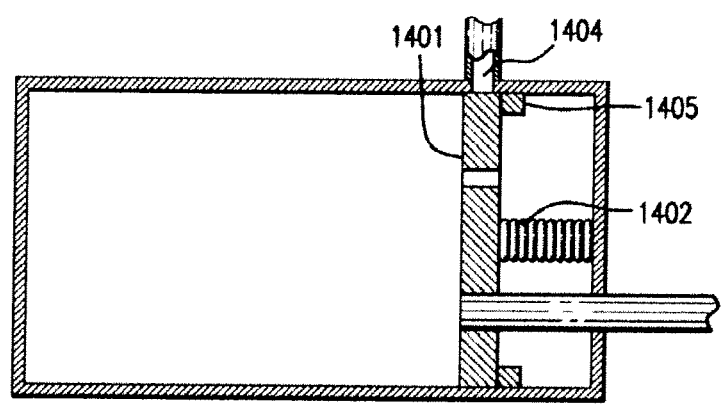

The pulse valve 113 allows inflation fluid to flow from an inlet port to an outlet port within the valve for a specified period of time. The time can be specified, for example, by sizing the inlet port, outlet port, and opposing spring pressure inside the pulse valve, as described below. As best shown in FIGS. 16A to 16C, in one embodiment, the pulse valve 113 includes an inner wall 1401 disposed within cylindrical body 1400. Cylindrical body 1400 has a first end 1410 and opposing second end 1411. An inner wall 1401 having an inlet port 1406 and an outlet port 1407 is disposed within the body 1400 between first and second ends 1410 and 1411. Preferably, the inlet port 1406 is larger than the outlet port 1407 such that inflation fluid flows through the inlet port into the cylindrical body between the second end 1411 and inner wall 1401 at a faster rate than that which flows through the outlet port 1407 to the cylindrical body between the first wall 1410 and inner wall 1401. Accordingly, the amount of inflation fluid entering the inlet port 1406 compared to the amount of inflation fluid exiting the outlet port 1406 causes a buildup of fluid pressure between second wall 1411 and inner wall 1401. The buildup of pressure consequently applies a force to the inner wall and eventually overcomes the strength of spring 1402 and causes the spring to compress, as shown in FIG. 16B as the inner wall is pushed from the pressure buildup. The inner wall 1401 contacts a stop member 1405 disposed within the cylindrical body 1400. In some embodiments a stop is provided on the inner surface of the cylindrical body. The stop is disposed proximate to an outlet port 115 which leads to a pathway to expandable member, e.g., balloon 300 (not shown). As shown in FIG. 16C, the inner wall 1401 contacts stop 1405 and becomes axially aligned with outlet port 115 to balloon 300. When inner wall 1401 is axially aligned with outlet port 115, the passageway provided by the port is blocked so that no inflation fluid can travel to the expandable member 300. Accordingly, the pulse valve 113 provides a "fool-proof" actuator. In this regard, the physician even if continually depressing the actuator to inflate the expandable member 300, cannot further inflate the expandable member because the outlet 115 is blocked by the inner wall 1401. Thus even if additional attempts at inflation are made, the system must de-energize before more inflation fluid is enabled to pass through the system. Thus, the system can safely control the amount of fluid entering an expandable member. The inflation fluid can be various fluids known in the art. For example, the inflation fluid can be a gas fluid or a liquid fluid. For the purpose of illustration, the inflation fluid can be carbon dioxide or saline.

In another embodiment, the fluid circuit includes a Venturi-assisted deflation of the expandable member. In this manner, a vacuum is created to rapidly deflate the inflation fluid from the expandable member. In this regard, when deflation is actuated by the physician, the pulse valve is de-energized, the fluid inside the pulse valve escapes thus relieving the pressure on the back side of a check valve, which creates a Venturi effect that decreases the time to deflate the balloon. In some embodiments, the expandable member deflates in less than about 5 seconds, preferably in less than about 3 seconds, more preferably less than about one second.

Figure 17:
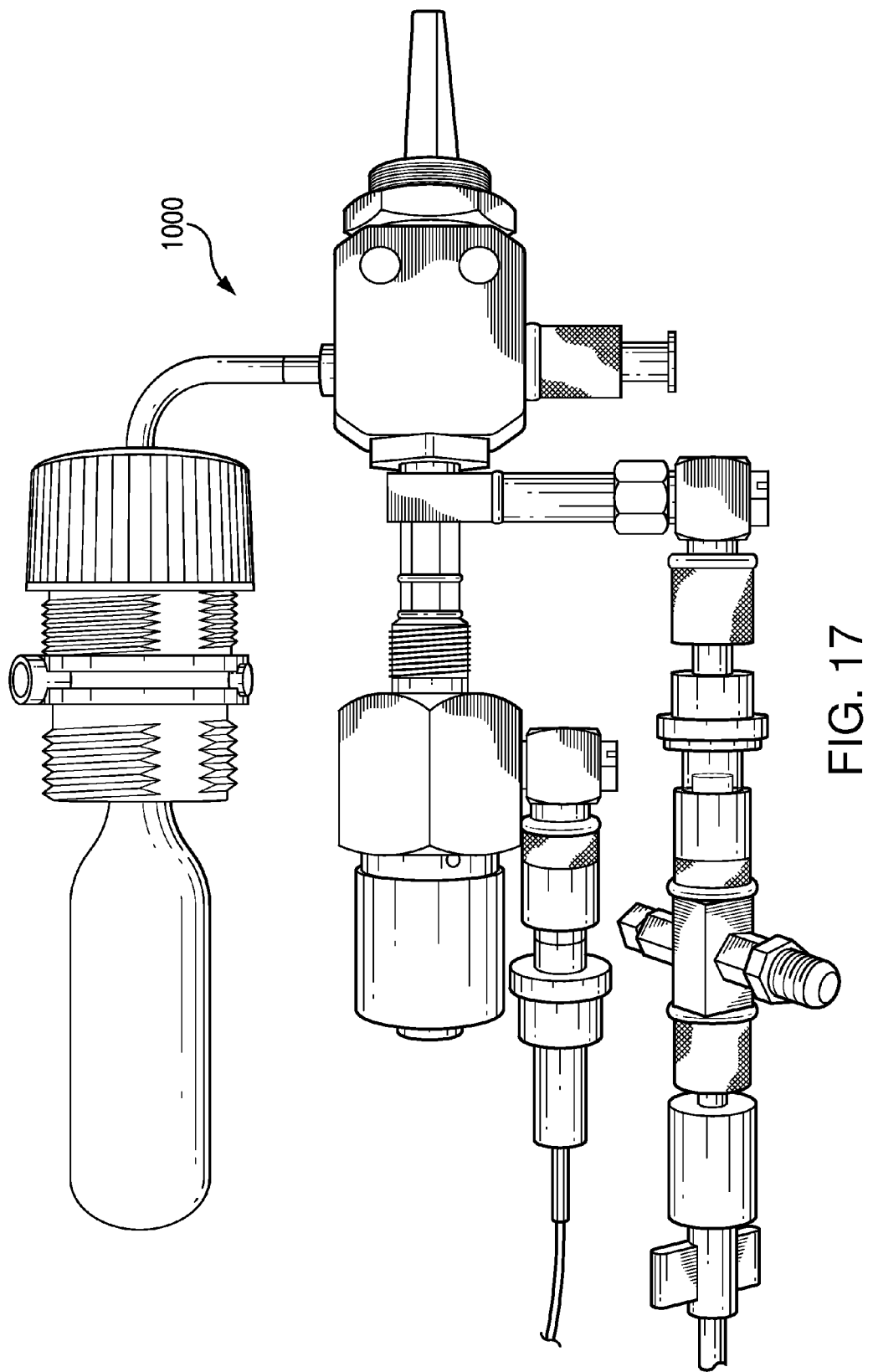
FIG. 17 is a side view of the fluid circuit in accordance with the disclosed subject matter.
Figure 18A:
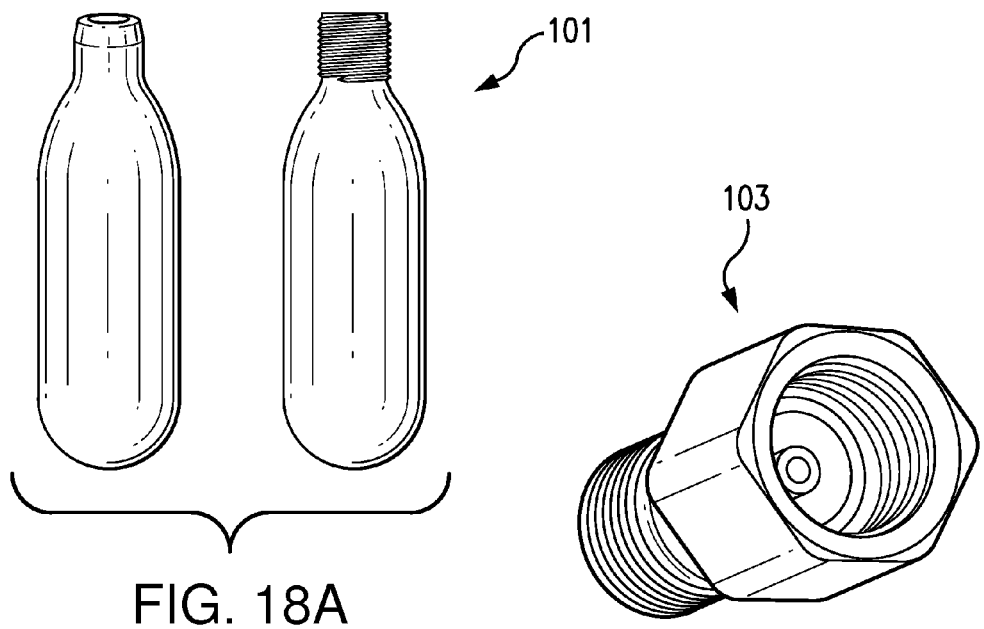
FIGS. 18A to 18T are perspective views of exemplary components of the fluid circuit of FIG. 17.
Figure 18B:
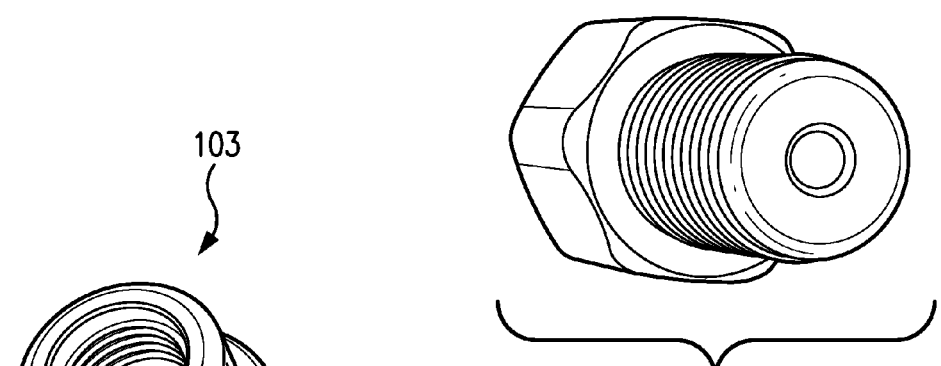
Figure 18C:
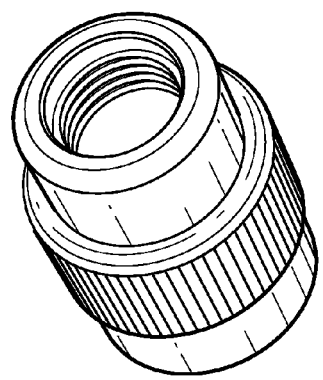
Figure 18D:
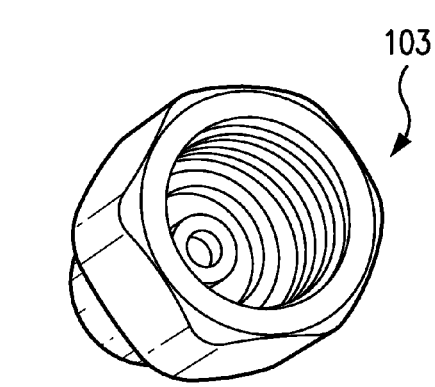
Figure 18E:
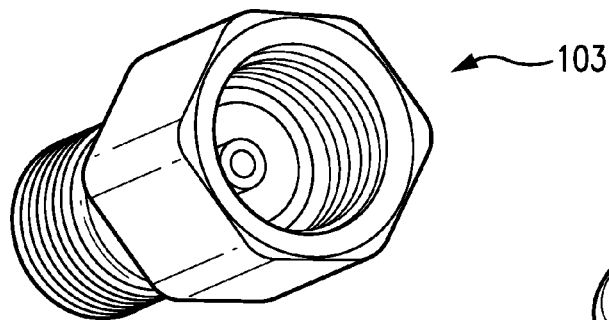
Figure 18F:
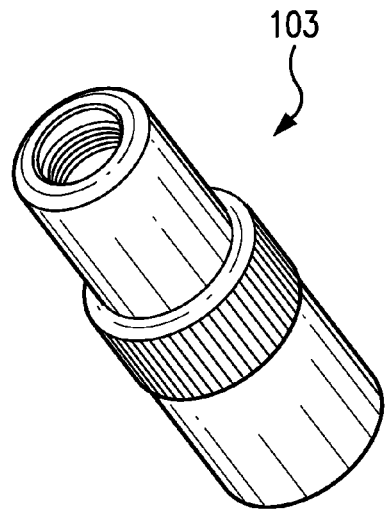
Figure 18G:
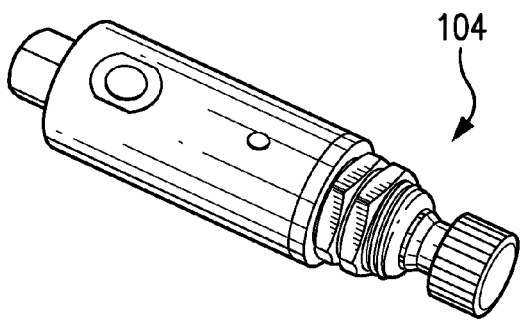
Figure 18H:
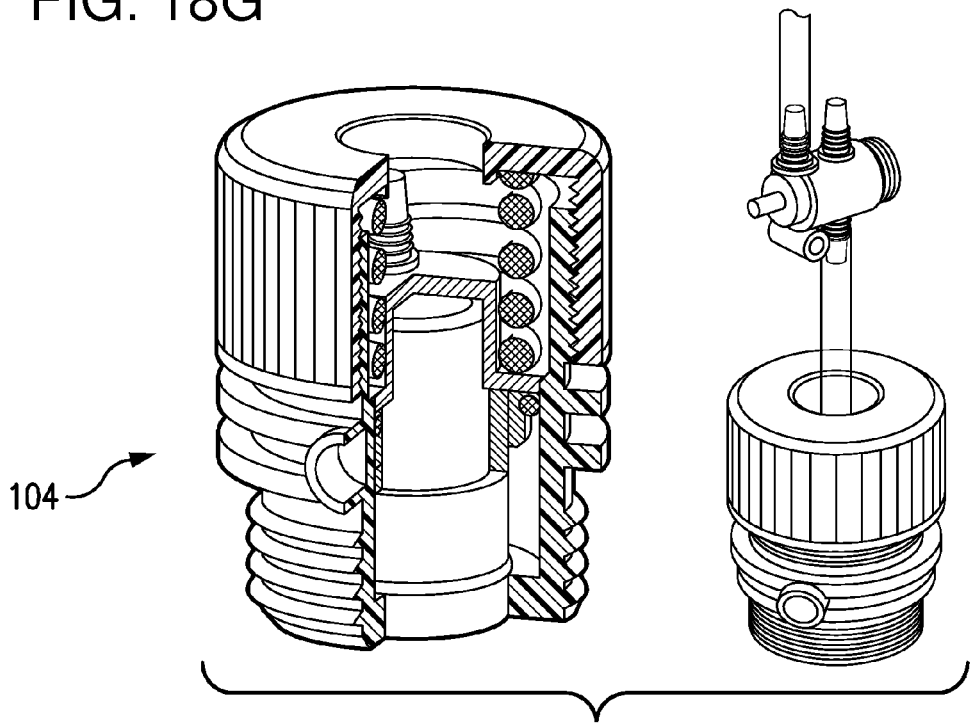
Figure 18I:
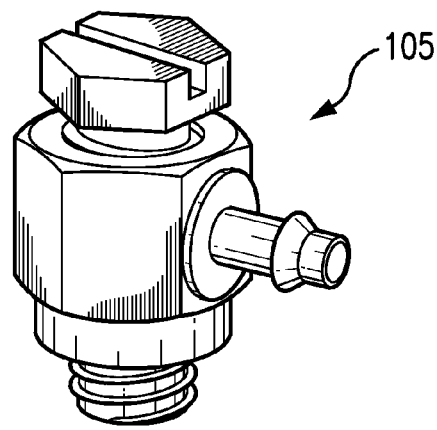
Figure 18J:
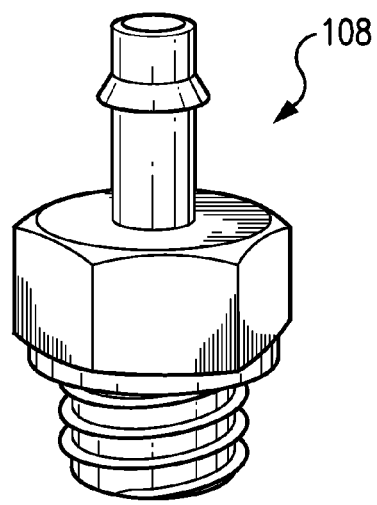
Figure 18K:
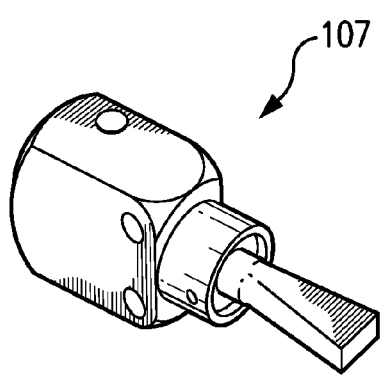
Figure 18L:
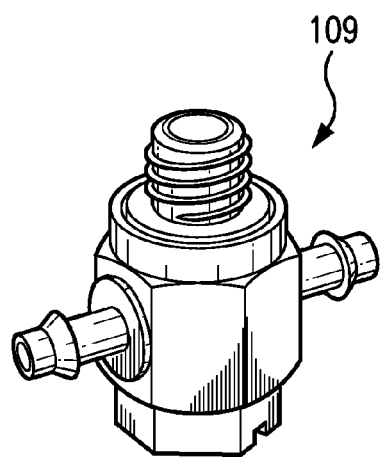
Figure 18Q:
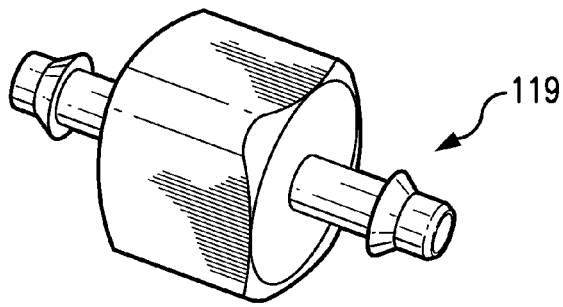
Figure 18R:
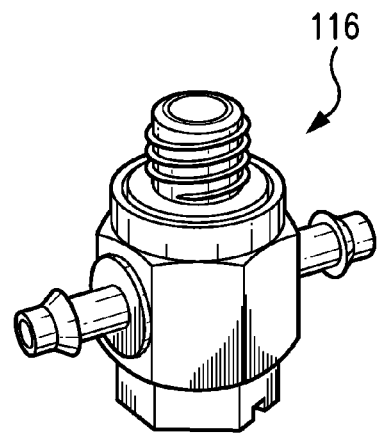
Figure 18S:
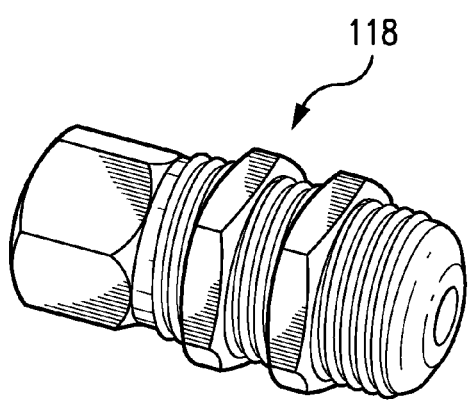
Figure 18T:
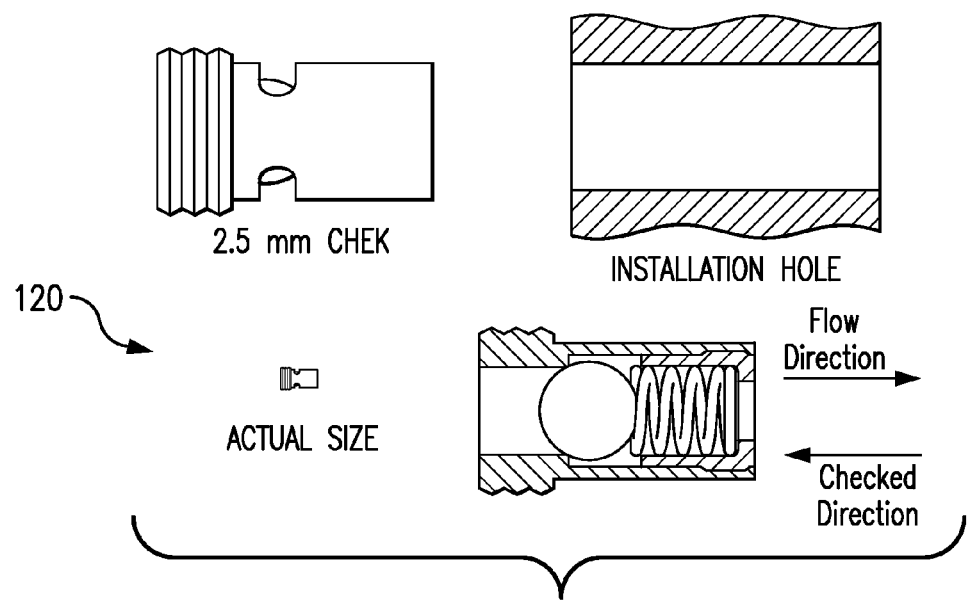

As described herein, the control circuit 1000 as shown in FIG. 17 includes a fluid circuit 110 that generally includes tubing 106 (FIG. 15) and a plurality of check valves to modulate flow of the inflation fluid through the fluid circuit and eventually to the inflation lumen of elongate shaft 200, which is in communication with fluid circuit 110 and expandable member 300 and back through an independent deflation lumen. An exploded view of one embodiment of the fluid circuit is illustrated in FIG. 15. Fluid circuit 110 housed in the handle 100, can include the following component parts: first reservoir 101 to provide high pressure inflation fluid, such as but not limited to a BestWhip (LG) (Genuine Innovations, Part 2042 or 4130) (FIG. 18A); a piercing mechanism 103 to controllably tap the first reservoir 101, such as lance assembly, e.g., SA00102, SA00068, SA00101, or MM235008-21N, MM235008-11N (Genuine Innovations) (FIGS. 18B-18F, respectively); pressure regulator 104 (e.g., MAR-1 (Clippard) or SA00196 (Genuine Innovations), FIGS. 18G-18H, respectively) to control pressure from inflation fluid to expandable member 300. Alternatively, a single pressure check valve or a non-variable pressure regulator can be used such as for example, Qosina—P/N 11582 or "Lee Chek" Part Number CCPI2510014S, (FIG. 18P); connector 105 (not shown) to connect the pressure regulator 104 to tubular member 106, e.g., UTO-2-PKG (Clippard) (FIG. 18I); actuator 107 to control the flow of inflation fluid from first reservoir 101 into expandable member 300; e.g., a main switch such as FBV-3DMF (Clippard) (FIG. 17K); connector 108 to connect tubular member 106 from pressure regulator 104 to actuator 107, e.g., CT2-PKG (Clippard) (FIG. 18J); flow splitter 109 to split the flow of inflation fluid, e.g., UT0-2002-PKG (Clippard) (FIG. 18L); connector 111, such as, e.g., the CT2-PKG (Clippard) (FIG. 18M), to connect flow splitter 109 to pulse valve 113, such as, e.g., PV-1 (Clippard) (FIG. 18N), through tubular member 112 to deliver a volume of controlled pulse of inflation fluid to expandable member 300; a connector 114, such as a rotational connector, e.g., UTO-2-PKG (Clippard) (FIG. 18O), to connect pulse valve 113 to a one-way check valve 115 (e.g., CCPI2510000S (Lee Company) or Qosina—P/N 11582 (FIG. 18P) that permits flow of inflation fluid to expandable member and ensures the flow direction of the inflation fluid is one-way only, i.e., from pulse valve 113 to inflation lumen 203 of elongate shaft 200; flow splitter 116, such as, e.g., UT0-2002-PKG (Clippard) (FIG. 18R) which is connected to flow splitter 109 through tubular member 117, wherein flow splitter 109 connects the hose from deflation lumen 204 to pressure indicator 118; pressure indicator 118, such as, e.g., IND-1-WH (Clippard) (FIG. 18S), for showing that there is pressure in deflation lumen 204 to ensure expandable member 200 is inflated; double hose barb 119 (not shown), such as C22-PKG (Clippard) (FIG. 18Q), for connecting check valve 120 to the hose going to the catheter; and check valve 120, such as CCPI12510000S (Lee Company) (FIG. 18T), to ensure the flow direction of inflation fluid from the outlet lumen on the catheter pulse valve to inlet lumen 203. As illustrated, the fluid circuit needs no electronics to operate.

Figure 19A:
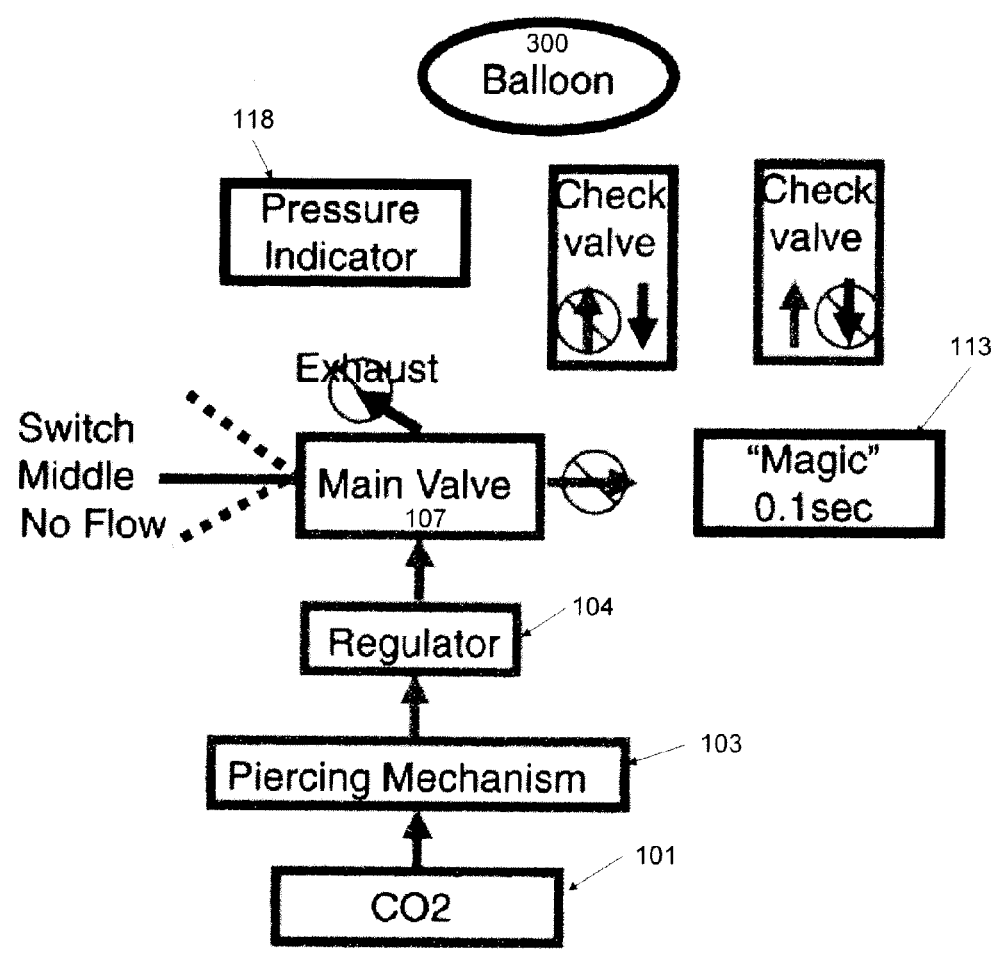
FIGS. 19A to 19C are block diagrams illustrating the inflation fluid flow through the fluid circuit in accordance with one embodiment of the disclosed subject matter.
Figure 19B:
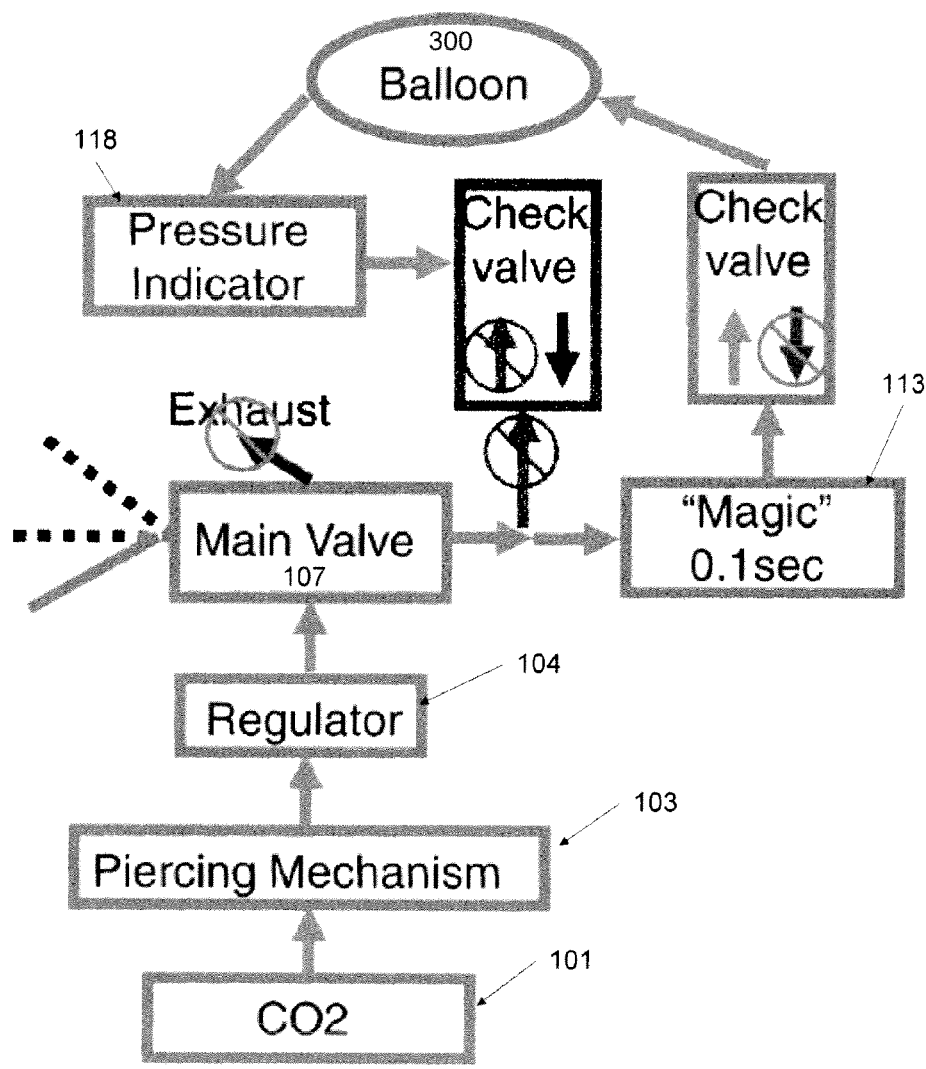
Figure 19C:
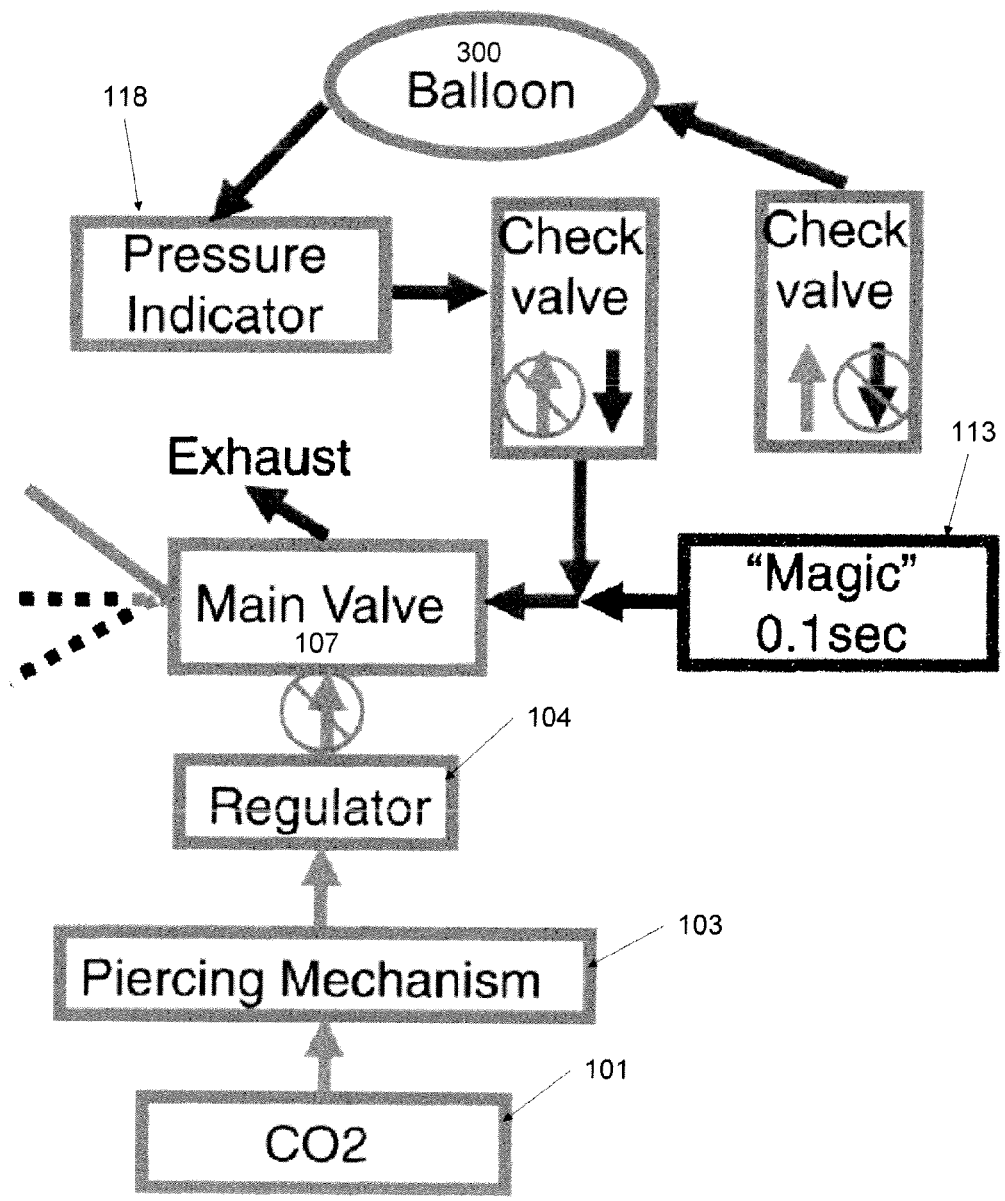

As illustrated in the block diagram of FIG. 19A, in operation the inflation fluid, in this example carbon dioxide, flows out from storage in the first reservoir 101 by a piercing mechanism 103. The inflation fluid flows into a main valve or actuator switch. In some embodiments, the flow of inflation fluid is stopped into and out of the main valve. As shown in FIG. 19B, the fluid circuit can be configured to allow the inflation fluid to flow across the valve into a second check valve. The gas is allowed to flow, in some embodiments, for about 0.1 seconds. After that time, the second valve can be configured to no longer allow flow of the inflation fluid. The check valve allows flow of the inflation fluid into the balloon but not out of the balloon. A third check valve allows inflation fluid flow out of the balloon, but not into the balloon. The inflation fluid, such as the carbon dioxide gas, has a higher pressure when it flows to the inflation check valve, so the system is locked (inflated) at this time. Further, as depicted in FIG. 19C, the pressure inside the second valve exhausts, thereby creating a Venturi force, as noted above, which pulls the balloon into a deflated position as all the gas exhausts out from the top of the main valve. The main valve does not allow gas to flow in at this time. Accordingly, the fluid circuit permits the user to sequentially inflate and deflate the expandable member with the ease of rapid succession. The handle may further include a pulse valve to deliver time-controlled, or volume-controlled flow to the balloon 300. In this regard, the second tubular member may include a one-way check valve to lock the pulse valve delivered carbon dioxide in the expandable member 300.

V. Indicator

Deflation lumen, in some embodiments, includes an indicator, such as but not limited to a pressure monitor, which ensures balloon is inflated. In some embodiments the pressure monitor is disposed in-between the balloon and a deflation check valve to ensure the balloon is inflated. For example, if the catheter is kinked and not allowing inflation, then the indicator will not indicate inflated. Additionally, if the catheter has a leak at the balloon, then the indicator will not indicate inflated. Accordingly, the indicator is a true test of balloon inflation.

In one embodiment, the indicator 118 (FIGS. 14A, 14B, 14C, 15) or a pressure marker is disposed at a proximal end of the system. In one embodiment, the indicator 118 includes a projection member associated with the deflation lumen of the system. In some embodiments, the indicator 118 is configured to extend at least partially through handle 100 when pressure is sensed in the deflation lumen of the system. In this manner, the indicator orientation can inform the physician of the state of the expandable member. In other words, when the indicator extends from the handle housing 100 and is visible to the physician due to, for example, pressure, forcing the button to extend then the physician is cognizant of the fact that inflation fluid is in the expandable member. Conversely, non-extension of the indicator from the handle 100 informs the user that the expandable member is not fully inflated. As the indicator is in associated, such as for example, coupled, to the deflation lumen at the proximal end of the system, the indicator cannot indicate or extend until pressure from the inflation fluid has flowed through the inflation lumen, made fluid communication with the expandable member, and returned through the deflation lumen to the proximal section of the system. Thus, indicator 118 cannot indicate pressure unless the expandable member is inflated at the distal section of the catheter system. Advantageously, the indicator is an indication of the true pressure inside the balloon. Conversely, an indicator which is not in direct fluid communication with a deflation lumen will not truly indicate if the balloon is inflated or deflated.

VI. Arming the Device

Figure 14A:
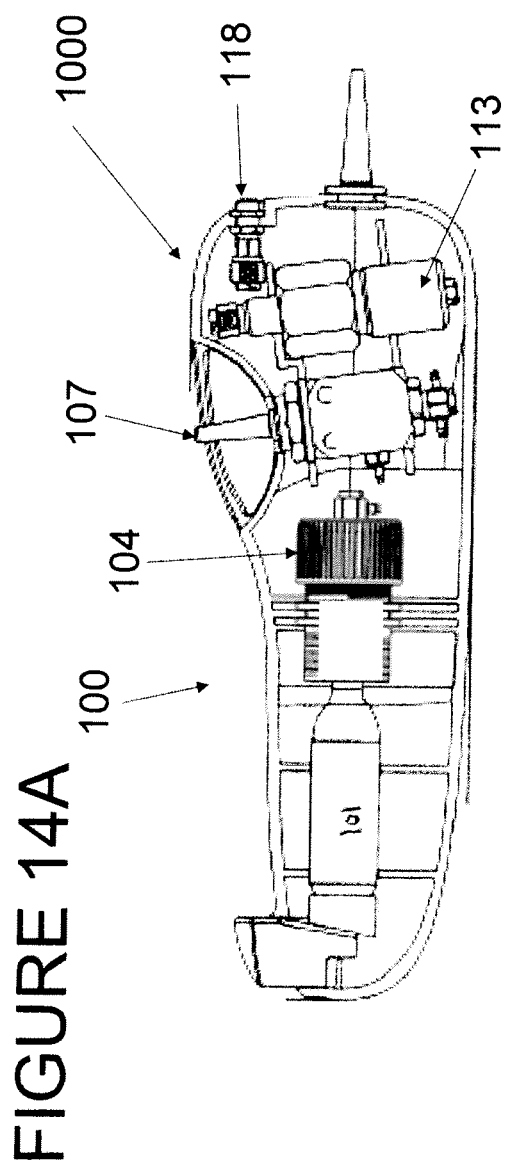
FIGS. 14A and 14B are cross sectional views of some embodiments of the handle in accordance of with the disclosed subject matter.
Figure 14B:
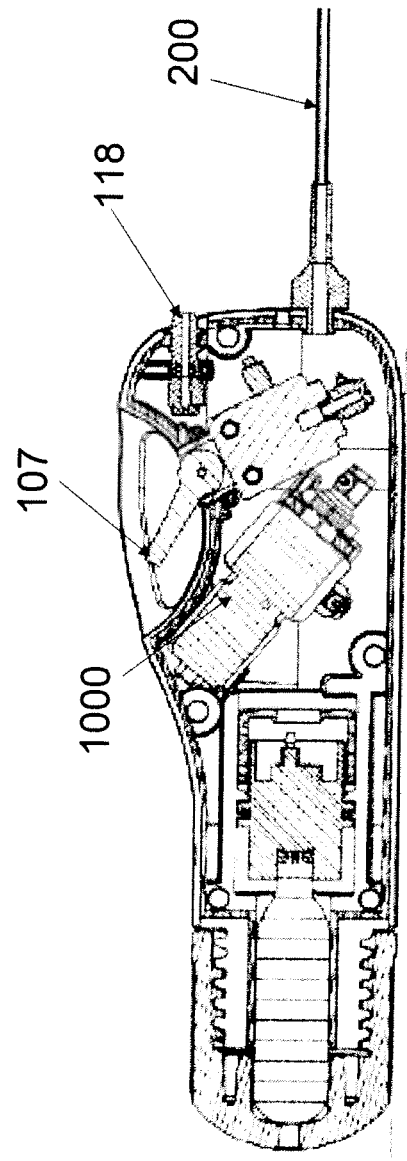
Figure 14C:
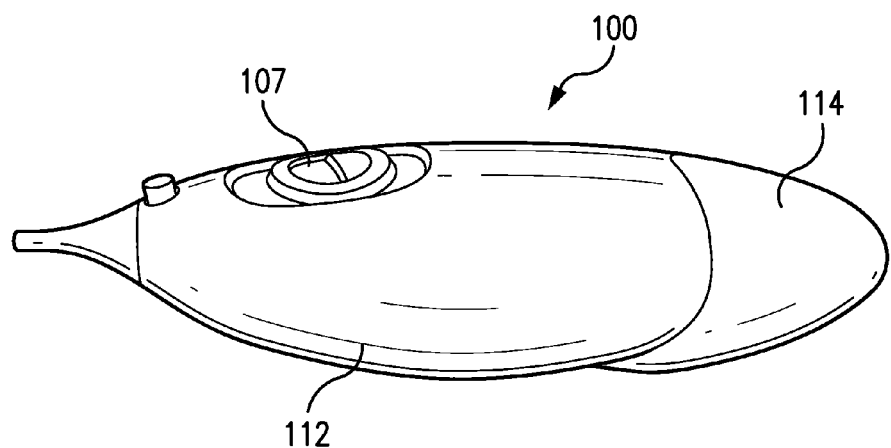
FIGS. 14C to 14R are perspective views of various embodiments of handles in accordance with the disclosed subject matter.
Figure 14D:
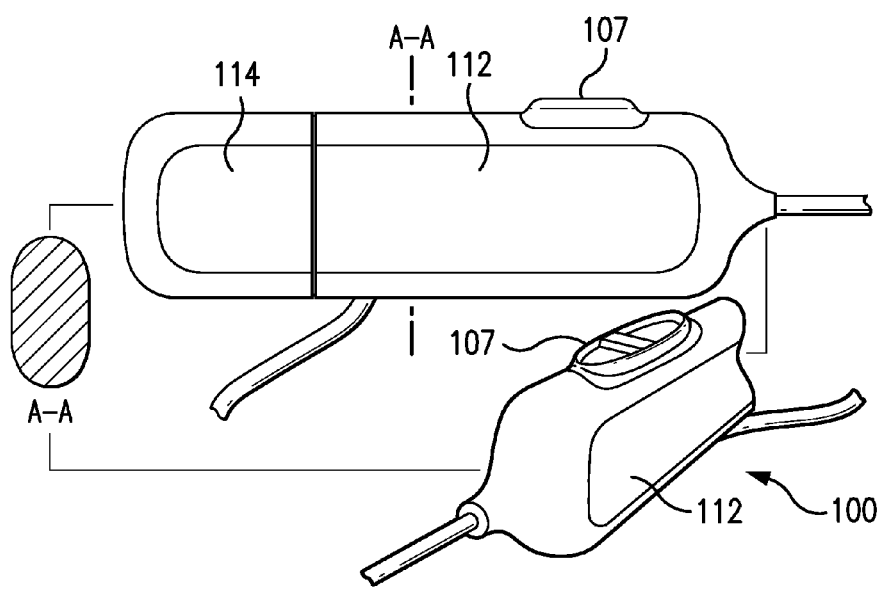
Figure 14E:
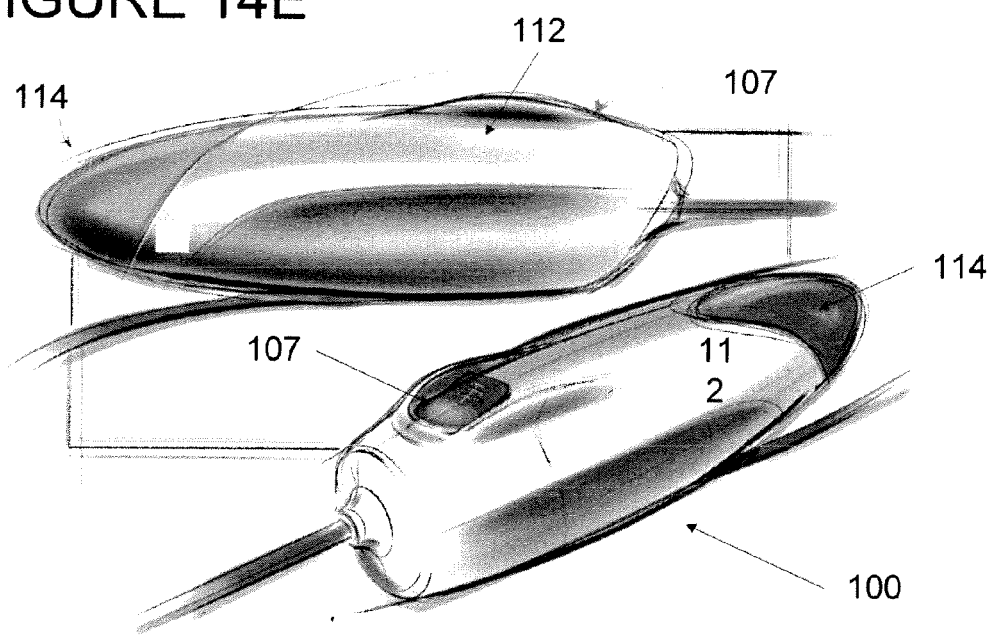
Figure 14F:
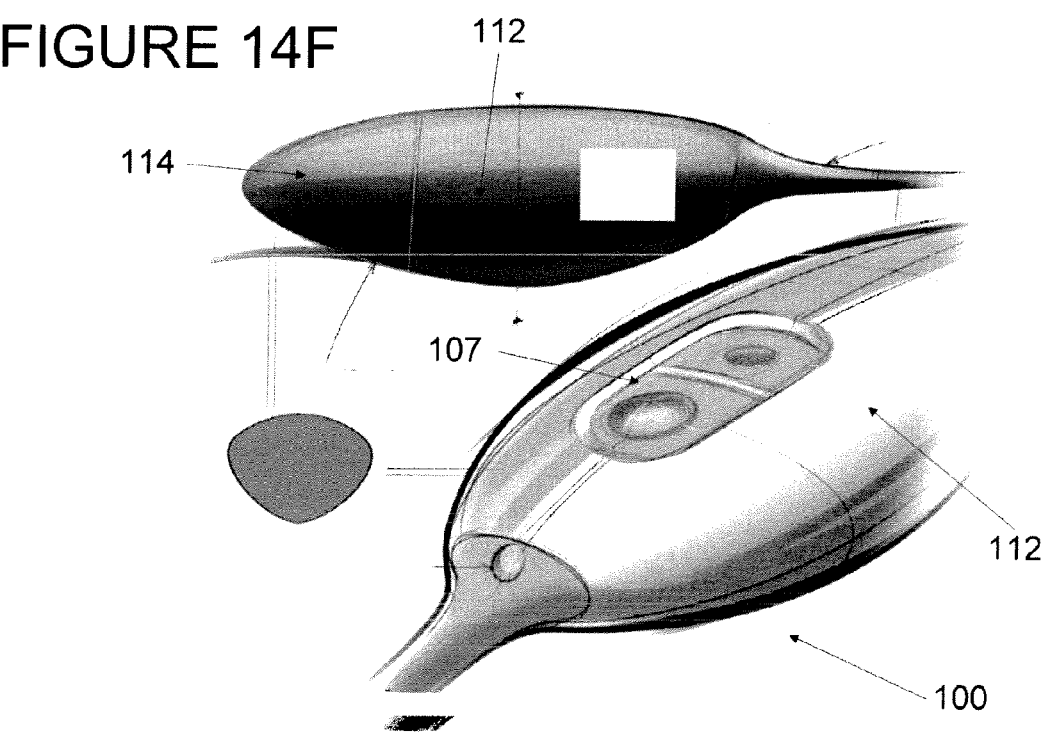
Figure 14G:
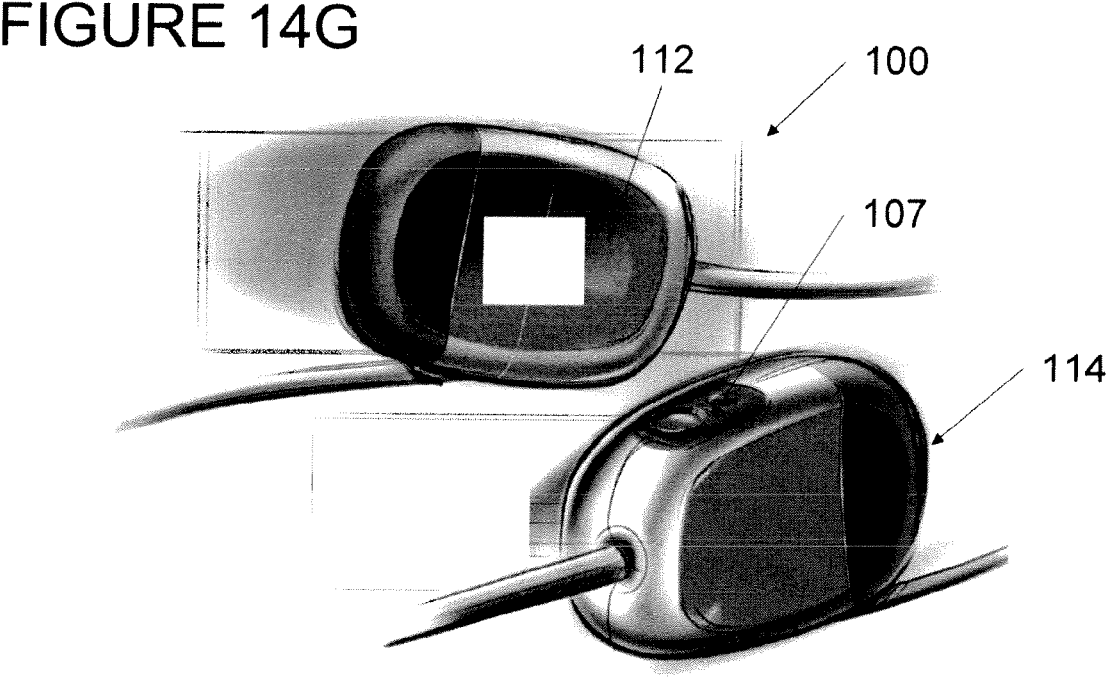
Figure 14H:
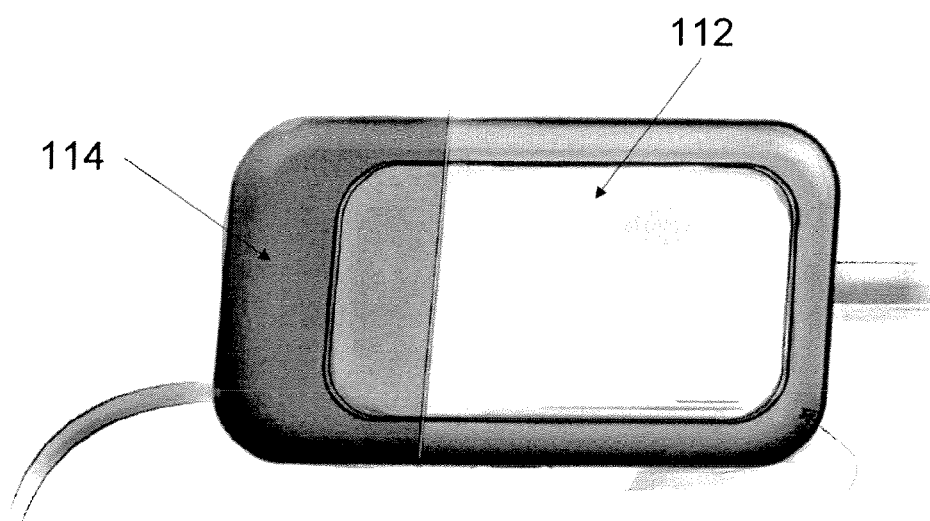
Figure 14I:
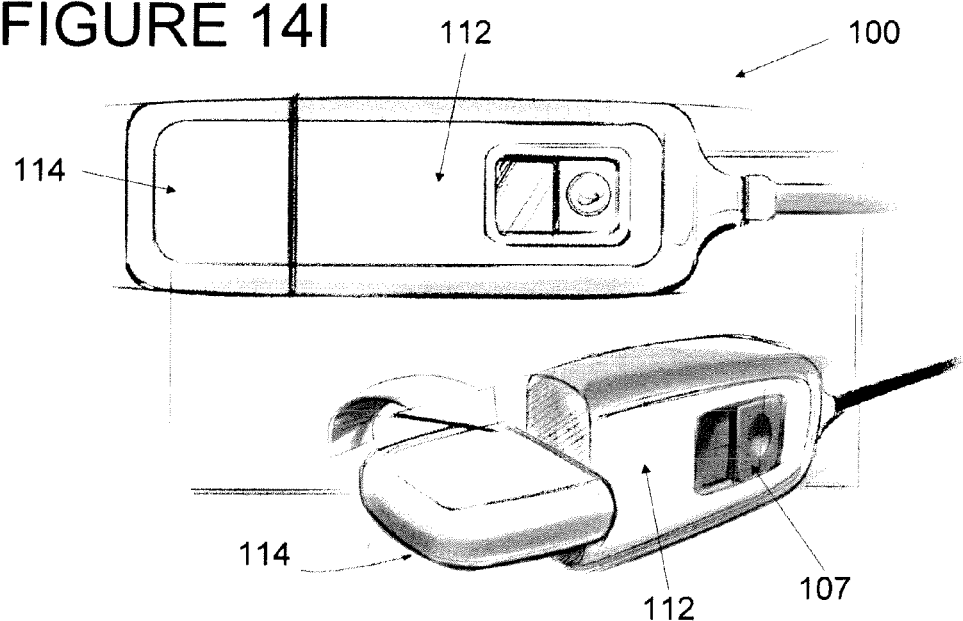
Figure 14J:
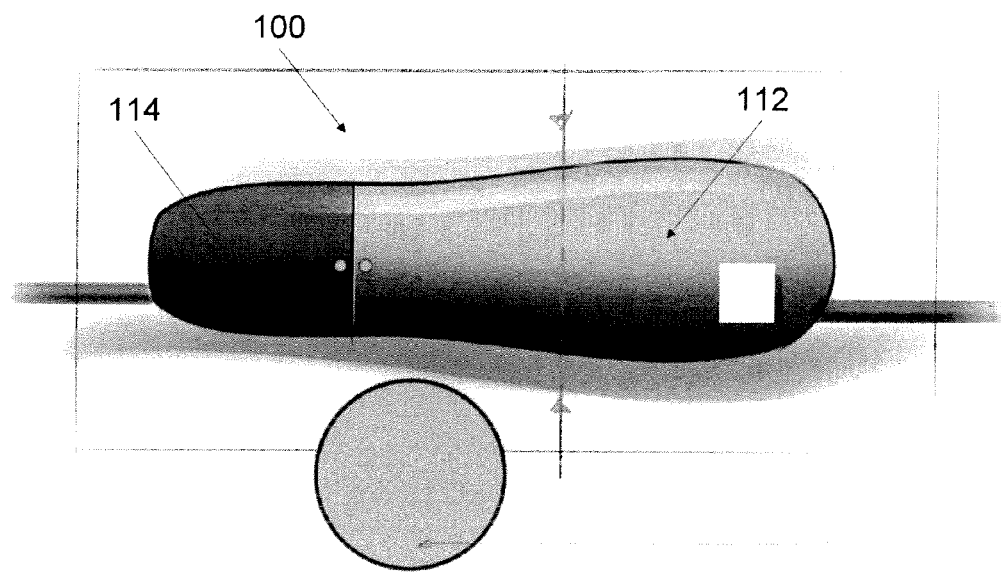
Figure 14K:
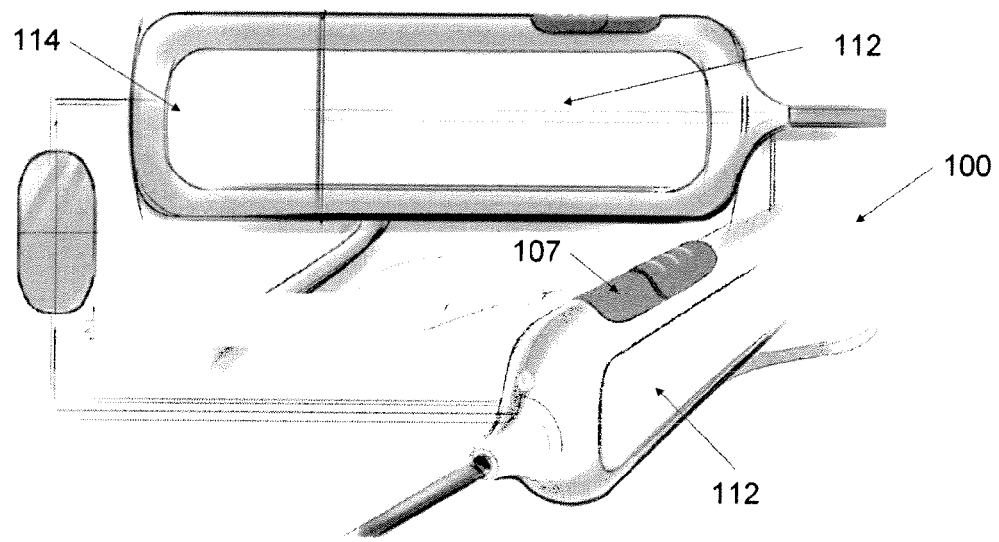
Figure 14L:
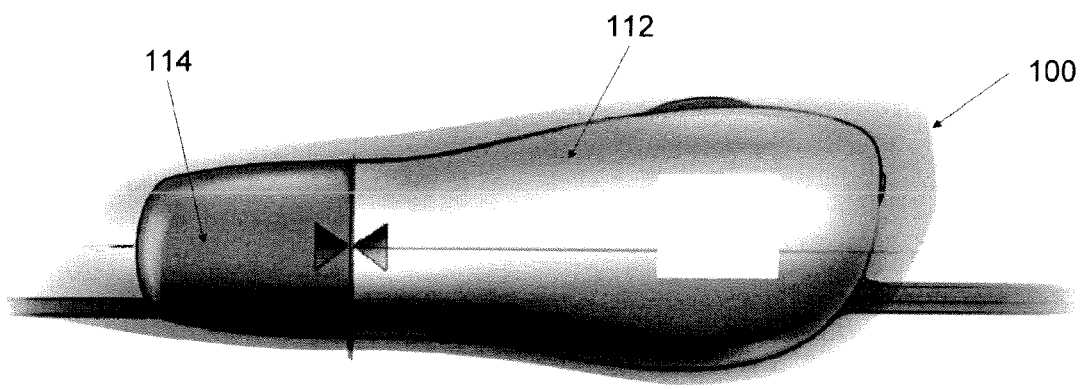
Figure 14M:
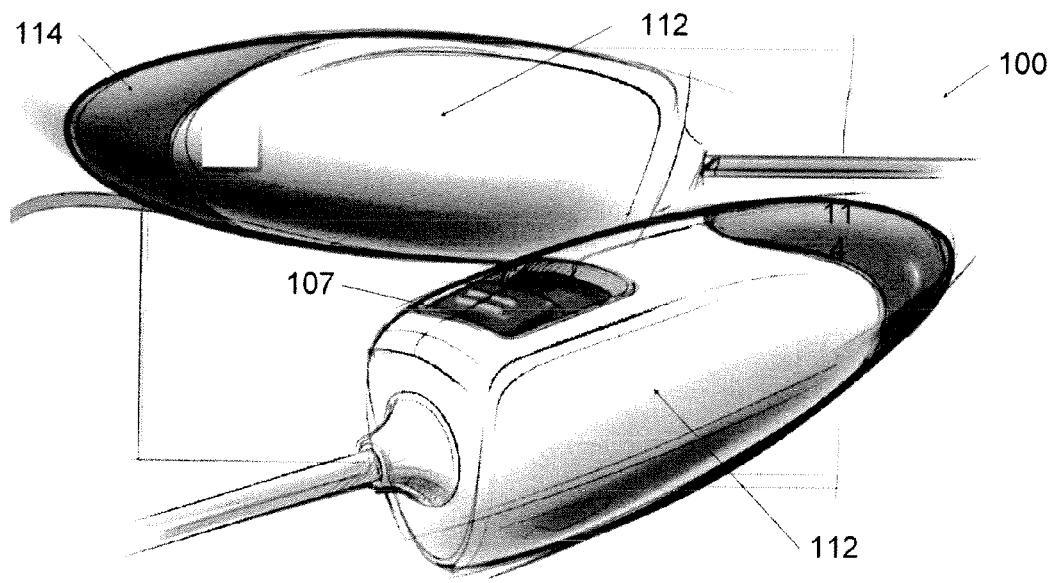
Figure 14N:
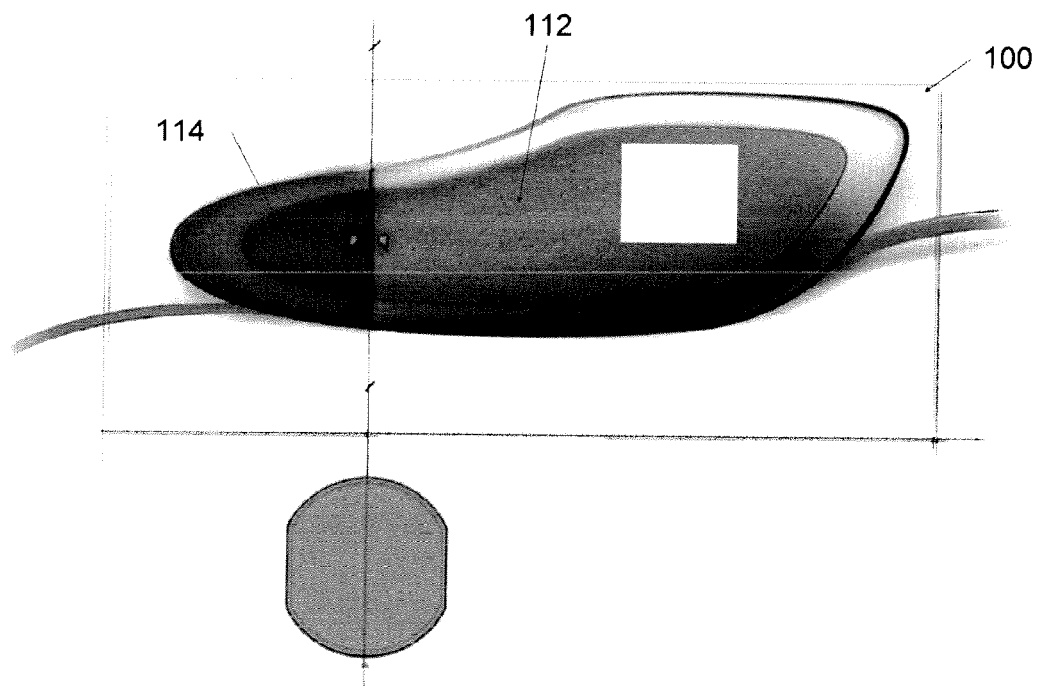
Figure 14O:
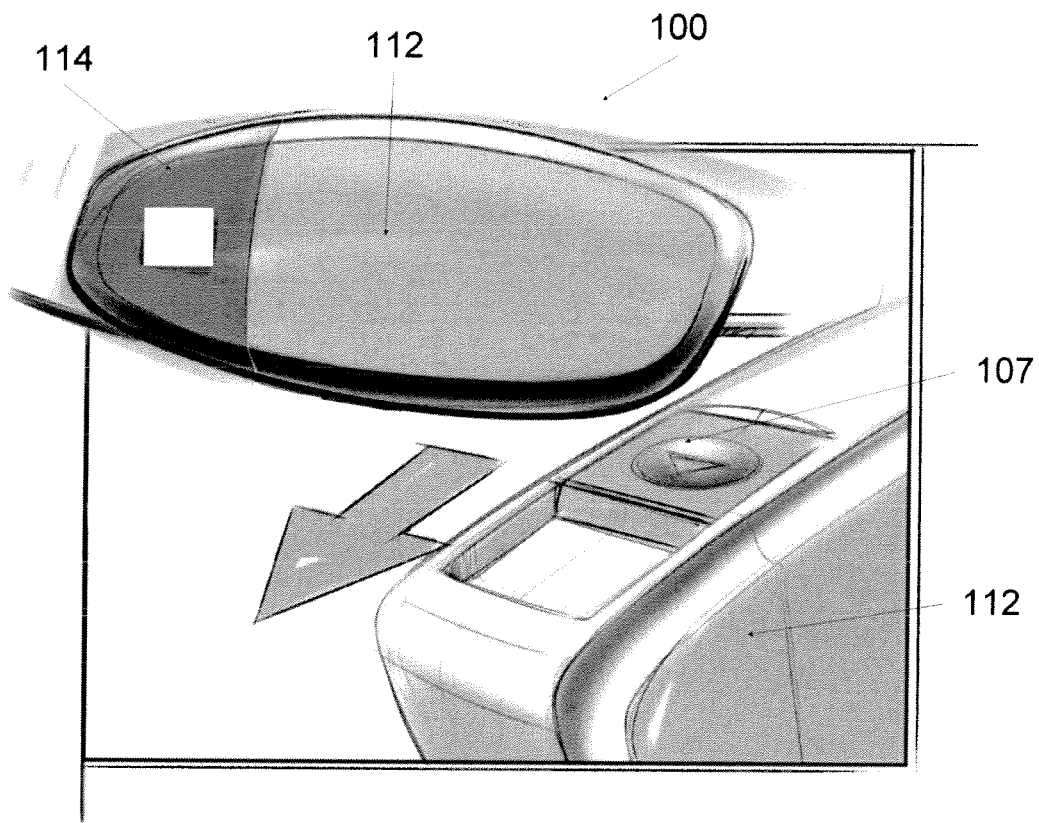
Figure 14P:
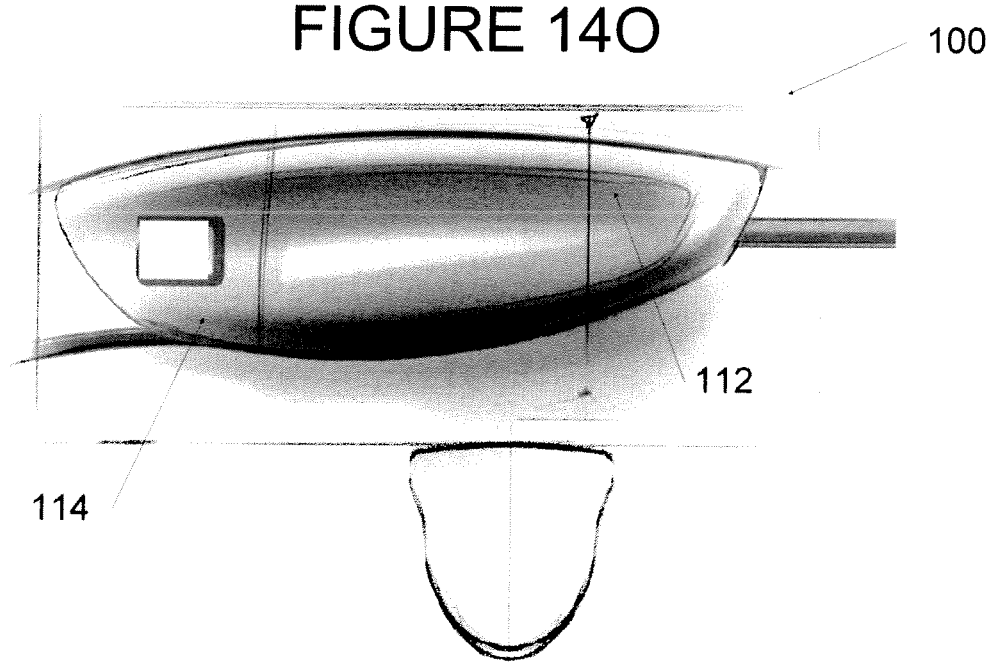
Figure 14Q:
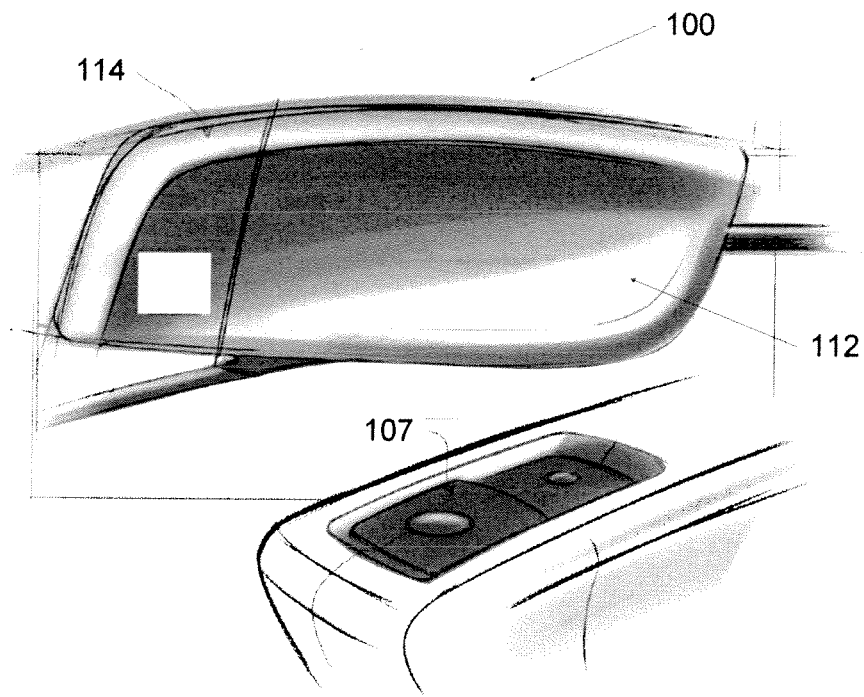
Figure 14R:
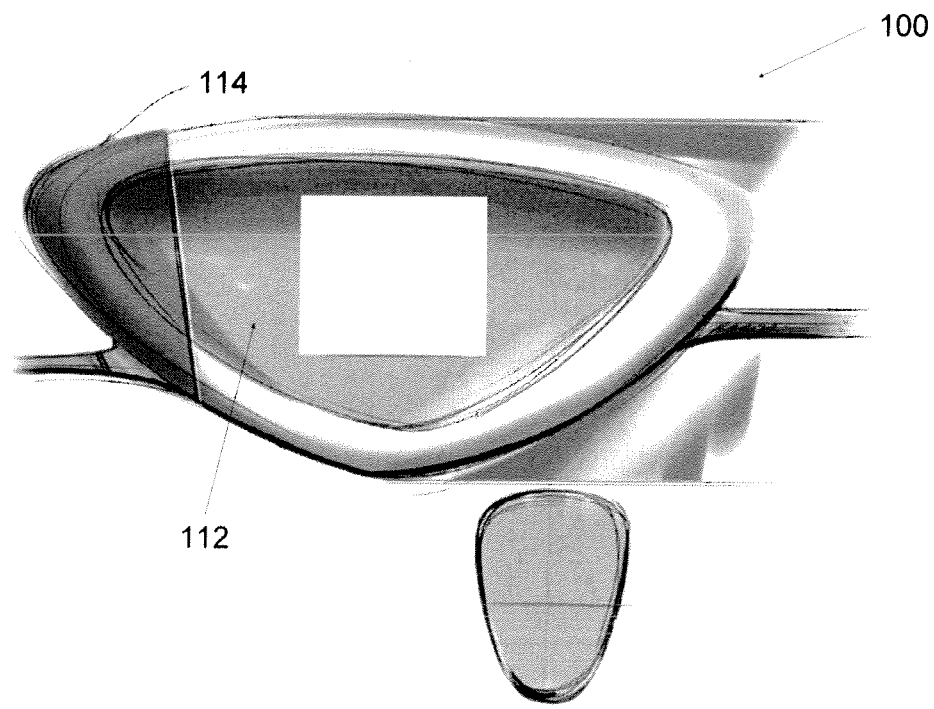

In one embodiment, as shown in the cross sectional views of FIGS. 14A and 14B and best seen in FIG. 15, the control system 1000 of fluid circuit 110 generally includes a first reservoir 101, such as a container or canister, having stored inflation fluid. The first reservoir 101 can be selected (based on size) to inflate and deflate particular balloons of specified sizes. Accordingly, the size of the reservoir selected can prevent reuse and/or promote safety, especially when the inflation fluid is a pressurized gas such as carbon dioxide.

Figure 20C:
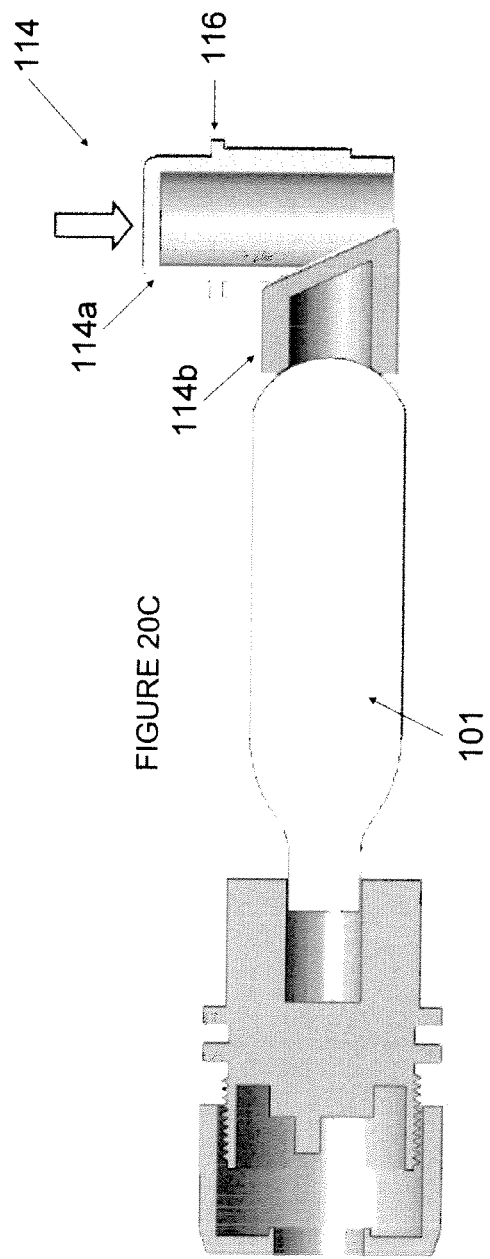
FIGS. 20A to 20N are side views of some embodiments of an arming device in accordance with the disclosed subject matter.
Figure 20D:
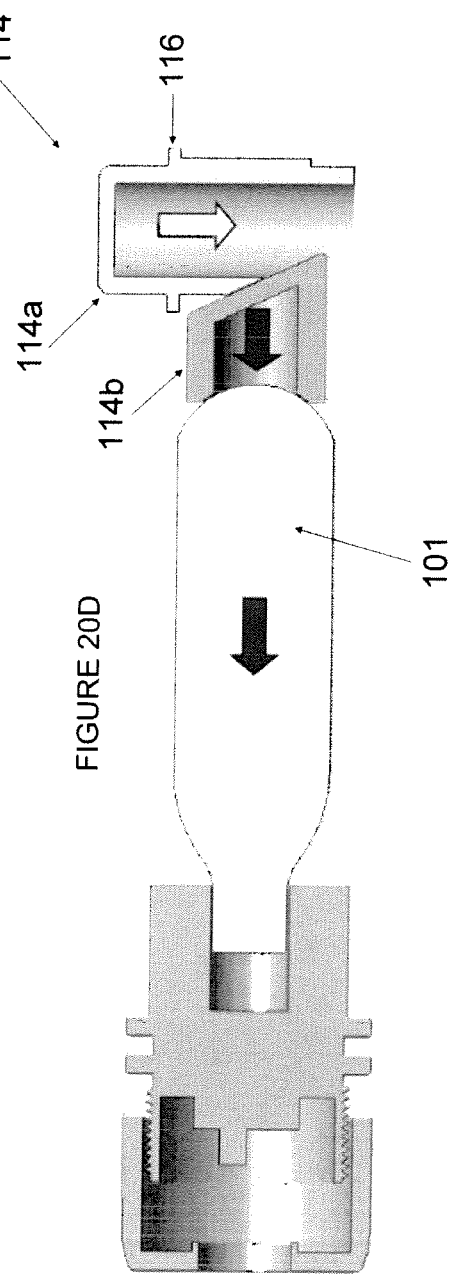

In some embodiments, an arming device 114 (FIG. 20A) is disposed proximal to the first reservoir and is configured to arm the device. The arming device can be non-reversible. In this regard, "non-reversible" means that once the device is armed, it cannot be disarmed. The arming device 114 is actuated by the physician prior to use in order to pierce the reservoir 110 which contains the inflation fluid. For example, as depicted in FIGS. 20A and 20B, when arming device 114 is pushed down, first reservoir 101 is pushed forward and a ratchet located on handle housing 112 engages tab 116, thus preventing arming device 114 from returning to its original position. The system is armed, thereby allowing the fluid to flow from an opening in first reservoir 101.

Further embodiments of arming device 114 are depicted in FIGS. 20C-20N. For example, in FIGS. 20C and 20D, arming device 114 is formed from button 114a and wedge 114b which are positioned such that a downward force on button 114a causes wedge 114b to move in a perpendicular direction, thereby advancing first reservoir 101 forward into an armed position by releasing inflation fluid stored in the reservoir 101. Tab 116 again engages a ratchet located on handle housing 112, preventing both button 114a and wedge 114b from returning to their original positions.

Lever type safeties 114 are depicted in FIGS. 20E to 20J. As shown, the physician must move the lever from a first position to a second position in order to advance first reservoir 101 into its armed position. The initial and final position of lever arming device 114 depend solely on the manufacturing requirements of the system. In some embodiments, a ratchet located on the side of handle housing 112 engages the sides of lever arming device 114, thereby preventing lever arming device 114 from returning to its original position.

A pull tab type arming device 114, as shown in FIGS. 20K-20L, may also be utilized in accordance with some embodiments of the subject matter. In such embodiments, pull tab type arming device may be formed from pull tab 114c and spring mechanism 114d. The spring is biased in a contracted state until the pull tab is removed. By removing pull tab 114c from handle 100, spring mechanism 114d is allowed to expand such that the spring applies a force that pushes or otherwise allows first reservoir 101 to engage a tapping device such as a lancet to arm the device.

In other embodiments, arming device 114 may be a screw type arming device, as depicted in FIGS. 20M-20N. As shown, threads 114e, located on arming device 114, engage an opening in housing 112. Rotating arming device 114 in the appropriate direction causes arming device 114 to advance forward and advance first reservoir 101 into its armed position. In some embodiments, arming device 114 may contain a locking mechanism (not shown) that prevents first reservoir 101 from being disarmed and/or rotating in the wrong direction.

As described the arming device 114 arms the first reservoir 101 by causing engagement of the first reservoir 101 with piercing member 103 (FIGS. 14A, 15) so that the reservoir is tapped or pierced to release the inflation fluid contained in the reservoir housing. The outflow of inflation fluid enters the fluid circuit and eventually flows to the expandable member at the distal section of the catheter body and out from the balloon via an independent deflation lumen VI. Local Administration of Beneficial Agent As described above, the catheter embodied herein can include an infusion lumen 206 for the delivery of beneficial agents. Infusion lumen 206 can be configured to locally administer a drug or other therapeutic to the area of an ischemic event before, during or after postconditioning techniques. In this regard, a health care provided can locally administer an effective amount of beneficial agent to mitigate reperfusion injury to a tissue or organ having suffered or suffering from ischemia.

Accordingly, pursuant to one aspect of the disclosure a method is provided for mitigating infarction of tissue after an ischemic event. In one embodiment, the method inflating a balloon within a blood vessel to at least partially occlude the blood vessel for a first period of time. The first period of time can be from about five seconds or less to one up to five minutes, ten seconds or less to one up to five minutes, fifteen seconds or less to one up to five minutes, twenty seconds or less to one up to five minutes, thirty seconds or less to one up to five minutes. The balloon is then deflated within the blood vessel such that at least partial reperfusion of blood flow is permitted for a second period of time. The second period of time can be longer or shorter than the first period of time. For the purpose of illustration, the second period of time can be five seconds or less to one up to five minutes, ten seconds or less to one up to five minutes, fifteen seconds or less to one up to five minutes, twenty seconds or less to one up to five minutes, thirty seconds or less to one up to five minutes, forty seconds or less to one up to one up to five minutes, fifty second or less to one up to five minutes. After allowing at least partial reperfusion, the balloon can be at least partially inflated to occlude the vessel for a third period of time and then deflating the balloon to allow at least partial reperfusion again. These steps can be repeated in a sequential manner and the beneficial agent can be locally delivered to the area of ischemia during the inflation step, deflation step, or during both steps. In one embodiment, the beneficial agent is administered only during the reperfusion step. In another embodiment, the beneficial agent is delivered every 30 seconds for up to eight cycles of postconditioning. In this manner, a cycle refers to an inflation step (occlusion) and following deflation step (reperfusion).

In accordance with another aspect of the presently disclosed subject matter, the apparatus and method of the present disclosure drastically decreases the amount of contrast required during postconditioning. While contrast media are generally safe to use, medical conditions can be caused by the administration of various contrast media. Reactions can range from minor to severe, sometimes resulting in death. Risk factors for developing severe reactions include strong allergies, bronchial asthma, cardiac disease and beta-blocker use. Accordingly, any reduction in the amount of contrast employed is advantageous in mitigating the risk of an adverse reaction from the patient. For example, use of reduced contrast agent is preferred in patients who are diabetic and other populations with complications.

Figure 21:
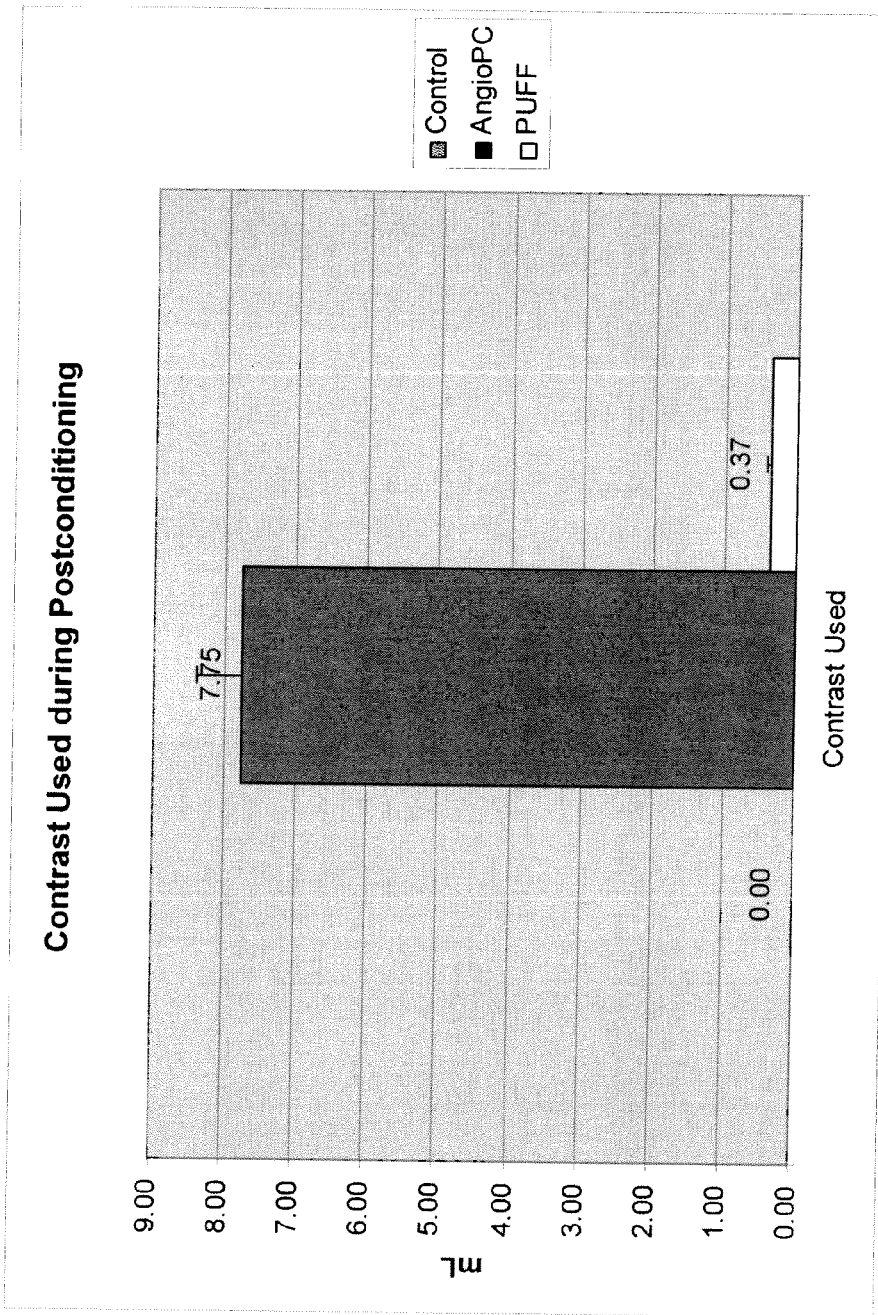
FIG. 21 is a graphical presentation of a comparison of contrast employed, in accordance with the disclosed subject matter.
Figure 22:
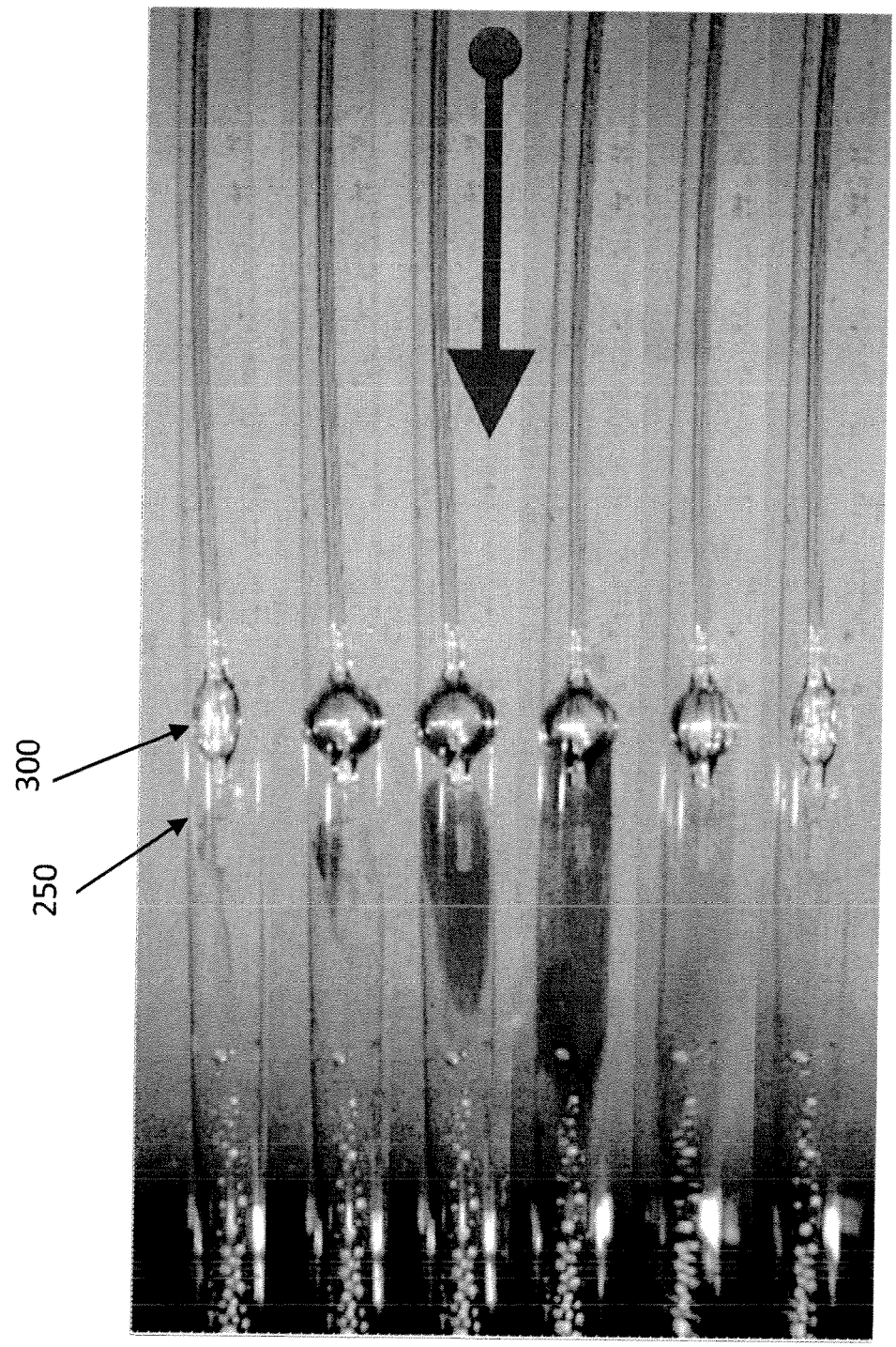
FIG. 22 is a graphical presentation of a series of steps in the reperfusion cycle, depicting delivery of contrast distal the balloon, in accordance with the disclosed subject matter.

As illustrated in FIG. 21, the reperfusion system of the present disclosure, represented by the "PUFF" graph, utilizes 0.37 ml of contrast to confirm eight cycles of postconditioning occlusion and reperfusion, whereas traditional angioplasty techniques, represented by "AngioPC" utilized 7.75 ml. Accordingly, the conventional angioplasty catheter requires nearly twenty-one times for contrast media as compared to the catheter device described and embodied herein. Thus the apparatus and method of the present disclosure substantially reduce contrast exposure. As discussed above with regards to delivering a therapeutic agent, the contrast can be delivered through a lumen of the catheter to an outlet or port positioned distal of the balloon. FIG. 22 depicts a series of images demonstrating a reperfusion cycle in which contrast is deployed at port 250 which is distal of the balloon 300 (the arrow "A" denotes the direction of flow). Since the outlet is disposed distal of the balloon, the balloon can first be inflated to occlude blood flow and then contrast can be delivered. With the blood flow occluded, the contrast is not diluted or forced downstream. Consequently, the present disclosure provides greater control and visibility while requiring less contrast.

The positioning of the delivery port distal of the balloon can enhance the efficacy of therapeutic agent delivery and absorption by the patient. Although a single port 250 is depicted in FIG. 21, additional ports can be included, if so desired. Further, contrast and the therapeutic agent can be provided in separate lumens with separate outlets distal of the balloon, if so desired. In another embodiment, the catheter shaft of presently described subject matter can include a separate lumen to deliver contrast agent separate from beneficial agent. The lumen could be disposed proximal or distal to the balloon, as desired, such that contrast and/or beneficial agent can be delivered proximal or distal to the balloon.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter. While the subject matter has been described and pointed out in detail with reference to exemplary embodiments, it will be understood by those skilled in the art that various changes, modifications, substitutions, and omissions can be made without departing from the spirit of the disclosed embodiments. It is therefore intended that the claimed invention embrace those equivalents within the scope of the claims that follow.

What is claimed is:

1. A method of improving tissue uptake of a beneficial agent, the method comprising:
   introducing a balloon of a balloon catheter into a lumen of a blood vessel of a subject, the balloon being configured to inflate in less than four seconds and deflate in less than five seconds;
   inflating the balloon in less than four seconds and maintaining inflation for a period of time;
   deflating the balloon in less than five seconds, and
   locally administering the beneficial agent into the lumen of the blood vessel,
   wherein the beneficial agent is administered while the balloon is inflated.

2. A method of improving tissue uptake of a beneficial agent, the method comprising:
   introducing a balloon of a balloon catheter into a lumen of a blood vessel of a subject, the balloon being configured to inflate in less than four seconds and deflate in less than five seconds;
   inflating the balloon in less than four seconds and maintaining inflation for a period of time;
   deflating the balloon in less than five seconds, and
   locally administering the beneficial agent into the lumen of the blood vessel,
   wherein the beneficial agent is administered while the balloon is deflated.

3. A method of improving tissue uptake of a beneficial agent, the method comprising:
   introducing a balloon of a balloon catheter into a lumen of a blood vessel of a subject, the balloon being configured to inflate in less than four seconds and deflate in less than five seconds;
   inflating the balloon in less than four seconds and maintaining inflation for a period of time;
   deflating the balloon in less than five seconds, and
   locally administering the beneficial agent into the lumen of the blood vessel,
   wherein the beneficial agent is administered while the balloon is both inflated and deflated.

4. A method of improving tissue uptake of a beneficial agent, the method comprising:
   introducing a balloon of a balloon catheter into a lumen of a blood vessel of a subject, the balloon being configured to inflate in less than four seconds and deflate in less than five seconds;
   inflating the balloon in less than four seconds and maintaining inflation for a period of time;
   deflating the balloon in less than five seconds, and locally administering the beneficial agent into the lumen of the blood vessel, wherein the improved uptake of beneficial agent exhibits a concentration of beneficial agent in blood plasma at least one hour after cessation of administration.

5. The method of claim 4, wherein the method exhibits a plasma concentration of beneficial agent at least two hours after cessation of administration of the beneficial agent and inflation and deflation of the balloon.

6. A method of improving tissue uptake of a beneficial agent, the method comprising:

introducing a balloon of a balloon catheter into a lumen of a blood vessel of a subject, the balloon being configured to inflate in less than four seconds and deflate in less than five seconds;

inflating the balloon in less than four seconds and maintaining inflation for a period of time;

deflating the balloon in less than five seconds, and locally administering the beneficial agent into the lumen of the blood vessel, wherein the beneficial agent is selected from the group consisting of: a calpain inhibitor, pH stabilizing agent, and an endothelin receptor blocker.

7. A method of improving tissue uptake of a beneficial agent, the method comprising:

introducing a balloon of a balloon catheter into a lumen of a blood vessel of a subject, the balloon being configured to inflate in less than four seconds and deflate in less than five seconds;

inflating the balloon in less than four seconds and maintaining inflation for a period of time;

deflating the balloon in less than five seconds, and locally administering the beneficial agent into the lumen of the blood vessel, wherein the beneficial agent includes a biomaterial.

8. A method of improving the ejection fraction after an ischemic event in a subject, comprising:

introducing into an ischemic lumen of the subject a catheter having an inflation lumen and an separate dedicated deflation lumen disposed between a proximal end and a distal end of the catheter and a balloon disposed on the catheter;

sequentially inflating and deflating the balloon for at least two cycles, wherein the ejection fraction in the subject is at least 30%.

9. The method of claim 8, wherein the ejection fraction is at least 33%.

10. The method of claim 8, wherein the ejection fraction is at least 35%.

11. The method of claim 8, wherein the ejection fraction of 30% is maintained for over 7 days.

12. The method of claim 8, wherein the ejection fraction is maintained for over 28 days.

13. The method of claim 8, wherein the ejection fraction increases over time.

14. The method of claim 13, wherein the ejection fraction increases to 40%.

15. The method of claim 13, wherein the ejection fraction increases to at least 50%.

* * * * *